(12) United States Patent
Smith et al.

(10) Patent No.: US 9,878,327 B2
(45) Date of Patent: Jan. 30, 2018

(54) SORTING PARTICLES USING HIGH GRADIENT MAGNETIC FIELDS

(71) Applicant: The General Hospital Corporation, Boston, MA (US)

(72) Inventors: Kyle C. Smith, Cambridge, MA (US); Ramin Haghgooie, Arlington, MA (US); Thomas Alan Barber, Allston, MA (US); Ismail Emre Ozkumur, Cambridge, MA (US); Ravi Kapur, Sharon, MA (US); Mehmet Toner, Charleston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/062,413

(22) Filed: Mar. 7, 2016

(65) Prior Publication Data

US 2016/0263574 A1 Sep. 15, 2016

Related U.S. Application Data

(63) Continuation of application No. 14/410,985, filed as application No. PCT/US2013/047710 on Jun. 25, 2013, now Pat. No. 9,278,353.
(Continued)

(51) Int. Cl.
*G01N 15/06* (2006.01)
*G01N 33/00* (2006.01)
(Continued)

(52) U.S. Cl.
CPC ...... *B01L 3/502761* (2013.01); *B03C 1/0332* (2013.01); *B03C 1/288* (2013.01);
(Continued)

(58) Field of Classification Search
CPC ......... G01N 15/06; G01N 33/00; G01N 33/48
(Continued)

(56) References Cited

U.S. PATENT DOCUMENTS 5,968,820 A    10/1999   Zborowski et al.
5,972,721 A * 10/1999   Bruno et al. .................. 436/526
(Continued)

FOREIGN PATENT DOCUMENTS

CN    101019026     8/2007
CN    101738357     6/2010
(Continued)

OTHER PUBLICATIONS

International Search Report and Written Opinion in International Application No. PCT/US2013/047710, dated Nov. 7, 2013, 6 pages.
(Continued)

*Primary Examiner* — Brian J Sines
(74) *Attorney, Agent, or Firm* — Fish & Richardson P.C.

(57) ABSTRACT

This disclosure describes microfluidic devices that include one or more magnets, each magnet being operable to emit a magnetic field; and a magnetizable layer adjacent to the one or more magnets, in which the magnetizable layer is configured to induce a gradient in the magnetic field of at least one of the magnets. For example, the gradient can be at least $10^3$ T/m at a position that is at least 20 μm away from a surface of the magnetizable layer. The magnetizable layer includes a first high magnetic permeability material and a low magnetic permeability material arranged adjacent to the high magnetic permeability material. The devices also include a microfluidic channel arranged on a surface of the magnetizable layer, wherein a central longitudinal axis of the microfluidic channel is arranged at an angle to or
(Continued)

laterally offset from an interface between the high magnetic permeability material and the low magnetic permeability material.

7 Claims, 36 Drawing Sheets

Related U.S. Application Data

(60) Provisional application No. 61/664,051, filed on Jun. 25, 2012.

(51) Int. Cl.
| | |
|---|---|
| *G01N 33/48* | (2006.01) |
| *B01L 3/00* | (2006.01) |
| *G01N 1/40* | (2006.01) |
| *G01N 33/543* | (2006.01) |
| *B03C 1/28* | (2006.01) |
| *G01N 33/487* | (2006.01) |
| *B03C 1/033* | (2006.01) |

(52) U.S. Cl.
CPC ..... *G01N 1/4077* (2013.01); *G01N 33/48735* (2013.01); *G01N 33/54333* (2013.01); *B01L 2200/0652* (2013.01); *B01L 2200/0668* (2013.01); *B01L 2200/12* (2013.01); *B01L 2300/06* (2013.01); *B01L 2300/12* (2013.01); *B01L 2400/043* (2013.01); *B03C 2201/18* (2013.01); *B03C 2201/26* (2013.01)

(58) Field of Classification Search
USPC ...... 422/68.1, 502, 503, 82.01; 436/43, 174, 436/180, 149, 150, 151
See application file for complete search history.

(56) References Cited

U.S. PATENT DOCUMENTS

| | | | |
|---|---|---|---|
| 6,027,945 A * | 2/2000 | Smith et al. ............ | 436/526 |
| 6,716,642 B1 | 4/2004 | Wu et al. | |
| 6,790,330 B2 | 9/2004 | Gascoyne et al. | |
| 7,285,412 B2 | 10/2007 | Casagrande et al. | |
| 7,837,379 B2 | 11/2010 | Fiering et al. | |
| 8,186,913 B2 | 5/2012 | Toner et al. | |
| 9,278,353 B2 | 3/2016 | Smith et al. | |
| 2002/0022276 A1 * | 2/2002 | Zhou et al. ............ | 436/518 |
| 2003/0092029 A1 | 5/2003 | Josephson et al. | |
| 2003/0124194 A1 | 7/2003 | Gaw et al. | |
| 2006/0269965 A1 | 11/2006 | Josephson et al. | |
| 2006/0292013 A1 * | 12/2006 | Love et al. ............ | 417/207 |
| 2008/0023388 A1 | 1/2008 | Cho et al. | |
| 2008/0124779 A1 | 5/2008 | Oh et al. | |
| 2008/0302732 A1 | 12/2008 | Soh et al. | |
| 2009/0220932 A1 | 9/2009 | Ingber et al. | |
| 2011/0091987 A1 | 4/2011 | Weissleder et al. | |
| 2012/0187938 A1 | 7/2012 | Bar et al. | |
| 2013/0065795 A1 | 3/2013 | Allbritton et al. | |
| 2013/0189755 A1 | 7/2013 | Han et al. | |
| 2013/0333820 A1 * | 12/2013 | Sherrer ............ | 156/60 |

FOREIGN PATENT DOCUMENTS

| | | |
|---|---|---|
| DE | 10 2009 047801 | 3/2011 |
| JP | 2006-010529 | 1/2006 |
| JP | 2010-518403 | 5/2010 |
| KR | 2010-0040195 | 4/2010 |
| KR | 20100088957 | 9/2010 |
| KR | 20110057095 | 6/2011 |
| KR | 10-2012-0026959 | 3/2012 |
| KR | 2012-0026959 | 3/2012 |
| RU | 68497 | 11/2007 |
| SU | 810277 | 3/1981 |
| WO | 00/61191 | 10/2000 |
| WO | WO 2008/098236 | 8/2008 |
| WO | WO 2009/132151 | 10/2009 |
| WO | WO 2011006105 | 8/2011 |
| WO | 2012/033291 | 3/2012 |

OTHER PUBLICATIONS

International Preliminary Report on Patentability in International Application No. PCT/US2013/047710, dated Dec. 31, 2014, 5 pages.
Office Action issued in Chinese Application No. 201380042623.9 on Mar. 2, 2016, 11 pages (with English translation).
European Search Report issued in European Application No. 13809442.0 on Mar. 3, 2016, 4 pages.
Chinese Office Action for Application No. 201380042623.9, dated Sep. 13, 2016, 18 pages (With English Translation).
European Office Action for Application No. 13809442.0, dated Sep. 13, 2016, 7 pages.
Japanese Office Action in Application No. 2015-520411, dated Oct. 4, 2017, 12 pages (with English translation).
European email communication from Examiner Carol Holubov in Application No. 13809442.0, dated Oct. 23, 2017, 2 pages.
European Office Action in Application No. 13809442.0, dated Jul. 24, 2017, 5 pages.
Chinese Office Action in Application No. 201380042623.9, dated Jun. 27, 2017, 43 pages (with English translation).
Japanese Office Action for Application No. 2015-520411, dated Mar. 1, 2017, 8 pages (with English translation).

\* cited by examiner

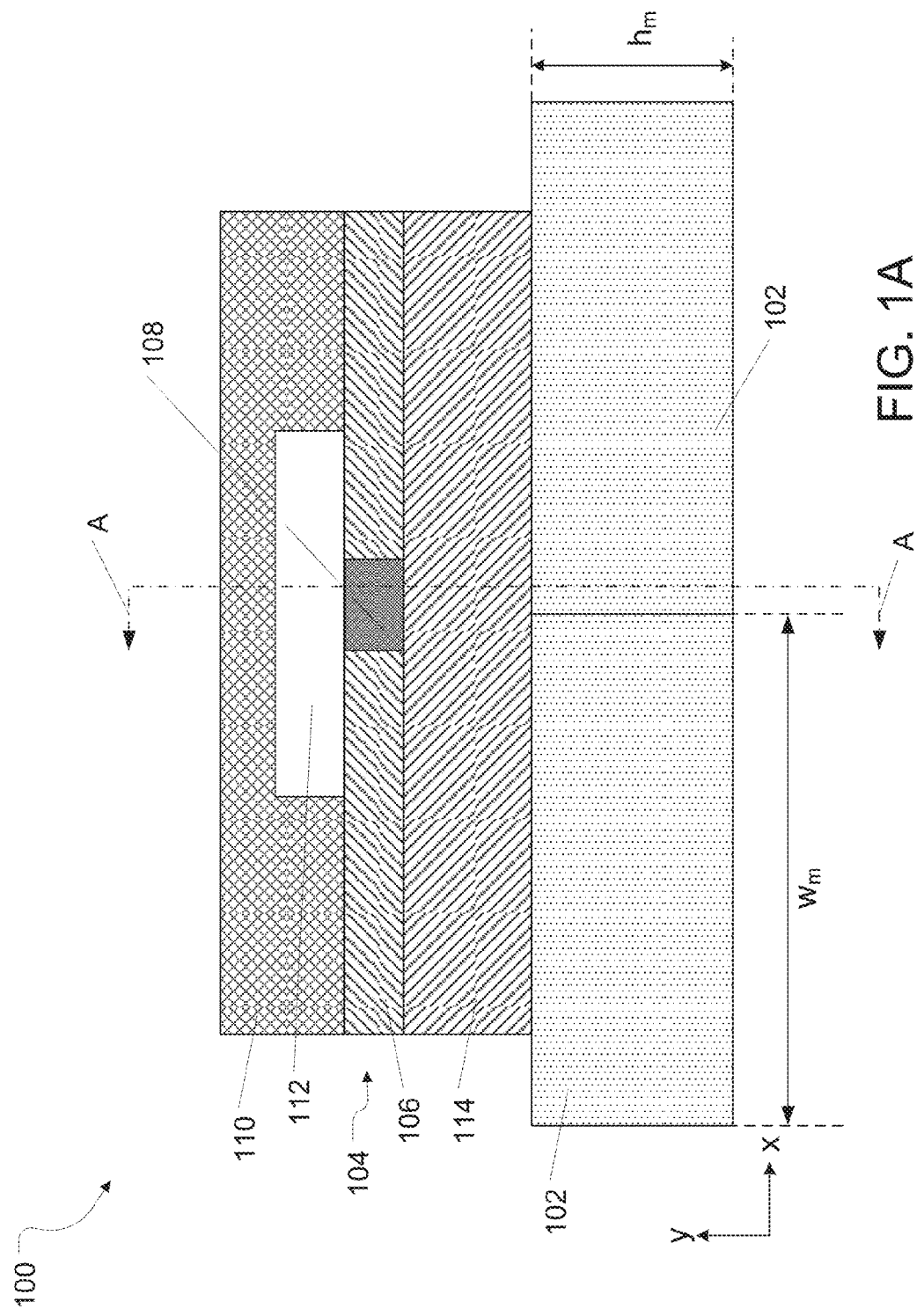

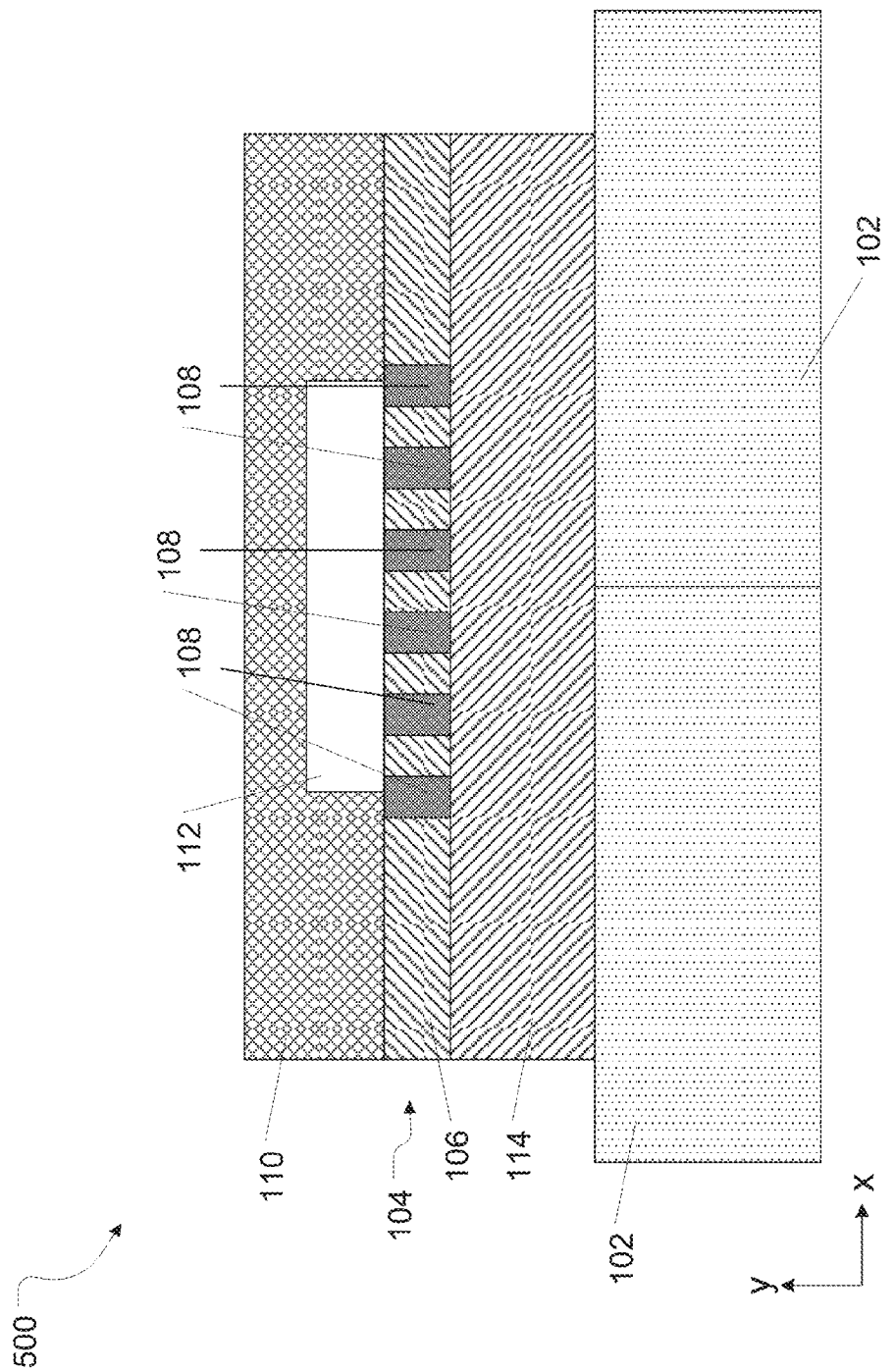

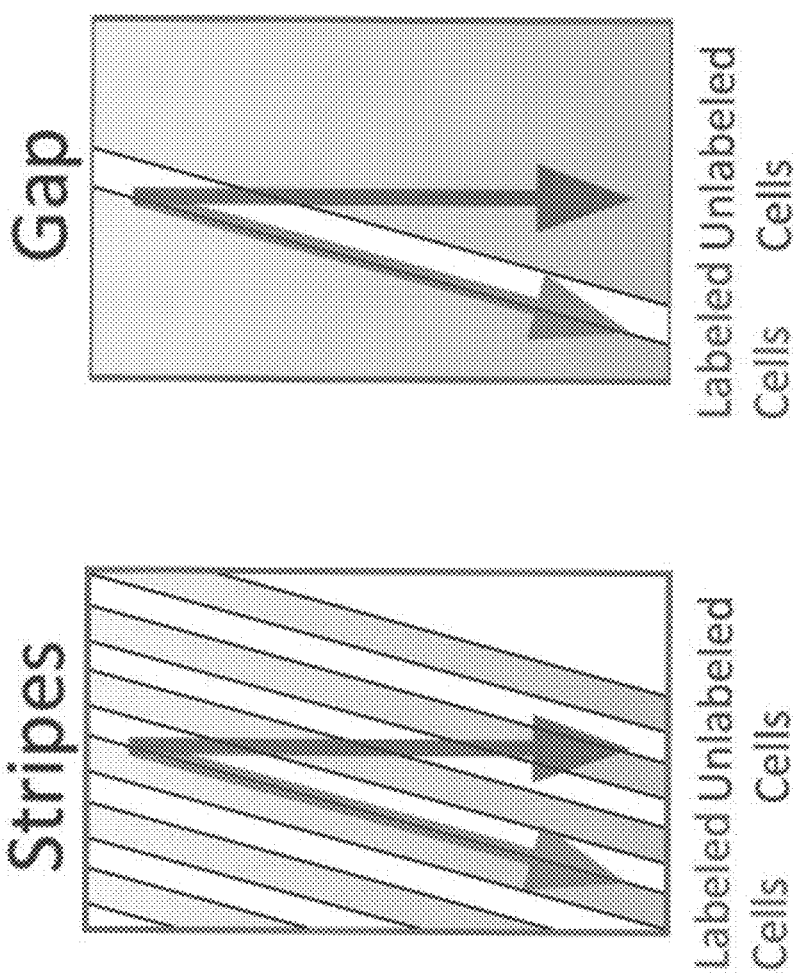

Alternative Magnet Configurations

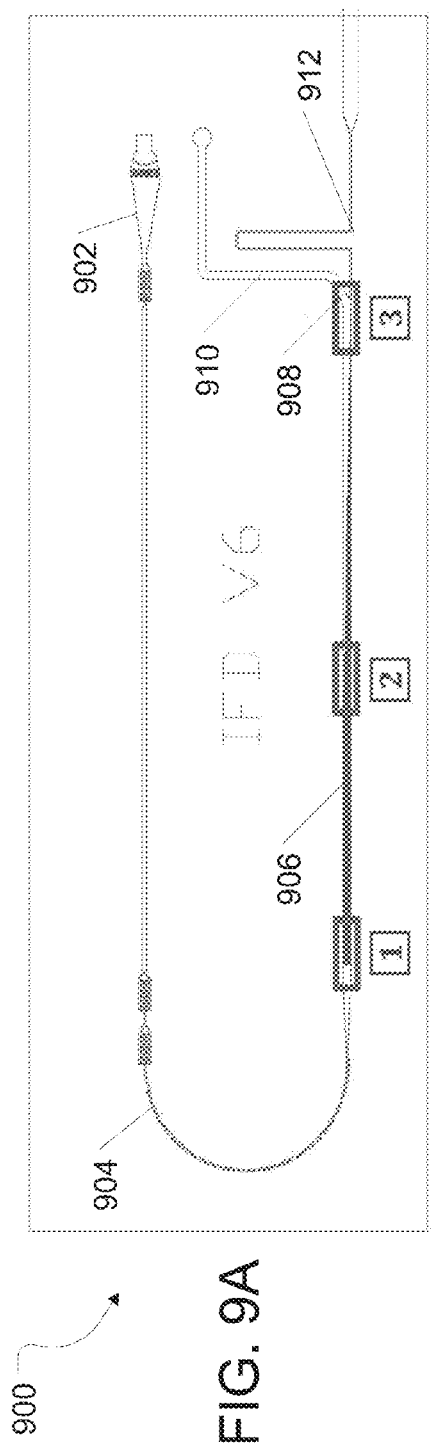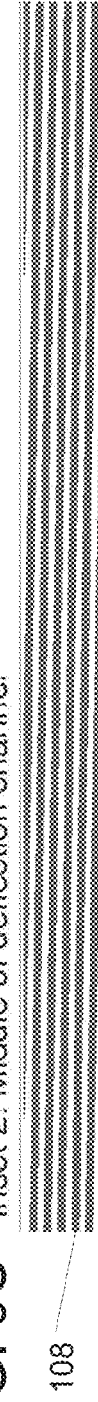
FIG. 9A
FIG. 9B  Inset 1: Beginning of deflection channel
FIG. 9C  Inset 2: Middle of deflection channel
FIG. 9D  Inset 3: End of deflection channel

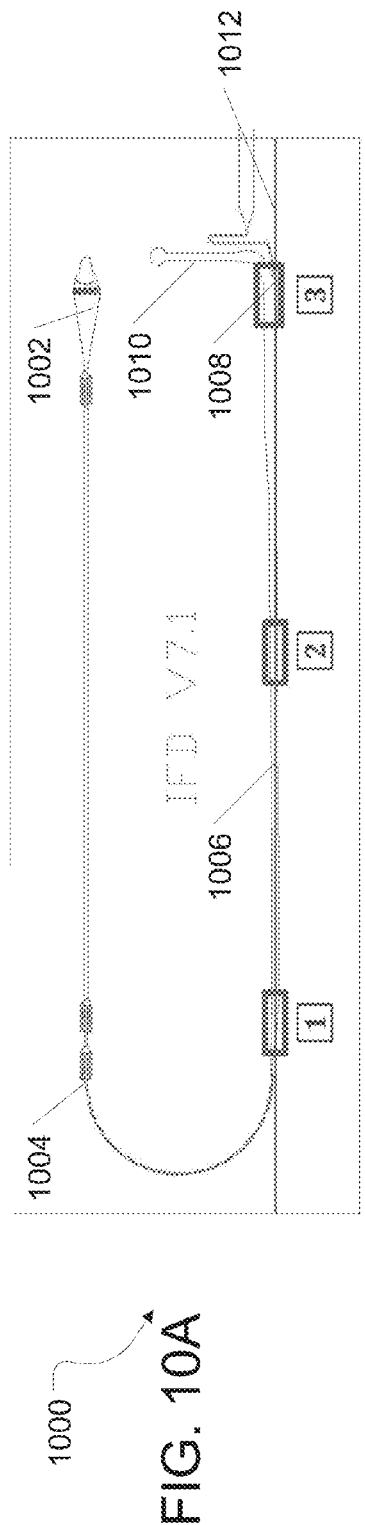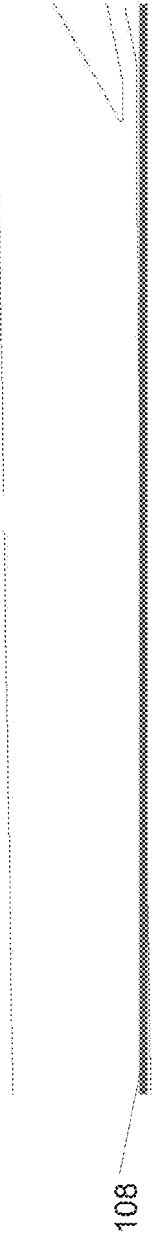
FIG. 10A
FIG. 10B — Inset 1: Beginning of deflection channel
FIG. 10C — Inset 2: Middle of deflection channel
FIG. 10D — Inset 3: End of deflection channel

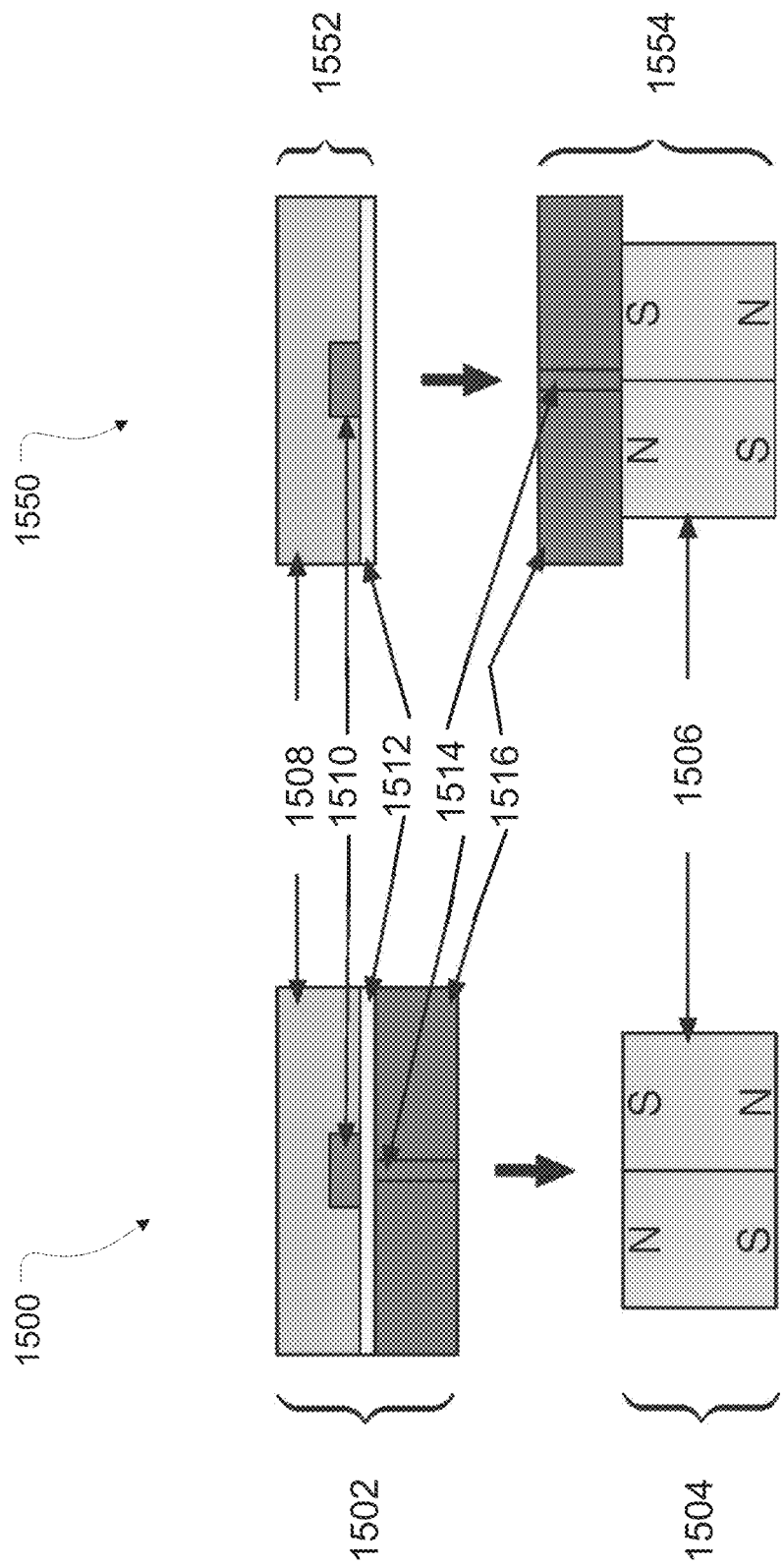

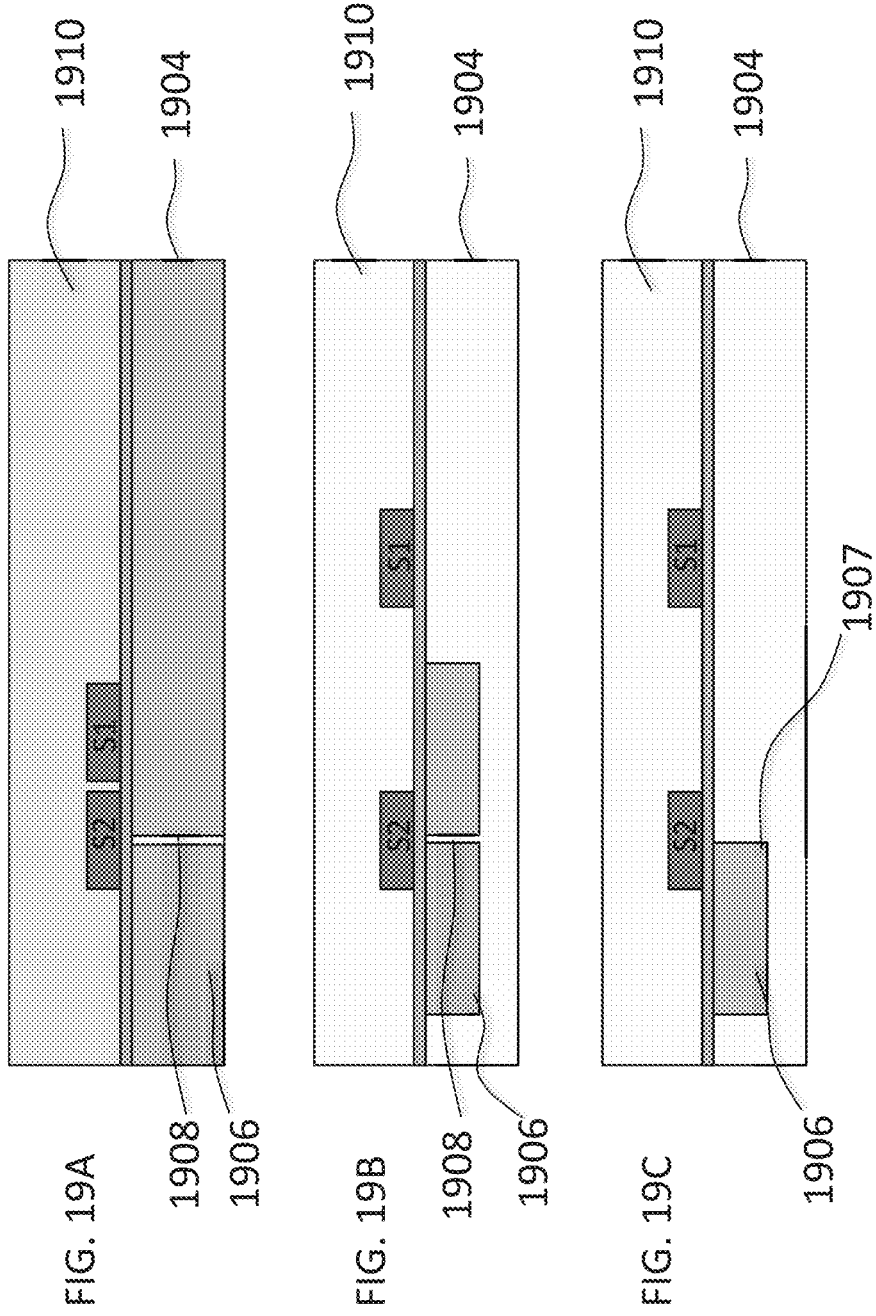

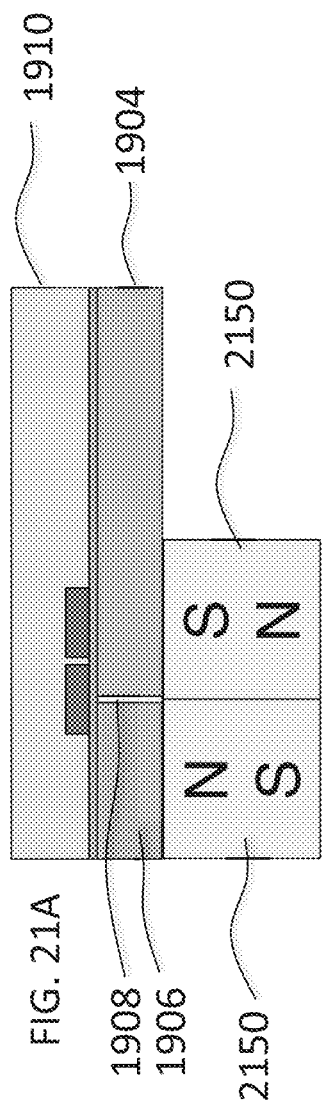
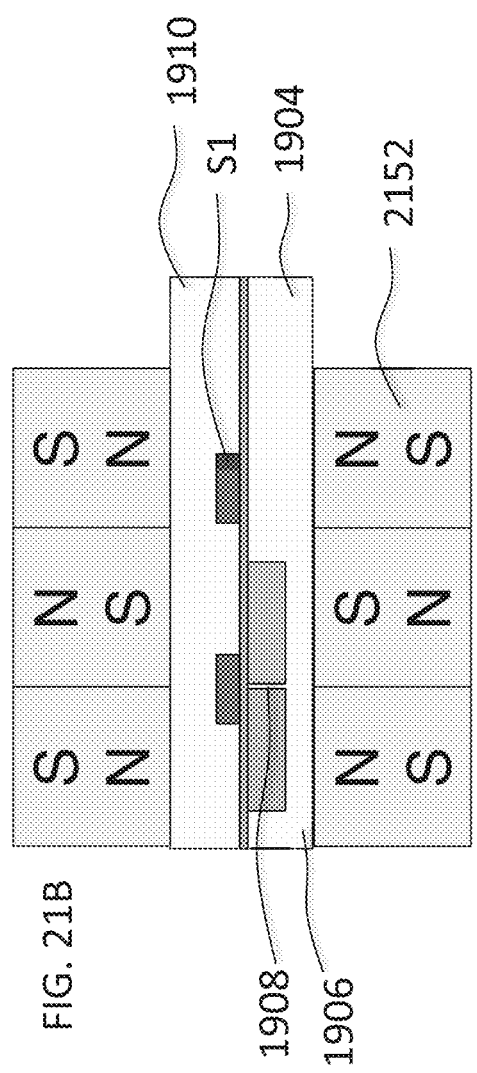

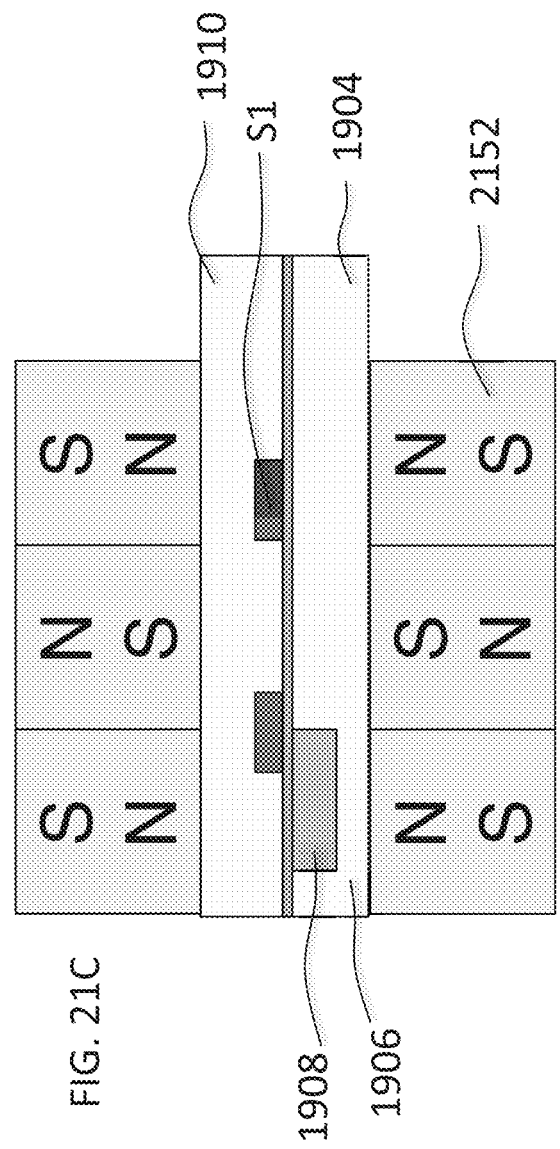

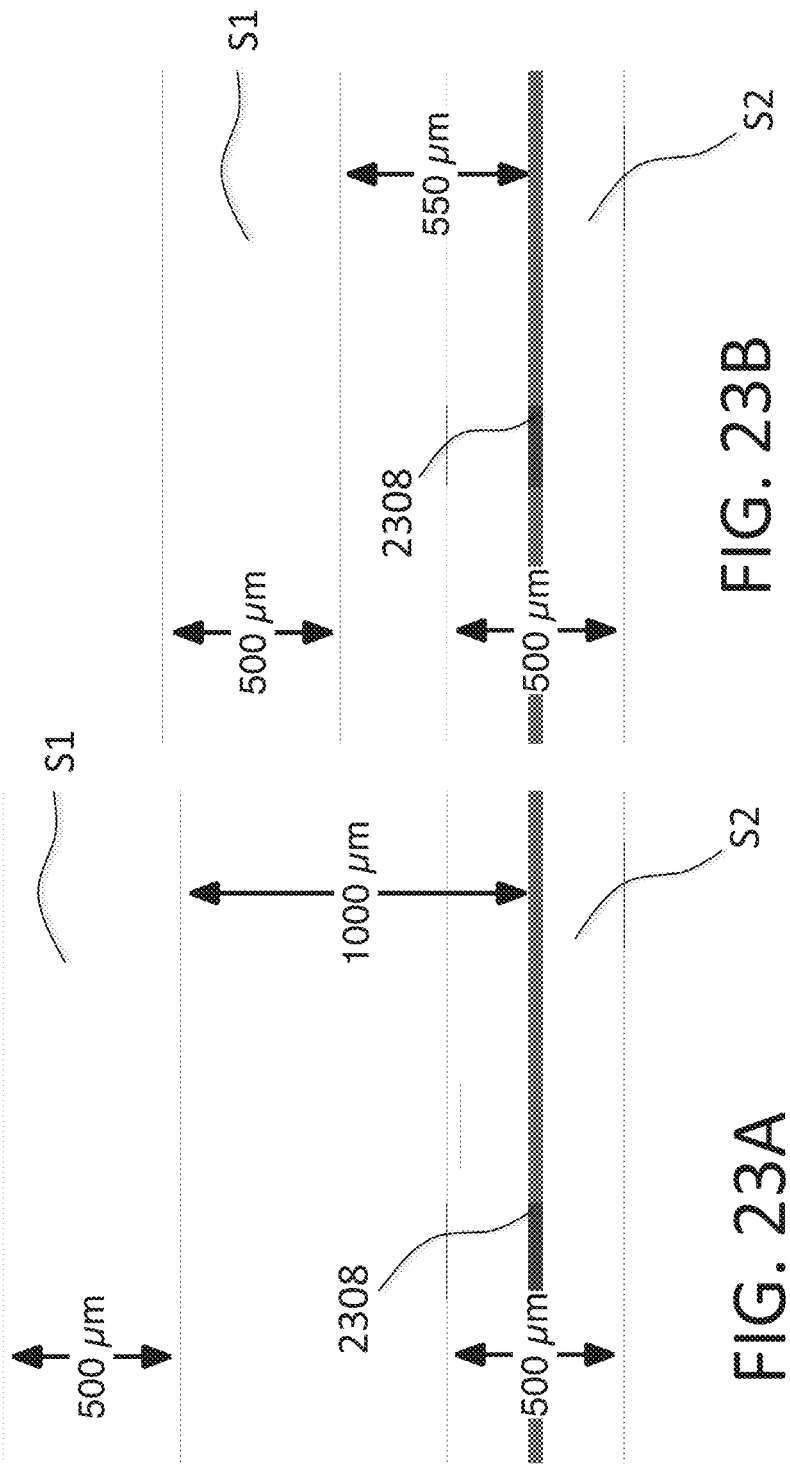

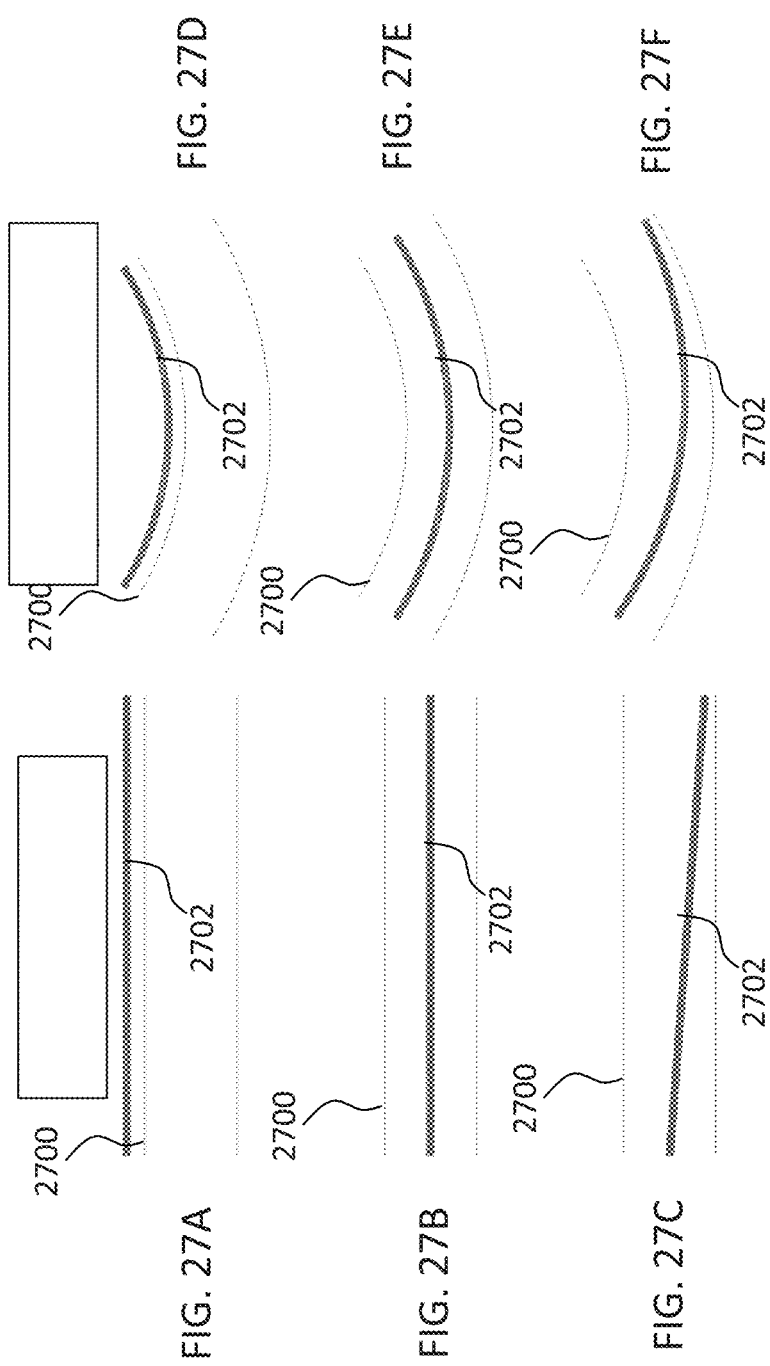

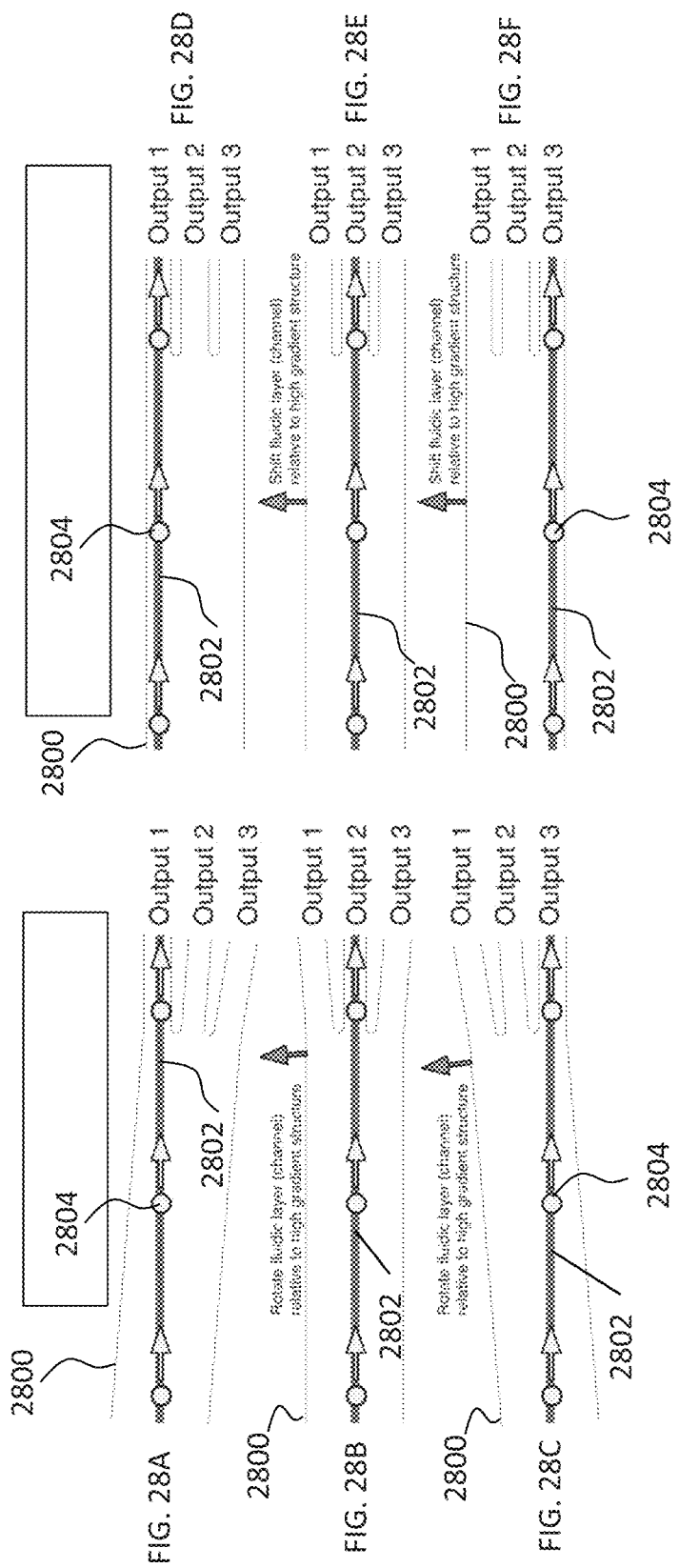

_US 9,878,327 B2_

SORTING PARTICLES USING HIGH GRADIENT MAGNETIC FIELDS

CROSS-REFERENCE TO RELATED APPLICATIONS

This application is a continuation of U.S. application Ser. No. 14/410,985, filed Dec. 23, 2014, which is a 371 U.S. National Application of PCT Application No. PCT/US2013/047710, filed on Jun. 25, 2013, which claims priority to U.S. Provisional Application No. 61/664,051, filed on Jun. 25, 2012. The entire contents of the above applications are incorporated herein by reference.

FIELD OF THE INVENTION

The present disclosure relates to sorting particles using high gradient magnetic fields.

BACKGROUND

Magnetic cell separation is a technique in which magnetic fields are used to isolate cells within a fluid sample. Typically, magnetic particles are selectively attached to one or more desired cells using antibodies that bind to the cell surface. Cells having the attached magnetic particles then can be confined or deflected using an applied magnetic field to isolate the magnetically labeled cells from other analytes in the fluid sample.

SUMMARY

In general, one aspect of the present disclosure can be embodied in microfluidic devices that employ high magnetic field gradients for sorting particles flowing within a microfluidic channel of the device. The devices can include one or more magnets and a layer having a high magnetic permeability region surrounding a low magnetic permeability region. The high magnetic permeability region provides a preferred path for flux lines emanating from the one or more magnets, such that the magnetic field lines extend over the low magnetic permeability region to establish a fringing flux field with a high field gradient. The high field gradient, which is at least about $10^3$ T/m at a distance of at least 20 μm from the channel floor, then can be used to establish a magnetic force on magnetic particles flowing within the adjacent microfluidic channel for sorting.

In accordance with a general aspect 1 of the disclosure, microfluidic devices are provided that include one or more magnets, each magnet being operable to emit a magnetic field; a magnetizable layer adjacent to the one or more magnets, in which the magnetizable layer is configured to induce a gradient in the magnetic field of at least one of the magnets, the gradient being at least $10^3$ T/m at a position that is at least 20 μm away from a surface of the magnetizable layer, and in which the magnetizable layer includes a first high magnetic permeability material, and a low magnetic permeability material arranged adjacent to the high magnetic permeability material; and a microfluidic channel arranged on a surface of the magnetizable layer, wherein a central longitudinal axis of the microfluidic channel is arranged at an angle to or laterally offset from an interface between the high magnetic permeability material and the low magnetic permeability material.

The foregoing and other embodiments can each optionally include one or more of the following features, alone or in combination. For example, in aspect 2 according to aspect 1, the high magnetic permeability material and the low magnetic permeability material are elongated. In aspect 3, according to any one of aspect 2 to 3, the device further includes a second high magnetic permeability material arranged at a distance from the first high magnetic permeability material to form a gap between them (e.g., a uniform gap), wherein the gap is filled with low magnetic permeability material. In aspect 4, according to aspect 3, the low magnetic permeability material in the gap is the same as the low magnetic permeability material in a remainder of the magnetizable layer.

In aspect 5, according to any one of aspects 1 to 4, the gradient can be at least $10^4$ T/m at a position of at least 20 μm away from the surface of the magnetizable layer, e.g., at least $10^4$ T/m at a position of at least 50 μm away from the surface of the magnetizable layer.

In aspect 6, according to any one of aspects 1 to 5, a thickness of the high magnetic permeability material is greater than or equal to approximately 10 μm, e.g., greater than or equal to approximately 100 μm, or greater than or equal to approximately 1 mm.

In aspect 7, according to any one of aspects 1 to 6, a saturation flux density of the high magnetic permeability material is greater than 1 T, e.g., greater than 1.5 T. In aspect 8, according to any one of aspects 1 to 6, the saturation flux density can be about 1.8 T.

In aspect 9, according to any one of aspects 1 to 8, the microfluidic devices include a low magnetic permeability spacer layer between the one or more magnets and the magnetizable layer.

In aspect 10, according to any one of aspects 3 to 9, a thickness of the gap is equal to or less than a thickness of each of the first and second high magnetic permeability material.

In aspect 11, according to any one of aspects 1 to 10, the angle is an oblique angle, e.g., an acute angle, such as an angle of from about 0.5° to about 30°, e.g., 1°, 2°, 3°, 5°, 10, 15°, 20°, or 25° measured from a longitudinal axis of the microfluidic channel of the device.

In aspect 12, according to any one of aspects 1 to 11, the high magnetic permeability material includes iron. In aspect 13, according to any one of aspects 1 to 12, the high magnetic permeability material is selected from the group including or consisting of iron, nickel, cobalt, Nickel-Iron alloy, SiFe alloy, FeAlN alloy, a CoFe alloy, CoFeNi, steel, a polymer composite containing magnetic particles, a glass composite containing magnetic particles, and a ceramic composite containing magnetic particles.

In aspect 14, according to any one of aspects 1 to 13, the microfluidic device includes an elongated cover defining a top surface and side surfaces of the microfluidic channel.

In aspect 15, according to any one of aspects 1 to 14, the low magnetic permeability material can be a non-magnetic material such as a polymer or air.

In aspect 16, according to any one of aspects 1 to 15, the microfluidic device includes a passivation layer arranged on the surface of the magnetizable layer and forming a bottom surface of the microfluidic channel.

In aspect 17, according to any one of aspects 1 to 16, a width of the low magnetic permeability material can narrow from a first side of the magnetizable layer to a second opposite side of the magnetizable layer.

In aspect 18, according to any one of aspects 1 to 17, the microfluidic devices include an array of two or more magnets, each magnet having a magnetic pole orientation that is opposite to a magnetic pole orientation of an adjacent magnet in the array such that the magnetic field of each magnet in the array extends to an adjacent magnet in the array. In aspect 19, according to aspect 18, the elongated low magnetic permeability material can be substantially aligned with an interface between two adjacent magnets of the array.

In aspect 20, according to aspects 1 to 19, the microfluidic devices include a deflection channel and, an output channel separate from the deflection channel, in which both the output channel and the deflection channel are fluidly coupled to an outlet of the microfluidic channel.

In aspect 21, according to aspects 1 to 20, the magnetizable layer can include multiple pieces of elongated low magnetic permeability material, each piece of low magnetic permeability material being arranged within a corresponding elongated gap in the high magnetic permeability material. In aspect 22, according to aspect 21, the multiple elongated gaps can be arranged in parallel. In aspect 23, according to any one of aspects 21 to 22, a thickness of at least one gap can extend completely through a thickness of the high magnetic permeability material. In aspect 24, according to any one of aspects 21 to 23, for one or more of the pieces of low magnetic permeability material, a width of each of the one or more pieces narrows along the central longitudinal axis associated with the corresponding piece.

In accordance with another general aspect 25 of the disclosure, there are provided microfluidic devices that include one or more magnets, each magnet being operable to emit a magnetic field; a magnetizable layer arranged on a surface of the one or more magnets, in which the magnetizable layer includes a high magnetic permeability material and a low magnetic permeability material adjacent to or at least partially bordering the high magnetic permeability material, in which a thickness of the high magnetic permeability material is greater than 10 µm and a saturation flux density of the high magnetic permeability material is greater than 0.2 T, in which the magnetizable layer is configured to induce a gradient in the magnetic field of at least one of the magnets; and
a microfluidic channel arranged on a surface of the magnetizable layer, in which a central longitudinal axis of the microfluidic channel is arranged at an angle to or laterally offset from a an interface between the low magnetic permeability material and the high magnetic permeability material.

In aspect 26 according to aspect 25, the devices further include a deflection channel, and an output channel separate from the deflection channel, in which both the output channel and the deflection channel are fluidly coupled to an outlet of the microfluidic channel.

In accordance with another general aspect 27 of the disclosure, there are provided methods of sorting a target analyte using the microfluidic devices of any one of aspects 20 to 24, and 26, in which the methods include flowing a fluid sample through the microfluidic channel, the fluid sample including the target analyte and one or more magnetic particles bound to the target analyte; exposing, during operation of the microfluidic device, the fluid sample to the gradient in the magnetic field, in which the gradient in the magnetic field deflects the target analyte toward the channel away from an initial fluid flow trajectory of the fluid sample; and collecting the target analyte at an output of the deflection channel.

The foregoing and other embodiments can each optionally include one or more of the following features, alone or in combination. For example, in aspect 28, according to aspect 27, the one or more magnetic particles can include or be selected from the group consisting of superparamagnetic beads, diamagnetic beads, ferromagnetic beads, and combinations thereof. In aspect 29, according to any one of aspects 27 to 28, a ratio of a size of the target analyte to a number of magnetic particles bound to the target analyte can be greater than approximately 10 µm, or greater than approximately 15 µm, or greater than approximately 20 µm, or greater than approximately 25 µm. In aspect 30, according to any one of aspects 27 to 29, one or more magnetic particles can have diameters less than or equal to approximately 0.5 µm, or less than or equal to approximately 0.1 µm. In aspect 31, according to any one of aspects 27 to 30, one or more magnetic particles have magnetic moments less than or equal to approximately 35 kA/m.

In aspect 32, according to any one of aspects 27 to 31, the methods further include cycling the magnetic field on and off.

In accordance with another general aspect 33 of the present disclosure, there are provided methods of fabricating microfluidic devices, in which the methods include providing one or more magnets, each magnet being operable to emit a magnetic field; forming a magnetizable layer adjacent to the one or more magnets, in which the magnetizable layer is configured to induce a gradient in the magnetic field of at least one of the magnets, the gradient being at least $10^3$ T/m at a position that is at least 20 µm away from a surface of the magnetizable layer; and forming a microfluidic channel on a surface of the magnetizable layer.

The foregoing and other embodiments can each optionally include one or more of the following features, alone or in combination. For example, in aspect 34, according to aspect 33, forming the magnetizable layer includes providing a layer of high magnetic permeability material and forming one or more elongated gaps in the high magnetic permeability material. In aspect 35, according to aspect 34, providing the layer of high magnetic permeability material can include casting the layer of high magnetic permeability material, molding the layer of high magnetic permeability material, thermoforming the layer of high magnetic permeability material, or depositing the layer of high magnetic permeability material using sputtering, thermal deposition, plasma deposition, electro-plating or electron-beam deposition. In aspect 36, according to aspect 34, providing the layer of high magnetic permeability material can include placing magnetic tape on a surface of the one or more magnets. In aspect 37, according to any one of aspects 34 to 36, forming the one or more elongated gaps can include machining the layer of high magnetic permeability material. In aspect 38, according to aspect 37, the method further includes machining through an entire thickness of the layer of high magnetic permeability material.

In aspect 39, according to any one of aspects 34 to 38, the methods further include filling the one or more elongated gaps with a low magnetic permeability material, e.g., a non-magnetic material, e.g., filling the one or more elongated gaps comprises using injection molding of the low magnetic permeability material or hot embossing of the low magnetic permeability material.

In aspect 40, according to any one of aspects 34 to 39, the methods include arranging a central longitudinal axis of the microfluidic channel at an angle with respect to at least one of the elongated gaps.

In aspect 41, according to any one of aspects 34 to 40, the methods further include placing a low magnetic permeability substrate, e.g., a non-magnetic substrate, on a surface of the one or more magnets, and forming the magnetizable layer on a surface of the low magnetic permeability substrate, e.g., the non-magnetic substrate.

In accordance with another general aspect 42 of the present disclosure, there are provided microfluidic devices that include one or more magnets, each magnet being operable to emit a magnetic field; a magnetizable layer adjacent to the one or more magnets, the magnetizable layer including a first high magnetic permeability portion and at least one low magnetic permeability portion; and a microfluidic channel adjacent to the magnetizable layer, in which the microfluidic channel includes a first analyte isolation region, and a second analyte isolation region fluidly coupled to the first analyte isolation region, in which the magnetizable layer is configured to induce a gradient in the magnetic field of at least one of the magnets, in which the magnetic field gradient induced in the first analyte isolation region is different from the magnetic field gradient induced in the second analyte isolation region, and in which the magnetic field gradients induced in at least one of the first analyte isolation region and the second analyte isolation region is at least $10^3$ T/m at a position that is at least 20 μm away from a surface of the magnetizable layer.

In accordance with another general aspect 43 of the present disclosure, there are provided microfluidic cartridges that include a magnetizable layer, the magnetizable layer comprising a high magnetic permeability material and a low magnetic permeability material adjacent to or at least partially bordering the high magnetic permeability material; a microfluidic channel arranged on a surface of the magnetizable layer, in which a central longitudinal axis of the microfluidic channel is arranged at an angle to or laterally offset from an interface between the high magnetic permeability material and the low magnetic permeability material; and a passivation layer arranged on the surface of the magnetizable layer and forming a bottom surface to the microfluidic channel, in which a surface of the magnetizable layer is configured to be removably secured to a one or more magnets.

In aspect 44, according to aspect 43, the surface of the magnetizable layer includes protruding structures configured to be removably locked into corresponding sections of the one or more magnets.

In aspect 45, according to any one of aspects 43 to 44, wherein a central longitudinal axis of the microfluidic channel is arranged at an angle to or laterally offset from a an interface between the low magnetic permeability material and the high magnetic permeability material.

In aspect 46, according to any one of aspects 43 to 45, the low magnetic permeability material is arranged within a gap in the high magnetic permeability material or between separate pieces of the high magnetic permeability material.

In aspect 47, according to any one of aspects 43 to 46, a first surface of the high magnetic permeability material and a first surface of the low magnetic permeability material are in direct contact with the passivation layer, and a thickness of the low magnetic permeability material as measured from the passivation layer is greater than a thickness of the high magnetic permeability material.

In accordance with another general aspect 48 of the present disclosure, there are provided microfluidic instruments that include one or more magnets, each magnet being operable to emit a magnetic field; and a magnetizable layer arranged adjacent to the one or more magnets, wherein the magnetizable layer is configured to induce a gradient in the magnetic field of at least one of the magnets, and wherein the magnetizable layer comprises a high magnetic permeability material, and a low magnetic permeability material adjacent to or at least partially bordering the high magnetic permeability material, wherein a surface of the magnetizable layer is configured to be removably secured to a microfluidic cartridge.

In aspect 49 according to aspect 48, the surface of the magnetizable layer comprises protruding structures configured to be removably locked into corresponding sections of the microfluidic cartridge.

In aspect 50, according to any one of aspects 48 to 49, the low magnetic permeability material is arranged within a gap in the high magnetic permeability material or between separate pieces of the high magnetic permeability material.

In aspect 51, according to any one of aspects 48 to 50, a first surface of the high magnetic permeability material and a first surface of the low magnetic permeability material form the surface of the magnetizable layer, and wherein a thickness of the low magnetic permeability material as measured from the surface of the magnetizable layer is greater than a thickness of the high magnetic permeability material.

In accordance with another general aspect 52 of the present disclosure, there are provided methods of sorting a target analyte using the microfluidic devices or the microfluidic cartridges of any one of aspects 1 to 26 and 42-47. The methods include flowing a fluid sample through the microfluidic channel, the fluid sample comprising the target analyte and one or more magnetic particles bound to the target analyte; exposing, during operation of the microfluidic device or the microfluidic cartridge, the fluid sample to the gradient in the magnetic field, wherein the gradient in the magnetic field deflects a trajectory of the target analyte away from an initial fluid flow trajectory of the fluid sample.

In aspect 53 according to aspect 52, the gradient in the magnetic field exerts a force on the target analyte in a first direction toward the magnetizable layer. In aspect 54, according to aspect 53, the gradient in the magnetic field also exerts a force on the target analyte in a second direction different from the first direction. In aspect 55, according to aspect 3, a width of the gap is equal to or greater than approximately 100 nm, e.g., equal to or greater than approximately 500 nm, equal to or greater than approximately 1 μm, equal to or greater than approximately 10 μm, equal to or greater than approximately 50 μm, equal to or greater than approximately 75 μm, or equal to or greater than approximately 100 μm.

In aspect 56 according to any one of aspects 1 to 26 and 42-51, the microfluidic channel is curved. In aspect 57, according to any one of aspects 1 to 26, 42-51, and 56, a boundary between the high magnetic permeability material and the low magnetic permeability material is curved. In aspect 58, according to any one of aspects 48-51, the instrument is configured to be removably fixed to the microfluidic cartridge to any one of a plurality of different orientations with respect to the microfluidic cartridge.

In aspect 59, according to any one of aspects 1 to 58, the high magnetic permeability material has a relative permeability that is greater than the relative permeability of the lower magnetic permeability material by at least about 4. In aspect 60, according to any one of aspects 1 to 59, the high magnetic permeability material has a relative permeability that is at least about 5.

As used herein, "linked" means attached or bound by covalent bonds, noncovalent bonds, or other bonds, such as van der Waals forces.

As used herein, "specifically binds" means that one molecule, such as a binding moiety, e.g., an oligonucleotide or an antibody, binds preferentially to another molecule, such as a target molecule, e.g., a nucleic acid or protein, e.g., a cell surface marker, in the presence of other molecules in a sample.

As used herein, "magnetic moment" is the tendency of a magnetic material to align with a magnetic field.

As used herein, "saturation flux density" is the magnetic flux density of a material when the material is fully magnetized, i.e., when there is a negligible increase in the flux density with further increases in a magnetizing field.

As used herein, "magnetizable" is understood to mean capable of being magnetized.

Unless otherwise defined, all technical and scientific terms used herein have the same meaning as commonly understood by one of ordinary skill in the art to which this invention belongs. Although methods, materials, and devices similar or equivalent to those described herein can be used in the practice or testing of the present invention, suitable methods, materials and devices are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 1A is a cross-sectional view of an example of a microfluidic device as described herein.

FIG. 5A is a cross-sectional view of an example of a microfluidic device having a magnetizable layer in which multiple low magnetic permeability regions are formed and arranged in parallel.

FIG. 5C is a schematic of the flow of labeled and unlabeled cells in a microfluidic design that includes multiple parallel low magnetic permeability regions.

FIG. 5D is a schematic of the flow of labeled and unlabeled cells in a microfluidic design that includes a single low magnetic permeability region.

FIGS. 9A-9D are schematics of an example of a system that includes a microfluidic device for isolating and/or sorting target analytes based on high magnetic flux gradients.

FIGS. 10A-10D are schematics of an example of a system that includes a microfluidic device as described herein for isolating and/or sorting target analytes based on high magnetic flux gradients.

FIG. 14A is a schematic of a first configuration of an example of a microfluidic device that includes a removable and/or replaceable portion.

FIG. 14B is a schematic of a second configuration of an example of a microfluidic device that includes a removable and/or replaceable portion.

FIGS. 19A-19C are schematics showing cross-sections of three different example configurations of a magnetizable layer.

FIGS. 21A-21C are schematics of different examples of configurations for the arrangement of magnets in an integrated microfluidic device.

FIGS. 23A-23B are each a schematic depicting a top view of a first and second stage of an integrated microfluidic device.

FIGS. 27A-27F are schematics depicting top views of examples of different microfluidic channel designs and high magnetic flux gradient inducing structures.

FIGS. 28A-28F are schematics depicting top views of examples of different arrangements of a microfluidic channel with respect to a high magnetic flux gradient inducing structure.

DETAILED DESCRIPTION

Figure 1B:
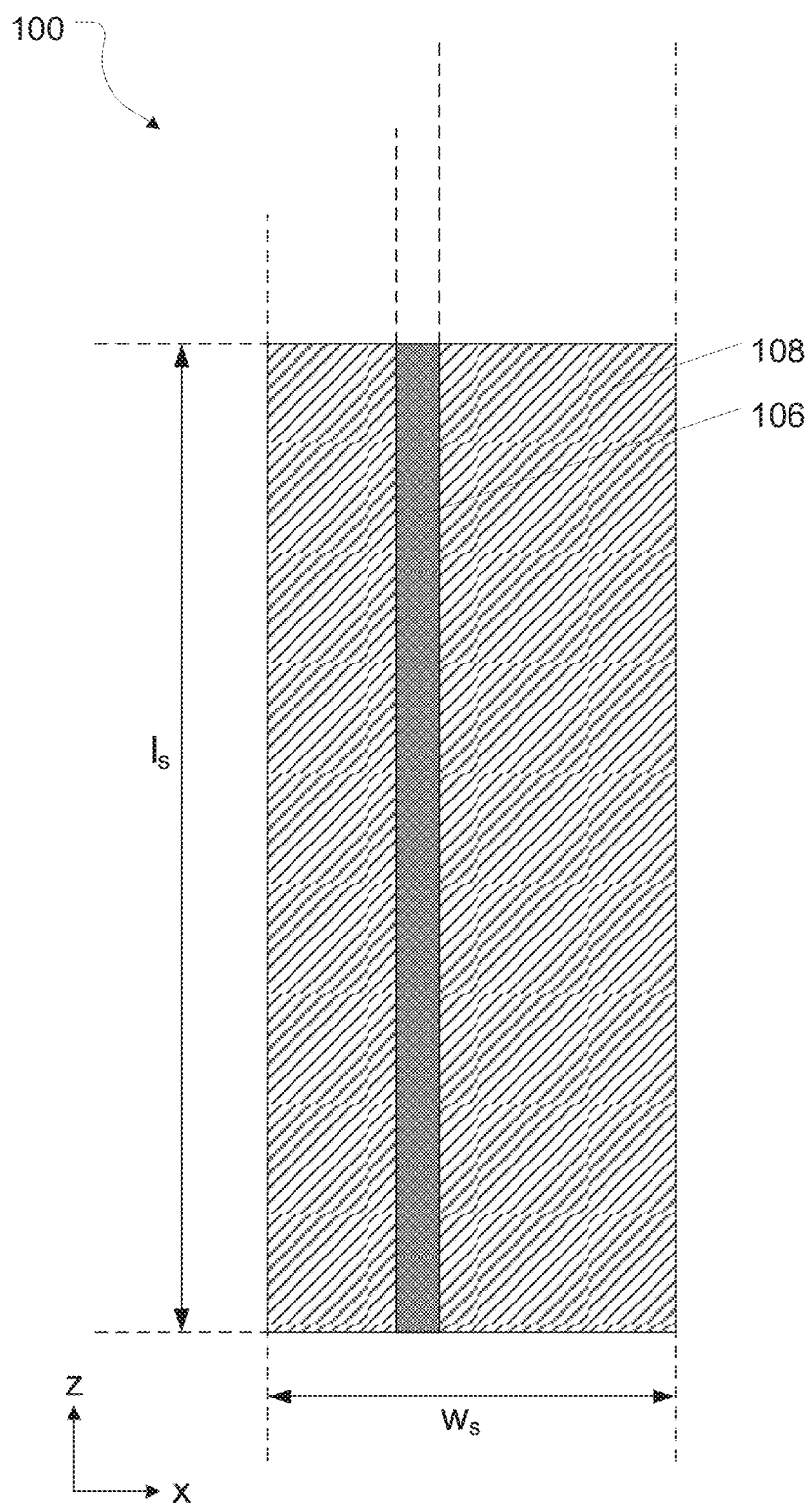
FIG. 1B is a top view of a magnetizable layer of the microfluidic device of FIG. 1A.

The present disclosure relates to methods and systems for sorting particles using high gradient magnetic fields. In general, one aspect of the present disclosure can be embodied in microfluidic devices that employ high magnetic field gradients for sorting target agents or analytes (e.g., nucleic acids, polypeptides, bacteria, cells) flowing within a microfluidic channel of the device. The devices can include one or more magnets and a layer having one or more high magnetic permeability regions adjacent to or at least partially bordering a low magnetic permeability region. The high magnetic permeability region provides a preferred path for flux lines emanating from the one or more magnets, such that the magnetic field lines extend over the low magnetic permeability region to establish a fringing flux field with a high field gradient. The high field gradient gives rise to a magnetic force that "pulls" the magnetic particles (and the analyte to which the magnetic particles are attached) flowing within the adjacent microfluidic channel toward the gap for sorting.

FIG. 1A is a cross-sectional view of an example of a microfluidic capable of generating high magnetic gradients for isolating target analytes. A Cartesian coordinate system is provided for reference, in which the positive z-direction is into the page. The device 100 includes one or more magnets 102, a magnetizable layer 104, and a microfluidic channel cover 110 that defines a microfluidic channel region 112 through which a sample fluid may flow. The device may optionally include a spacer layer 114 between the one or more magnets 102. The magnetizable layer 104 may be composed of separate portions: a high magnetic permeability portion 106 having a magnetic permeability that is higher relative to an elongated low magnetic permeability portion 108. The high magnetic permeability portion preferably has a relative permeability (the ratio of the permeability of the medium to that of free space permeability) that is greater than the relative permeability of the lower magnetic permeability material by at least about 4. The high magnetic permeability material preferably has a relative permeability of at least 5. During operation of the device 100, a fluid sample may flow through the channel region 112, e.g., along the z-direction.

FIG. 1B is a top view of the magnetizable layer 104 with the cover 110 removed. As shown in FIG. 1B, the elongated low magnetic permeability portion 108 also extends along the z-direction.

One of the principles behind the operation of device 100 is that the magnetizable layer 104 is configured to drive a large magnetic flux into a small region of space, thus giving rise to a high flux density, and therefore a strong magnetic force within the channel region 112. In particular, the high magnetic permeability portion 106 of layer 104 provides the preferred (low reluctance) path for the magnetic flux emanating from the one or more magnets 102. In contrast, the magnetic flux tends to avoid the low magnetic permeability portion 108 located between the high permeability regions 106. In addition, the region above the magnetizable layer 104 (e.g., the microfluidic cover 110 including the channel region 112) preferably also has a low magnetic permeability relative to the portion 106. As a result of the tendency of the magnetic flux to prefer the high magnetic permeability regions, a portion of the flux passes through the surface of the high permeability portion 106 on a first side of the low permeability region 108, through the microfluidic channel 112, and then back into the high permeability portion 106 on a second opposite side of the low permeability region 108. The portion of the flux extending into the microfluidic channel 112 is the "fringing" or "leakage" flux (field).

The magnitude of the fringing flux that extends into the channel 112 is very large close to the surface of the magnetizable layer 104, but drops off quickly as the distance from the magnetizable layer surface increases, giving rise to a large flux gradient. The force on a magnetic particle passing through the channel is proportional to the magnitude of $\nabla B$, where $\nabla$ corresponds to the vector differential operator and B is the magnetic flux. The gradient in flux may be largest at the edges between the high magnetic permeability portions 106 and the low magnetic permeability portions 108. Therefore, magnetic particles (and analytes attached to the magnetic particles) that flow through the channel 112 in the region above the low magnetic permeability portion 108 are attracted by the strong magnetic force towards the surface of the magnetizable layer 104. In contrast to a device in which a homogeneous magnetic field extends throughout the fluidic channel, the magnetic field gradient enables, in certain implementations, a greater "pull" on magnetic particles, thus allowing quicker isolation of magnetically labeled analytes from other analytes in the fluid sample. As a result, higher sample fluid velocities and/or shorter fluidic channels lengths can be used for separating the target analytes.

Figure 1C:
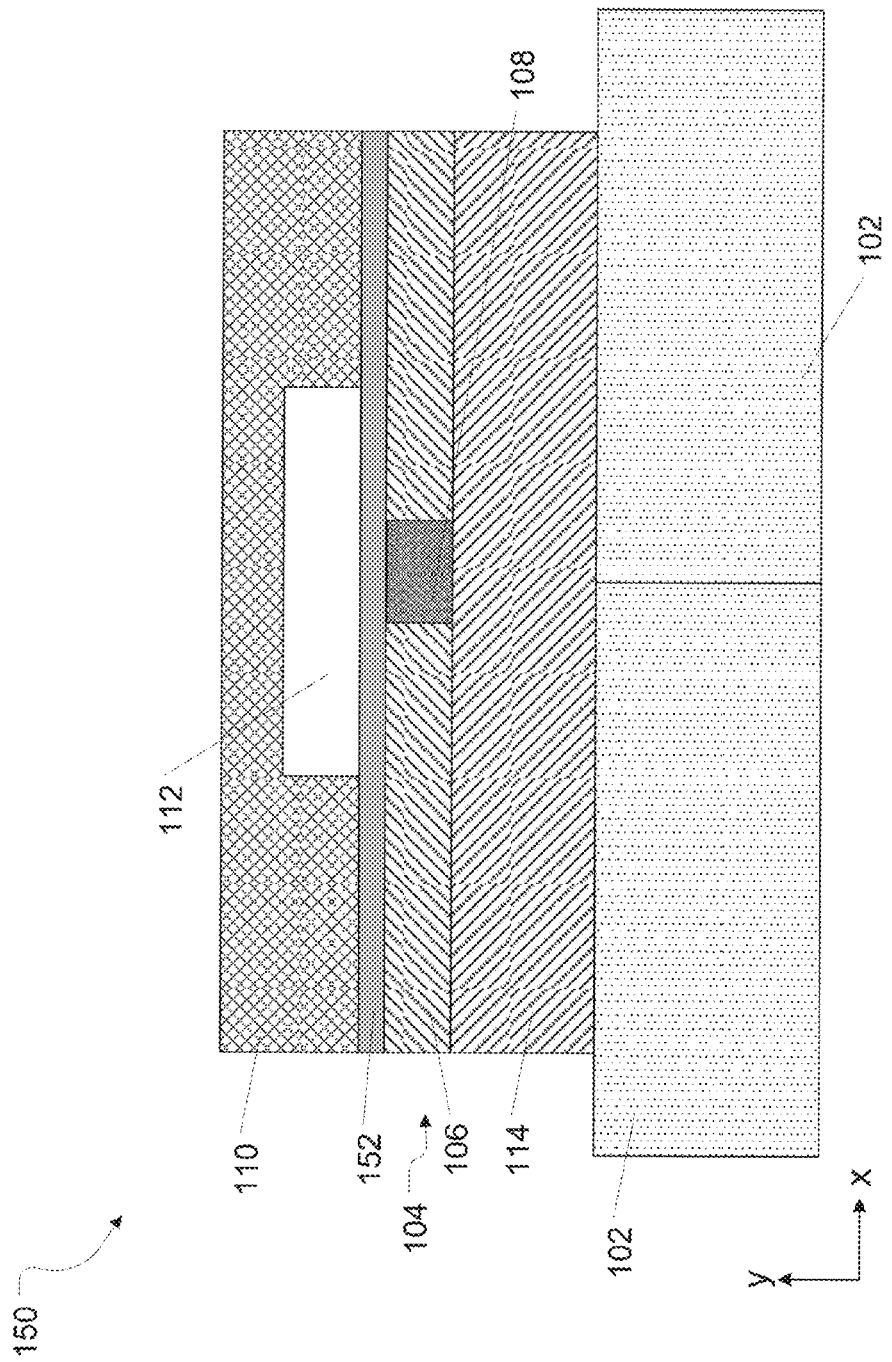
FIG. 1C is a cross-sectional view of an example of a microfluidic device that includes a thin-film layer between a magnetizable layer and a microfluidic cover.
Figure 2:
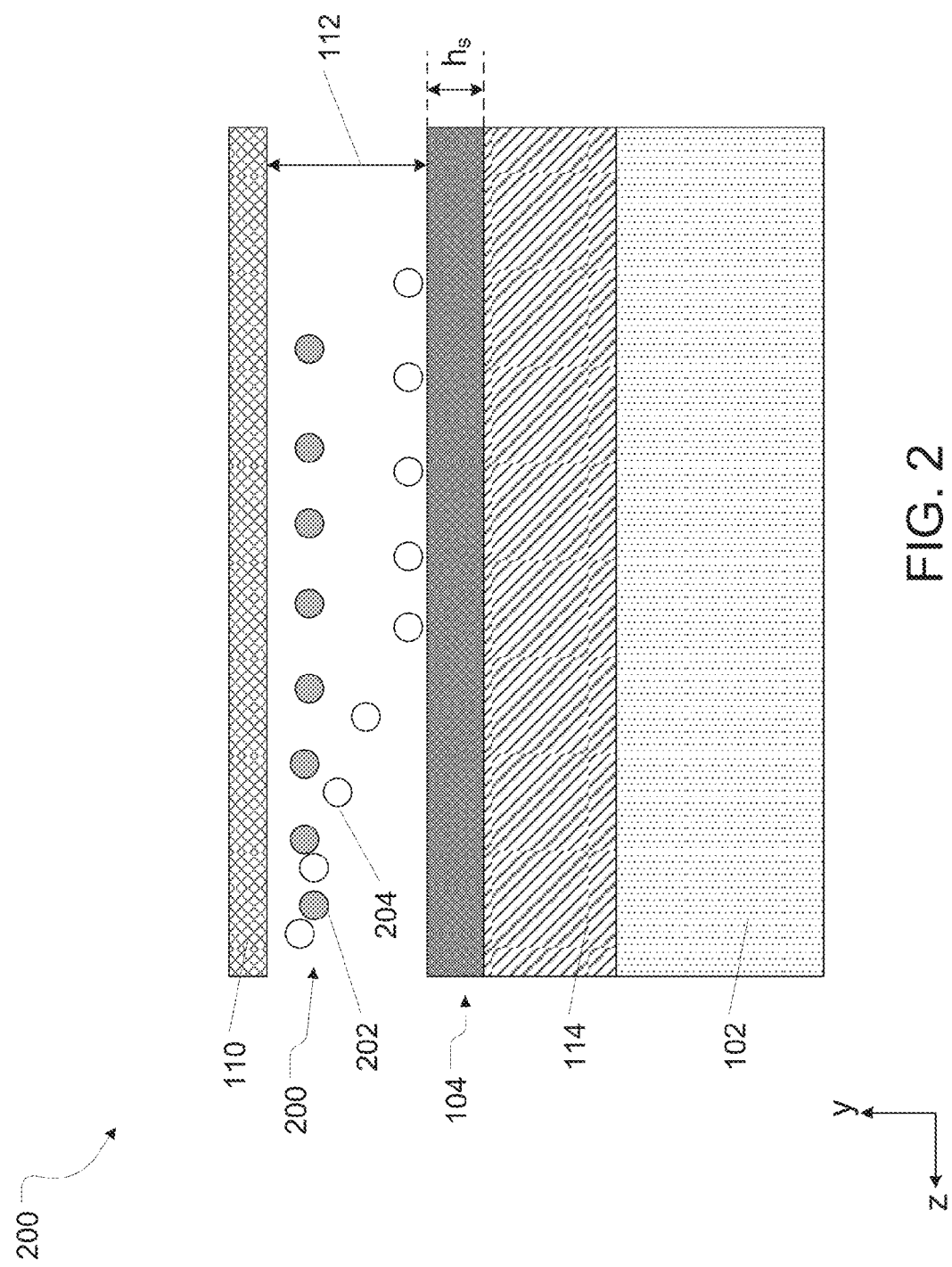
FIG. 2 is a side view of an example of a microfluidic device as described herein.

FIG. 2 is a side view of an example of the device 100 taken at line A-A of FIG. 1. FIG. 2 depicts how magnetic particles can be sorted from a fluid sample 200 using the high magnetic field gradient. A coordinate system is again shown for reference. The fluid sample 200 enters the device 100 from the left (as indicated by the arrow). The sample 200 contains both magnetic particles 202 and non-magnetic particles 204 in a fluid such as water, a buffer, saline, blood (e.g., diluted blood or whole blood), or other applicable fluid. For the present example, the fluid sample 200 follows a pressure-driven laminar flow having a parabolic velocity profile, with the highest fluid velocity at the center of the channel 112 and low fluid velocity near the boundary walls of the channel 112. However, other fluid driving mechanisms, such as electrokinetic techniques, having different velocity profiles can also be used.

As the fluid sample 200 passes over the magnetizable region 104, the high magnetic gradient generated by the device gives rise to a magnetic force that pulls magnetic particles 204 from the sample 200 toward the surface of the region 104. Non-magnetic particles 202 are unaffected by the magnetic force and continue flowing with the sample 200 at approximately the same height in the channel 112. The separation of the magnetic particles 204 from the non-magnetic particles 202 enables independent collection of the magnetic particles and/or analytes attached to the magnetic particles 204.

Referring again to FIG. 1A, the greater the magnetic flux driven through the high permeability region 106, the stronger the magnetic force in the region above the low magnetic permeability region 108 and, therefore, the stronger the force experienced by magnetic particles traveling in the vicinity of the low magnetic permeability region 108. The magnitude of flux can be affected based on one or more parameters of the microfluidic device 100 including, for example, the strength of the magnet(s) that emits the magnetic field. The stronger the magnet used, the greater the flux that can be achieved. The strength of the maximum magnetic field that can be produced from a magnet is denoted using the symbol Br, i.e., the remanent magnetization of the magnet. The types of magnets that may be used include, for example, permanent magnets or electromagnets. The magnets may be composed of material including, for example, alloys of NdFeB, SmCo, AlNiCo, or ferrite. The magnetic field provided by the one or more magnets 102 may be in the range of approximately 0.001 T to approximately 1.5 T. For example, the magnetic field emitted by the one or more magnets 102 may be approximately 0.1 T, approximately 0.3 T, approximately 0.5 T, approximately 1 T, or approximately 1.3 T. Other values for the magnetic field are possible as well.

Another parameter that affects the flux magnitude, and therefore the flux gradient that can be achieved, is the maximum magnetic permeability of region 106, i.e., the saturation flux density Bs. The greater the saturation flux density, the greater the amount of flux that can pass through the region 106 leading to gains in flux gradient. Accordingly, it is preferable that the amount of flux through the high relative magnetic permeability region 106 is at least equal to or greater than the saturation flux density Bs of the material forming region 106. Materials that can be used for the high magnetic permeability region 106 include, but are not limited to, iron, nickel, cobalt, and nickel-iron alloys such as $Ni_{80}Fe_{20}$ or $Ni_{45}Fe_{55}$, steel, CoFeNi, FeAlN alloys, SiFe alloys, or CoFe alloys. The high magnetic permeability materials may have saturation permeabilities that are greater than or equal to approximately 1 T. For example, the high magnetic permeability material may have a saturation flux density that is greater than or equal to approximately 1.2 T, greater than or equal to approximately 1.4 T, greater than or equal to approximately 1.6 T, greater than or equal to approximately 1.8 T, or greater than or equal to approximately 2.0 T.

The parameters Br and Bs may also be used to determine other properties of the microfluidic device 100 that enable achieving high flux gradients above the low magnetic permeability region 108. For example, to a first order approximation, the relationship between remnant magnetization and saturation flux density of the high magnetic permeability region should follow $(Br)w_m \geq (Bs)(hs)$, where $w_m$ is the cross-sectional width of the one or more magnets 102 and hs is the height of the magnetizable layer 104. Thus, the minimum cross-sectional width that should be used to obtain a maximum flux gradient for a particular magnet/high permeability material combination may be expressed as $w_m \geq (Bs/Br)hs$. Examples of cross-sectional width $w_m$ can range from approximately 1 μm to approximately 50 mm, including, for example, approximately 50 μm, approximately 500 μm, approximately 1 mm, approximately 2 mm, approximately 5 mm, or approximately 10 mm. Similarly, a magnet thickness hm approximately equal to the cross-sectional width should be more than sufficient to obtain the maximum flux gradient. Examples of magnet thicknesses are approximately 500 μm, approximately 1 mm, approximately 2 mm, approximately 4 mm, approximately 5 mm, or approximately 10 mm.

A thickness hs of the magnetizable layer 104 may fall within the range of approximately 1 μm to approximately 10 mm. For example, the thickness hs may be approximately 10 μm, approximately 100 μm, approximately 250 μm, approximately 500 μm, approximately 1 mm, or approximately 5 mm. Other thicknesses are possible as well. The thickness of the high magnetic permeability material 106 may be equal to or less than a thickness of the magnetizable layer 104. For example, a thickness of the high magnetic permeability material 106 may be approximately 1 μm, 10 μm, approximately 100 μm, approximately 250 μm, approximately 500 μm, approximately 1 mm, approximately 5 mm, or approximately 10 mm. Other thicknesses for the high magnetic permeability region are possible as well. Preferably, the width ws of the magnetizable layer 104 is sufficient to accommodate the width of the one or more magnets 102 beneath layer 104, as well as the width of the channel 112 above the layer 104, and may fall within the range of approximately 500 μm to approximately 100 mm. For example, the width ws may be approximately 1 mm, approximately 5 mm, approximately 10 mm, approximately 25 mm, approximately 50 mm, or approximately 75 mm. Other widths are possible as well. In some implementations, the width ws may extend beyond 100 mm to accommodate multiplexing in which multiple channels 112 are formed within the device 100, e.g., in parallel or in series.

An appropriate length ls for the magnetizable layer 104 (and, in some cases, the length of the channel region 112 and magnet(s) 102) for isolating target analytes depends on various factors including, among other things, the strength of the magnetic force in the channel region 112, the residence time of analytes within the channel 112, the velocity or flow rate of the fluid sample as it passes through the channel 112, and the responsivity of magnetic particles to the magnetic force in the channel 112. The length ls of the magnetizable layer may fall within the range of approximately 1 mm to approximately 500 mm. For example, the length is may be approximately 5 mm, approximately 10 mm, approximately 50 mm, approximately 100 mm, approximately 250 mm, approximately 500 mm, or approximately 750 mm. Other lengths are possible as well. The length of the high magnetic permeability material 106 may be equal to or less than a length of the magnetizable layer 104. For example, a length of the high magnetic permeability material 106 may be approximately 1 mm, 5 mm, approximately 10 mm, approximately 50 mm, approximately 100 mm, approximately 250 mm, approximately 500 mm, or approximately 750 mm. Other lengths for the high magnetic permeability region are possible as well.

Though the high magnetic permeability region 108 is shown as having a rectangular cross-section in FIG. 1A, other shapes are also possible for region 108. For example, the region can have any number of different cross-sections, e.g., square, circular, triangular, hexagonal, curved, e.g., concave or convex, or oval cross-sections. Other cross-sections are possible. The important aspect is to create an interface between the high magnetic permeability material and the low magnetic permeability material.

Preferably, the low magnetic permeability region 108 has a substantially smaller relative magnetic permeability than that of the high magnetic permeability region 106. For example, the low magnetic permeability material has a relative magnetic permeability that is lower than the relative magnetic permeability of the high magnetic permeability material by at least about 4. Various materials can be used as the low magnetic permeability region 108. For example, the low magnetic permeability portion 108 can include, but is not limited to, polymers (e.g., polyethylene, polyimide, polymethamethacrylate (PMMA), polystyrene, polydimethylsiloxane (PDMS), epoxy), glass, ceramics, metal (e.g., brass), or silicon. The low magnetic permeability material can include non-magnetic materials. The materials to be included in the low magnetic permeability portion 108 are not limited to solid materials and include fluids such as water. In some implementations, portion 108 may correspond to a gap comprising air, a gas (e.g., an inert gas), or a vacuum. The relative magnetic permeability of the portion 108 may range from approximately 1 to approximately 1000. As explained above, the saturation flux of the portion 108 should be less than the saturation flux of the portion 106. Preferably, the difference in saturation flux is about 1 T, though the difference can be greater or less than 1 T.

Preferably, the flux gradient is widely distributed across the width of the channel 112 so that even magnetic particles at a relatively far distance from the surface of the magnetizable layer 104 (e.g., at the top of the channel 112) experience the magnetic force and are "pulled" down toward the layer 104, and more specifically, toward the elongated low magnetic permeability portion 108 where the flux gradient is highest. Preferably, the width of the low magnetic permeability portion 108 is approximately the same size as or larger than the width of the target analyte. For example, for a typical cell of approximately 20 µm, the width of the portion 108 is also approximately 20 µm. The width of the portion 108 may fall within the range of approximately 100 nm to approximately 500 µm. For example, the width of the portion 108 may be approximately 500 nm, approximately 1 µm, approximately 10 µm, approximately 50 µm, or approximately 75 µm. Similarly, the width of the channel region 112 is preferably just as wide or wider than the width of the low magnetic permeability portion 108 to allow desired target analytes to pass through. In addition, the width of the channel region 112 may be wider or narrower than the width of the elongated portion 108.

In some implementations, the width of the low magnetic permeability portion 108 may vary across the length is of the magnetizable layer 104. For example, in some cases, the width of the portion 108 may be tapered from a first side of the magnetizable layer 104 toward a second opposite side of the magnetizable layer 104 along the z-direction. Alternatively, or in addition, the width of the low magnetic permeability portion 108 may vary across the thickness hs of the magnetizable layer 104. For example, in some cases, the width of the portion 108 may be tapered from a top surface of the magnetizable layer 104 near the channel region 112 toward a bottom surface of the magnetizable layer 104 near the optional spacer layer 114 or vice versa. Tapering the width of portion 108 from the base of the magnetizable layer 104 to the top of the magnetizable layer near the channel region 112 may, in some implementations, provide the advantage of a more spatially distributed flux gradient in the channel 112.

In some implementations, the magnetizable layer 104 may be composed of flexible magnetic tape in the form of a strip or foil, in which the tape material is used as the high magnetic permeability material. Flexible magnetic tape offers the advantage, in some cases, of being easy to apply to the one or more magnets 102 or the spacer layer 114. An adhesive may be formed on one side of the magnetic tape for adhering to the one or more magnets 102 or the spacer layer 114. Examples of material that may be used for flexible magnetic tape include, but are not limited to, Master Magnetics magnetic tape (Master Magnetics, Inc.) or Magna Card magnetic tape (Magna Card, Inc.). The low magnetic permeability portion 108 may be formed in the magnetic tape by etching or cutting out a pre-defined region of the magnetic tape.

The microfluidic cover 110 can be formed from any applicable material that is compatible with the fluid sample to be delivered through the microfluidic channel. For example, the microfluidic cover 110 can be formed of glass, silicon, PDMS, PMMA, cyclo olefin polymer (COP), polycarbonate, polyimide, or other suitable material. The spacer layer 114 is optional and may serve as a supporting layer on which the magnetizable layer 104 may be formed. The spacer layer 114 may be formed of low magnetic permeability material, e.g., a non-magnetic material including, for example, glass or any of a wide variety of plastics.

In some implementations, an additional layer of material may be formed on the surface of the magnetizable layer 104. For example, a layer of material may be formed on the surface of the magnetizable layer 104 to protect the magnetizable layer 104 from damage and/or corrosion from the fluid sample, to provide a surface on which target analytes may be bound, to provide a surface to which the microfluidic cover 110 can be adhered, and/or to isolate the low-permeability region 108 from the fluid sample. FIG. 1C is a cross-sectional view of an example microfluidic device 150 that includes a thin-film layer 152 between the magnetizable layer 104 and the microfluidic cover 110. The thin-film layer 152 may be formed of one or more various materials including, but not limited to, a silicon material, such as silicon dioxide, glass, or any of a wide variety of inert plastics. The thin-film layer 152 may have a thickness in the range of approximately several nanometers to several tens of microns. For example, the thin-film layer 152 may be approximately 10 nm thick, approximately 100 nm thick, approximately 500 nm thick, approximately 1 µm thick, or approximately 5 µm thick. Other thicknesses may be used as well.

In the example shown in FIG. 1A, the low magnetic permeability portion 108 is substantially aligned with a central longitudinal axis of the microfluidic channel 112. The central longitudinal axis of the channel 112 extends along the z-axis into the page and is equidistant from the walls of the channel 112. Similarly, the central longitudinal axis of the elongated low magnetic permeability portion 108 also extends along the z-direction. Other configurations of the channel 112 and low magnetic permeability portion 108 are also possible and, in some implementations, may enhance the isolation of magnetic or magnetically labeled particles from a fluid sample.

Figure 3A:
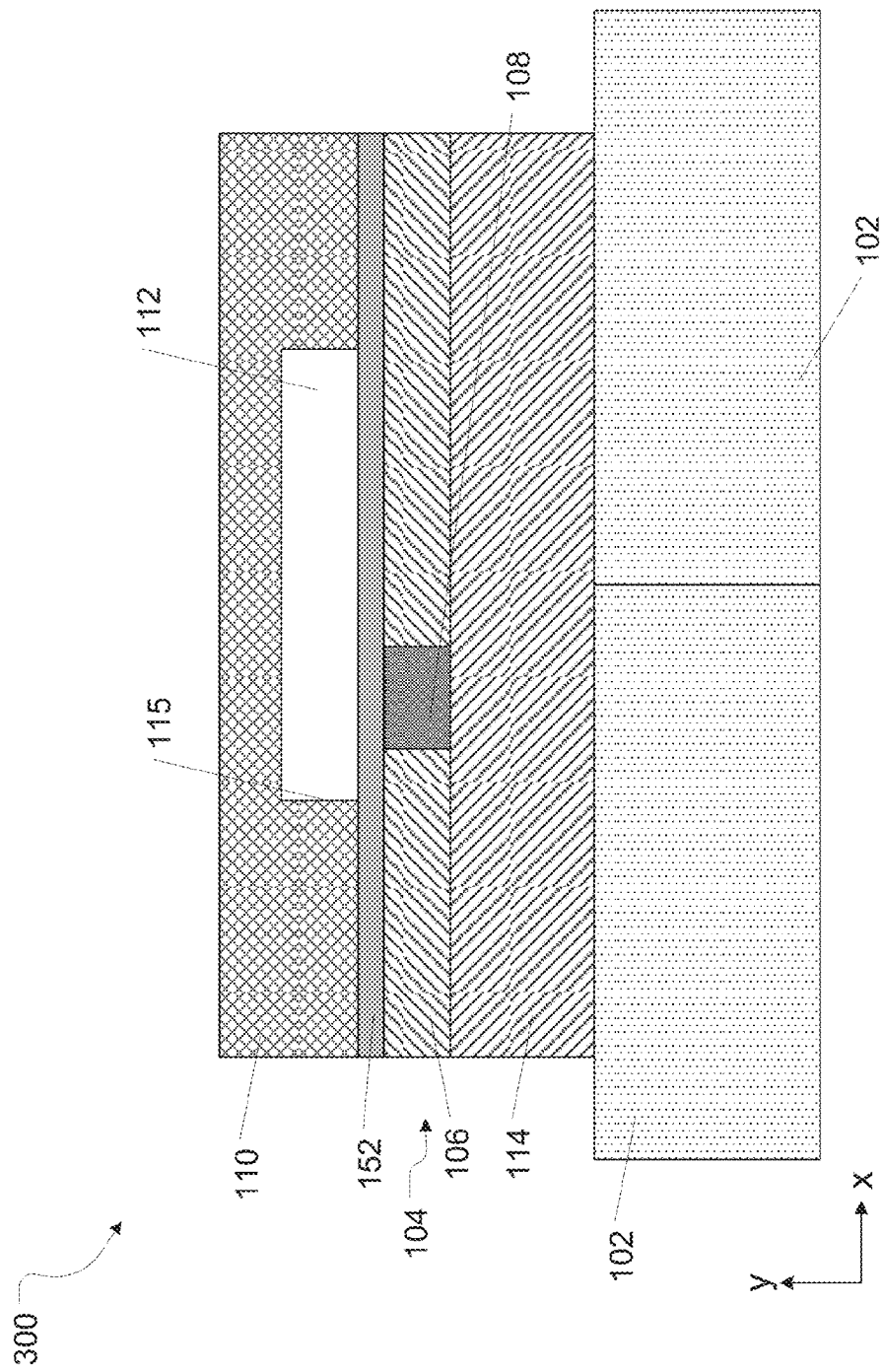
FIG. 3A is a cross-sectional view of a microfluidic device in which a low magnetic permeability region is laterally offset from a central longitudinal axis of the microfluidic channel.
Figure 3B:
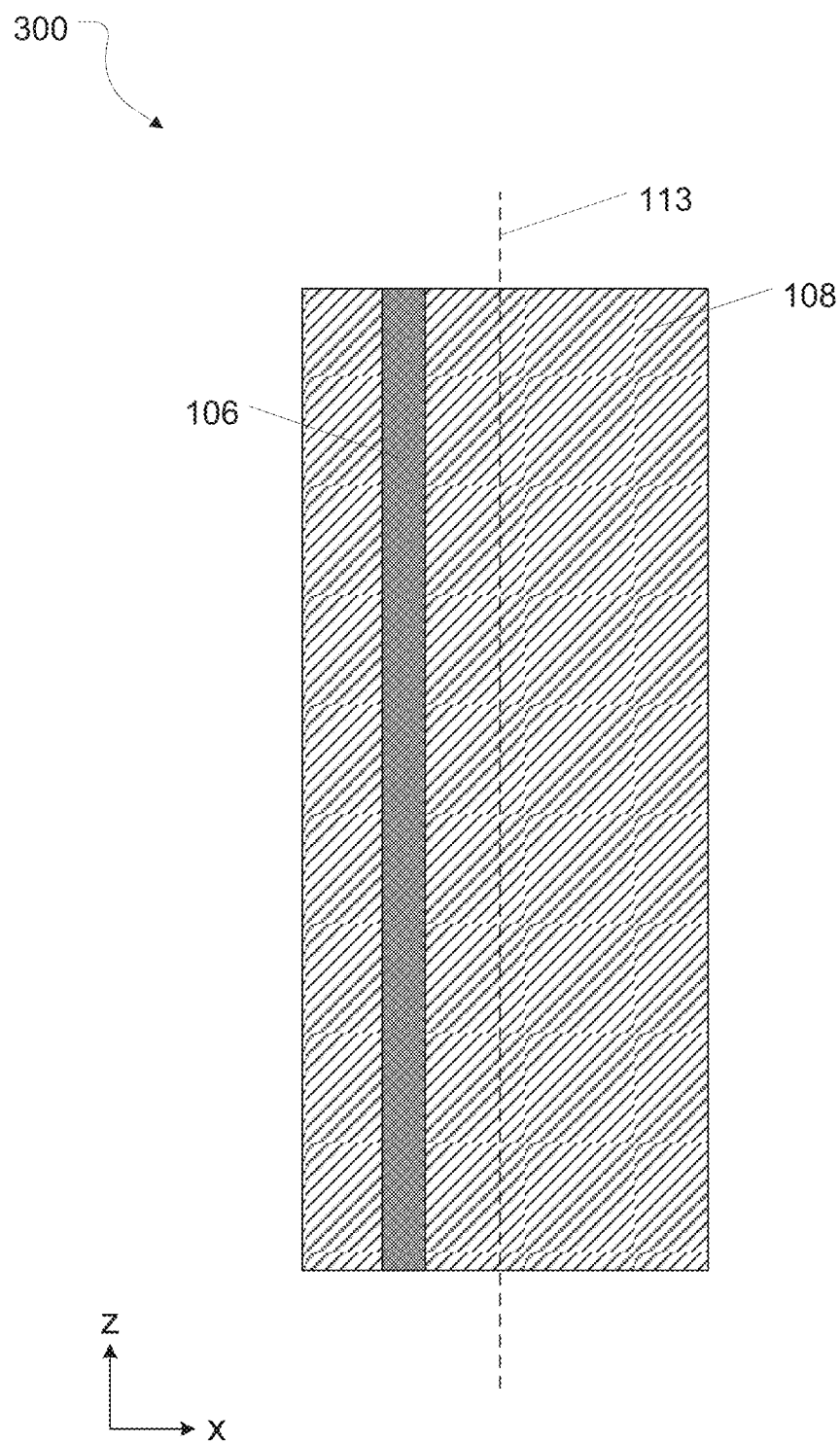
FIG. 3B is a top view of the magnetizable layer of the microfluidic device of FIG. 3A.

For example, in some implementations, the low magnetic permeability region 108 may be laterally offset from the central longitudinal direction of the microfluidic channel 112. FIG. 3A is a cross-sectional view of a microfluidic device 300 in which a low magnetic permeability region 108, bounded by the high magnetic permeability regions 106, is laterally offset from a central longitudinal axis of the microfluidic channel 112. FIG. 3B is a top view of the magnetizable layer 104 of the microfluidic device 300 with the cover 110 removed. The dashed line 113 in FIG. 3B represents the central longitudinal axis of the channel 112. As shown in these examples, the low magnetic permeability region 108 is located closer to a sidewall 115 of the channel 112 than to a center of the channel, in which the channel center corresponds to the central longitudinal axis 113. The flux gradient established by the regions 106 and 108 still gives rise to a magnetic force that pulls magnetic particles flowing through the channel downward toward the surface of the magnetizable layer 104. Because of the lateral offset between the portion 108 and the channel 112, however, magnetic particles flowing through the fluidic channel 112 will also be pulled laterally in the direction of the low magnetic permeability region 108. Given a sufficient distance along the flow direction of the channel 112, the magnetic particles can be substantially isolated from other particles and/or analytes in the sample. In some cases, the channel 112 may include a bifurcation at one end, such that the substantially isolated particles follow one path of the bifurcation whereas the remaining portion of the sample follows the other path of the bifurcation.

Figure 4:
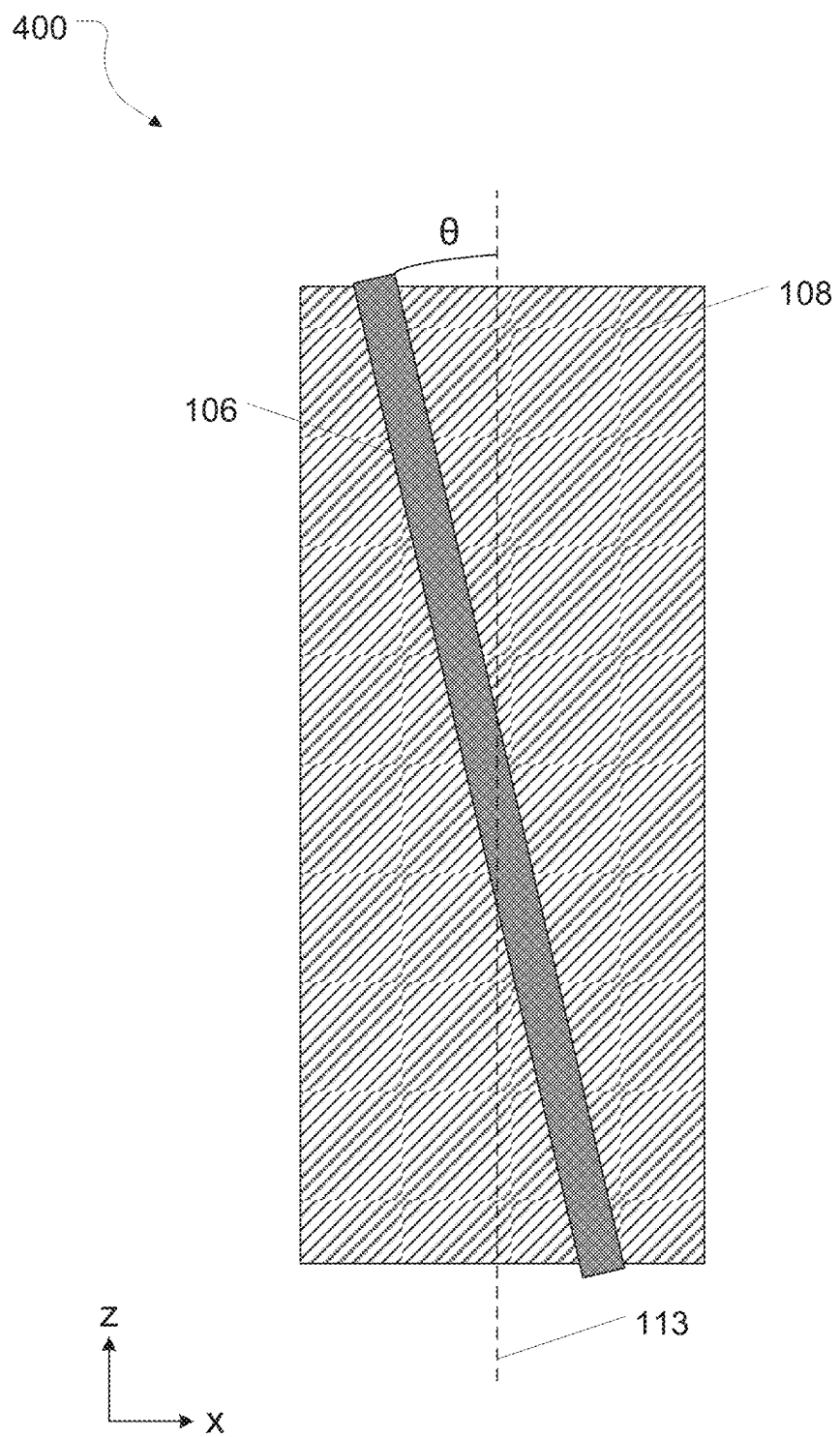
FIG. 4 is a top view of a microfluidic device, with the cover removed, in which a low magnetic permeability region extends at an angle with respect to a flow direction of a microfluidic channel.

In some implementations, the elongated low magnetic permeability region can be arranged at an oblique angle with respect to the central longitudinal axis of the microfluidic channel. FIG. 4 is a top view of a microfluidic device 400, with the cover 110 removed, in which a low magnetic permeability region 108, bounded by the high magnetic permeability regions 106, extends at an angle θ with respect to a flow direction of the microfluidic channel 112, or with respect to a central longitudinal axis 113 of the microfluidic channel 112, e.g., at an oblique or acute angle. Again, the regions 106 and 108 induce a flux gradient that acts as a magnetic force to pull magnetic particles toward the portion 108 and away from other analytes flowing within the sample. The angle θ can be anywhere between, e.g., 0° to 30°, including, for example, about 0.25°, about 0.5°, about 1.5°, about 5°, or about 15°.

The magnetizable layer 104 is not limited to having a single elongated low magnetic permeability region. Instead, in some implementations, the magnetizable layer 104 can include multiple elongated low magnetic permeability regions 108 arranged in parallel, each region 108 being separated from an adjacent region 108 by the high magnetic permeability portion 106. In this way, the width of the flux gradient can be substantially extended. As a result, wider microfluidic channels 112 can be used in which the flux gradient extends across the width of the channels.

FIG. 5A is a cross-sectional view of an example of a microfluidic device 500 having a magnetizable layer 104 in which multiple low magnetic permeability regions 108 are formed and arranged in parallel. As in other examples, a microfluidic cover 110 is formed over the magnetizable layer 104 and includes a microfluidic channel 112. The distance between the portions 108 (i.e., the width of the high magnetic permeability portion 106 between portions 108) may be similar to the widths of portions 108 and in the range of approximately 100 nm to approximately 100 µm. For example, the width of the portions 106 located between low magnetic permeability regions 108 may be approximately 500 nm, approximately 1 µm, approximately 10 µm, approximately 50 µm, or approximately 75 µm. Other widths are possible as well.

Figure 5B:
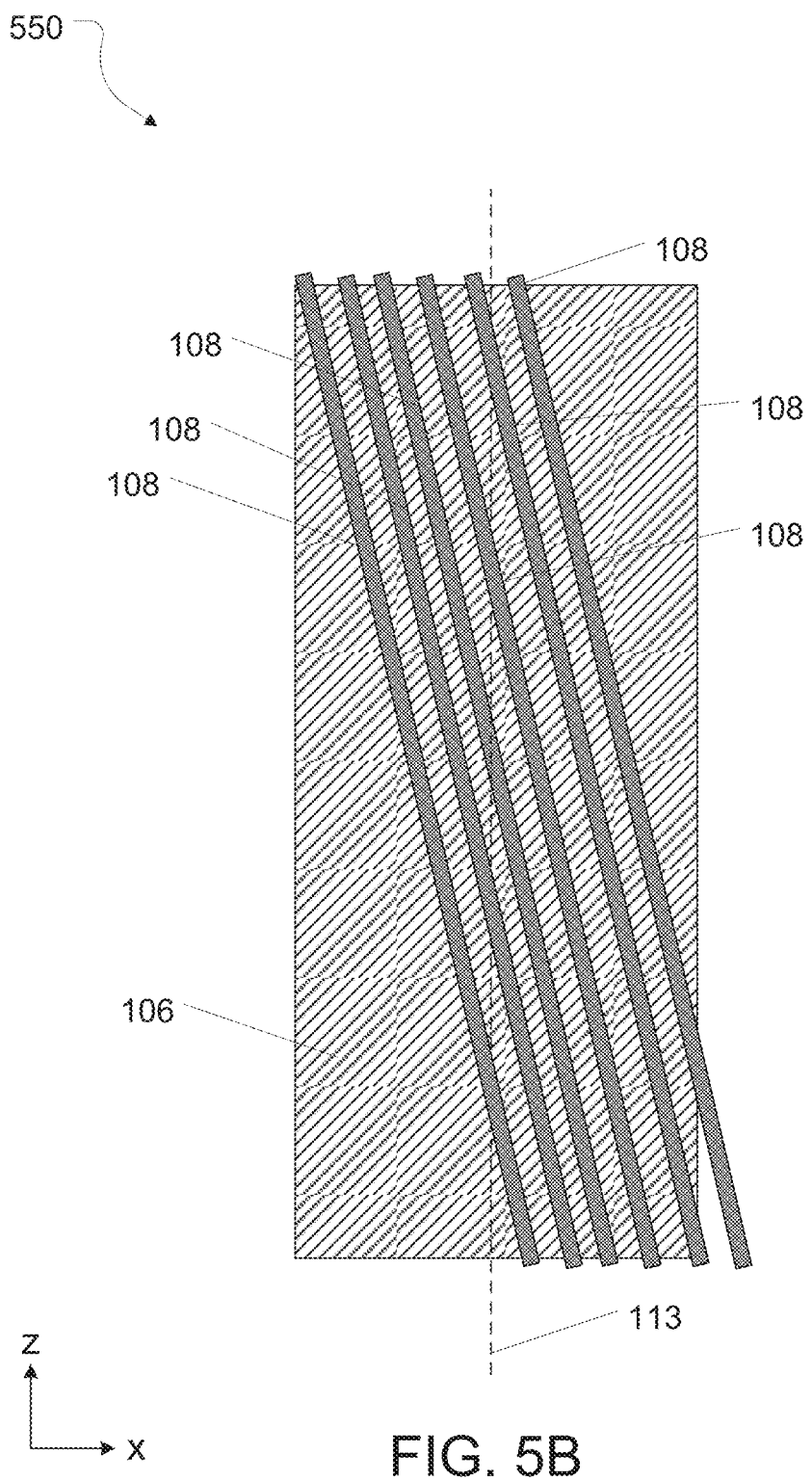
FIG. 5B is a top view of an example of a microfluidic device with a cover removed and showing a surface of a magnetizable layer.

In some implementations, the multiple low magnetic permeability portions 108 may be arranged in parallel as well as at an oblique angle with respect to a central longitudinal axis of the microfluidic channel 112. FIG. 5B is a top view of an example of a microfluidic device 550 with the cover 110 removed and showing a surface of the magnetizable layer 104. In this implementation, the magnetizable layer 104 includes multiple elongated low magnetic permeability portions 108 arranged in parallel and at an oblique angle with respect to a central longitudinal axis 113 of the microfluidic channel. As with the single low magnetic permeability region design, the parallel set of low magnetic permeability regions 108 induce a flux gradient that acts as a magnetic force to pull magnetic particles toward the magnetizable layer 104 and away from a central longitudinal axis of the microfluidic channel 112.

FIGS. 5C-5D are schematics depicting the directional flow of labeled and unlabeled cells in a microfluidic design that includes multiple parallel low magnetic permeability regions ("stripes") and in a microfluidic design that includes a single low magnetic permeability region ("gap"). The schematics show top views of the deflection channel region. Labeled cells move along the magnetizable structures, at a slight angle, e.g., at about 0.25°, about 0.5°, about 1.5°, about 10°, or about 15° relative to the direction of fluid flow, while unlabeled cells move in the direction of fluid flow in the channel.

Alternatively, or in addition, multiple microfluidic channels 112 can be formed on the magnetizable layer 104. Multiple channel regions 112 allow a greater number of fluid samples and/or a greater amount of fluid sample to be examined simultaneously, thus enhancing the efficiency of the microfluidic device. In some implementations, the multiple channel regions 112 may be arranged in parallel such that they each cross over a portion of the one or more low magnetic permeability regions of the magnetizable layer 104.

Figure 6A:
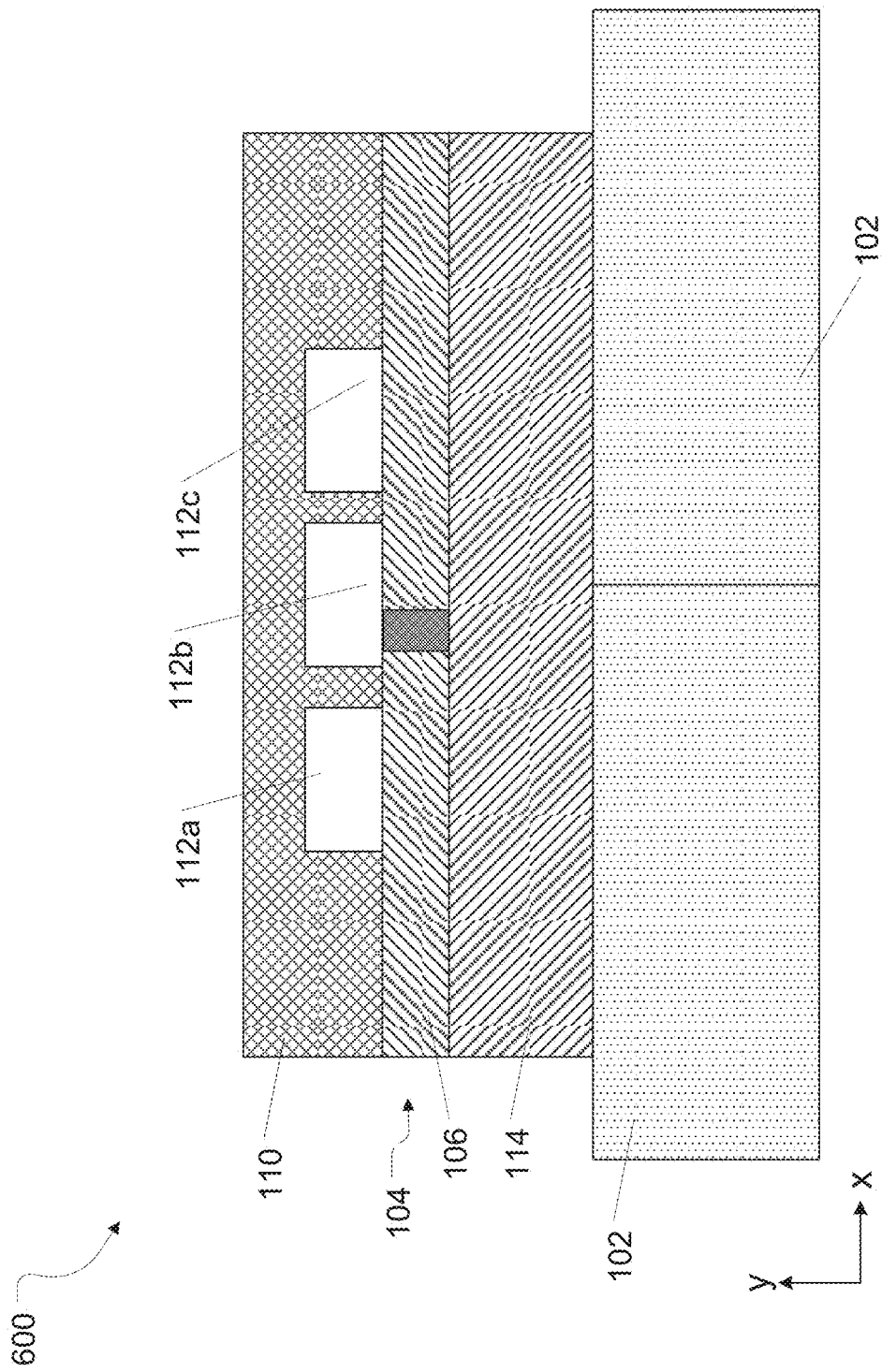
FIG. 6A is a cross-sectional view of an example of a microfluidic device, in which a microfluidic cover includes multiple microfluidic channel regions.
Figure 6B:
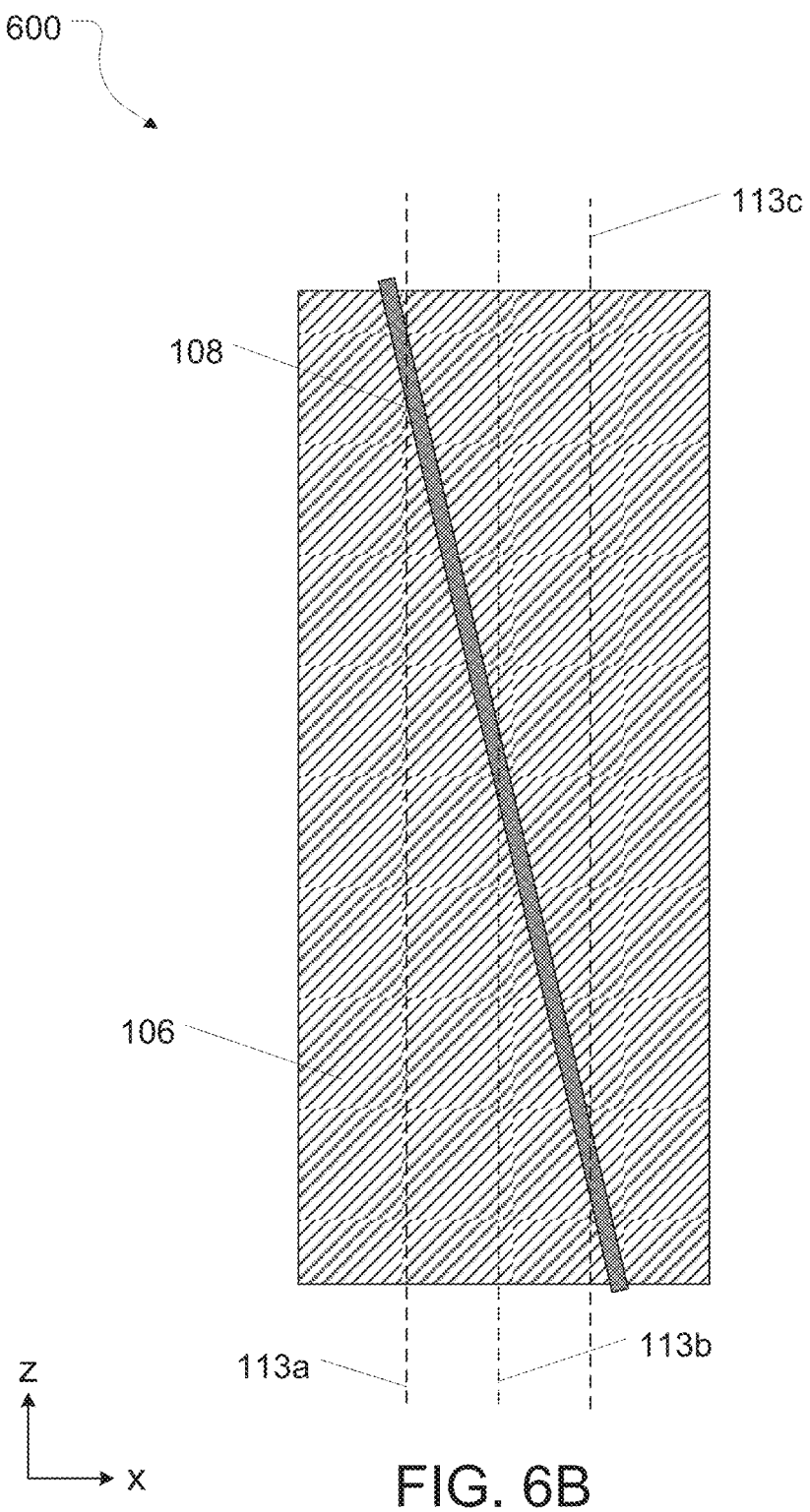
FIG. 6B is a top view of the microfluidic device of FIG. 6A.

FIG. 6A is a cross-sectional view of an example of a microfluidic device 600, in which the microfluidic cover 110 includes multiple microfluidic channel regions 112a, 112b, 112c. FIG. 6B is a top view of the microfluidic device 600. Though the channels 112a, 112b, 112c are not shown in FIG. 6B, the central longitudinal axis 113a, 113b, 113c of each channel 112a, 112b, 112c is indicated by means of a dashed line. As shown in these examples, a single elongated low magnetic permeability region 108 is used in the magnetizable layer. However, the low magnetic permeability region 108 is arranged at an oblique angle with respect to a central longitudinal axis of each of the microfluidic channels, such that the low magnetic permeability region 108 crosses over each of the channels 112 as one moves from a first side of the microfluidic device to a second side of the microfluidic device. Though a single low magnetic permeability region 108 is shown in FIGS. 6A and 6B, multiple low magnetic permeability regions can be used in the magnetizable layer 104, for example in parallel.

Figure 7:
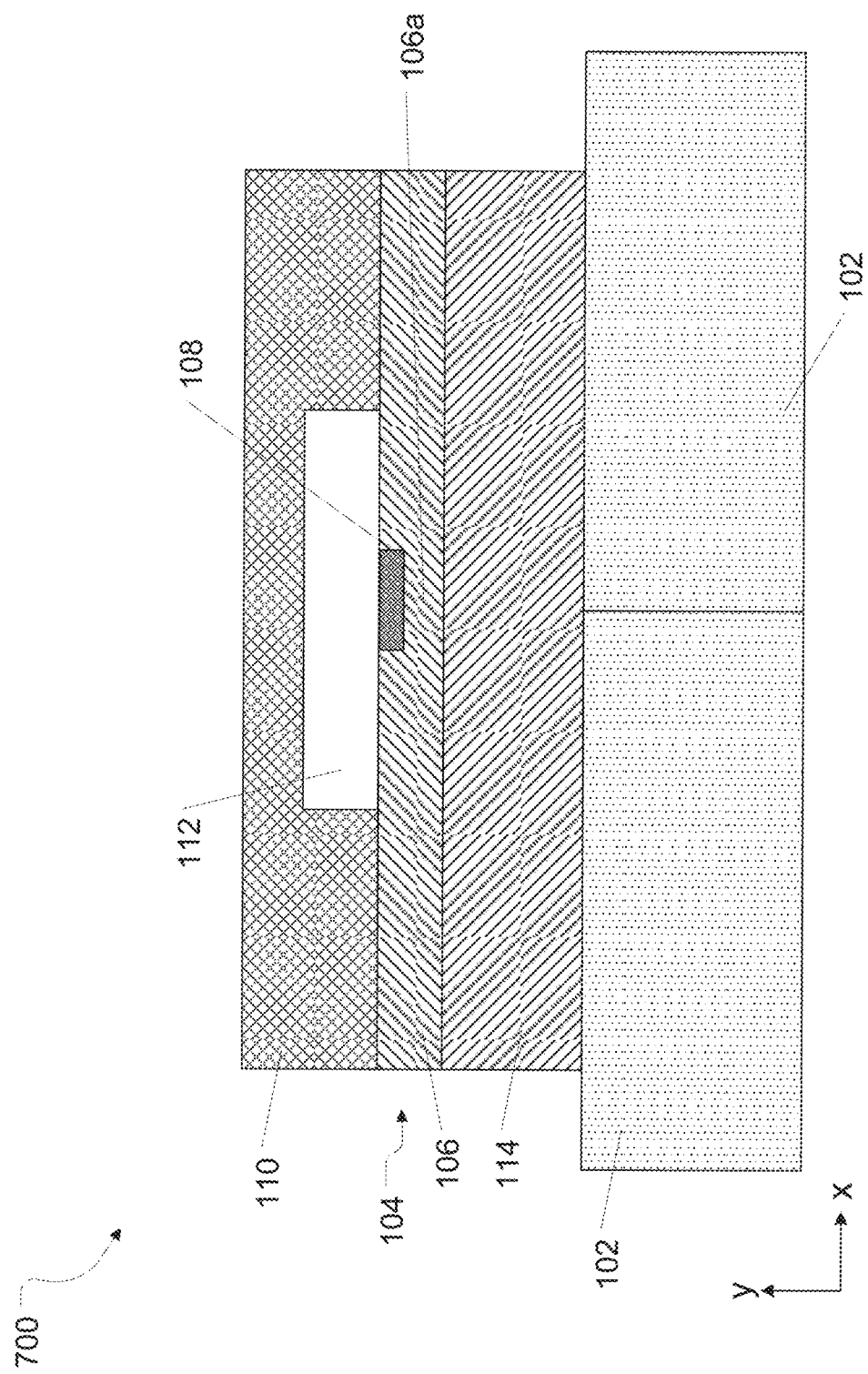
FIG. 7 is a cross-sectional view of a microfluidic device in which a low magnetic permeability region does not extend all the way to a bottom surface of the magnetizable layer.
Figure 8A:
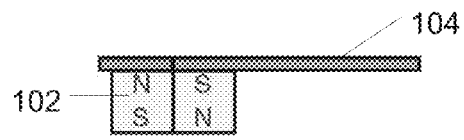
FIGS. 8A-8H are cross-sectional views of different arrangements of magnets around a magnetizable layer of a microfluidic device.
Figure 8E:
Figure 8B:
Figure 8F:
Figure 8C:
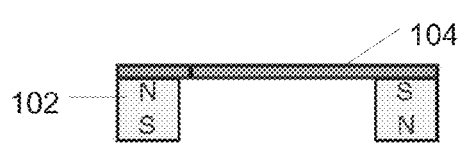
Figure 8G:
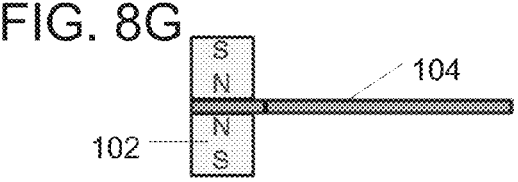
Figure 8D:
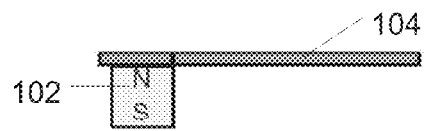
Figure 8H:
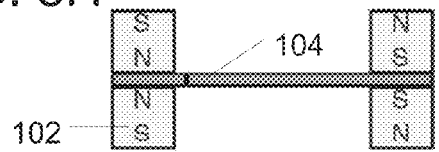

As shown in FIG. 1A, the low magnetic permeability region 108 has a thickness equal to a thickness of the magnetizable layer 104. That is, the low magnetic permeability region 108 extends from a top surface of the magnetizable layer 104 to a bottom surface of the layer 104. In some implementations, the low magnetic permeability region 108 may extend only through a portion of the magnetizable layer 104 that is thinner than the thickness of layer 104. For example, FIG. 7 is a cross-sectional view of a microfluidic device 700 in which the low magnetic permeability region 108 does not extend all the way to a bottom surface of the magnetizable layer. Instead, the portion 108 is exposed on its bottom surface to the high magnetic permeability material 106. In the example device shown in FIG. 7, it is preferable that the high magnetic permeability region 106a beneath the low magnetic permeability region 108 is saturated with the magnetic flux from the magnets 102. This is because when a high magnetic permeability material saturates, the relative permeability of the material approaches one. Thus, by saturating the region 106a beneath the portion 108, the portion 108 and region 106a behave similar to a low magnetic permeability portion 108 that extends completely from a top surface of the magnetizable layer 104 to a bottom surface of the magnetizable layer 104.

Failure to saturate the region 106a may substantially degrade the flux gradient that can be achieved in the channel region 112.

Different configurations of the magnetizable layer can also affect the field gradients that result in the fluidic channels. For example, FIGS. 19A to 19C are a series of schematics that show cross-sections of three different possible configurations of the magnetizable layer. FIG. 19A shows a cross-section of the fluidic device, in which the magnetizable layer 1904 is comprised mainly from high magnetic permeability material 1906, with the exception of the gap region containing the low magnetic permeability material 1908.

FIG. 19B shows a cross-section of the fluidic device, in which the gap is still present, but the portions of the magnetizable layer 1904 containing the high magnetic permeability material 1906 have been reduced in size, relative to the fluidic channels, such that the low magnetic permeability material 1908 surrounds the high magnetic permeability material 1906 in the magnetizable layer 1904. Furthermore, the separation between the microfluidic channels has been increased so that the first isolation stage ("S1") is no longer positioned directly over the high magnetic permeability material 1906. In addition, the fluidic channel cover 1910 that defines the first isolation stage and the second isolation stage ("S2") can be formed of the same low magnetic permeability material as the gap material (or a material having similar low magnetic permeability). For example, the microfluidic cover and the low magnetic material both can be formed from plastic, e.g., from the same type of plastic.

FIG. 19C shows a cross-section of a fluidic device similar to that shown in FIG. 19B, except that there is only one region containing a high magnetic permeability material 1906, thus widening the "gap" to the full extent of the device. In other words, this is a one-sided "gap" that is referred to herein as the "edge" configuration. For example, the high magnetic permeability region 1906 may be a single piece of a magnetic alloy with an edge 1907. Though not shown, the low and high magnetic permeability materials in each of FIGS. 19A-19C are assumed to extend into and out of the page.

Referring back to FIG. 1A, this figure shows an array of two magnets 102 arranged such that each magnet 102 has a magnetic pole orientation that is opposite to a magnetic pole orientation of the adjacent magnet 102. In this arrangement, the magnetic field of each permanent magnet in the array extends to an adjacent permanent magnet in the array. The number of magnets used in the array is not limited to two, however, and may be increased based on the design requirements of the microfluidic device. Alternatively, a single magnet can be used to provide the magnetic flux necessary for creating the flux gradient. In some implementations, the magnets can be arranged so that the magnetic poles of adjacent magnets are in the same orientation, instead of an opposite orientations. In some implementations, the magnets are arranged above or on the sides of the magnetizable layer 104.

FIGS. 8A-8H are cross-sectional views of different arrangements of magnets 102 around a magnetizable layer 104 of a microfluidic device, in which each magnet 102 has a "north" magnetic pole, labeled "N," and a "south" magnetic pole, labeled "S." Each of the implementations shown in FIGS. 8A-8H is capable of generating a magnetic flux that can be used by the magnetizable layer to create a flux gradient in the channel region 112 of a microfluidic device.

When increasing the distance separating the microfluidic channels in the first and second stages, the gradient in the magnetic flux should be big enough in the channel positioned far from the gap or edge to still induce some deflection of magnetic particles in that channel. To ensure a sufficient flux, additional magnets can be placed in the vicinity of the channel that is positioned relatively far from the gap or edge. For example, for the device configuration shown in FIG. 21A (similar to the configuration shown in FIG. 19A), a sufficient flux gradient can be provided with just two magnets 2150 beneath the gap region. In contrast, for the gap configuration shown in FIG. 21B (similar to the configuration shown in FIG. 19B), an additional magnet 2152 can be used to generate magnetic flux in the region corresponding to the first isolation stage S1. In some implementations, further magnets can be added, for example, above the fluidic device in addition to below the device, as shown in FIG. 21B. Similar magnet arrangements would be suitable for the edge and other configurations, such as shown in FIG. 21C.

The different arrangements of the microfluidic device described herein are capable of producing extremely high flux gradients at distances relatively far from the surface of the magnetizable layer that is closest to the microfluidic channel. For example, in some implementations, the magnetizable layer 104 is capable of creating a flux gradient that is at least $10^3$ T/m at a position that is at least 10, 20, 30, 40, or at least 50 μm away from a surface of the magnetizable layer 104. In some implementations, the magnetizable layer 104 is capable of creating a flux gradient that is at least $10^4$ T/m at a position that is at least 20, 30, 40, or at least 50 μm away from a surface of the magnetizable layer 104.

Depending on the thickness of any interlayers between the bottom surface of the microfluidic channel and the top surface of the magnetizable layer, the device can also product high flux gradients at distances relatively far from the bottom surface of the microfluidic channel. For example, in some implementations, the magnetizable layer 104 is capable of creating a flux gradient that is at least $10^3$ T/m at a position that is at least 10, 20, 30, 40, or at least 50 μm away from a bottom microfluidic channel surface. In some implementations, the magnetizable layer 104 is capable of creating a flux gradient that is at least $10^4$ T/m at a position that is at least 20, 30, 40, or at least 50 μm away from a surface of the a bottom microfluidic channel surface.

The high flux gradients that are obtainable with the devices described herein have several advantages. For example, in some implementations, the high flux gradients enable the isolation of target analytes bound to magnetic particles having very low magnetic moments: the high magnetic force in the microfluidic channel exerts a greater "pull" on the magnetic particles having low magnetic moments. Alternatively, or in addition, the high flux gradients enable the isolation of target analytes bound to a lower number of magnetic particles, because the magnetic force is high, fewer magnetic particles having a particular magnetic moment are required to be bound to a target analyte.

In some implementations, the high flux gradient enables magnetically labeled analytes to be separated/isolated at high flow rates (e.g., at least approximately 50 μL/min, at least approximately 100 μL/min, at least approximately 150 μL/min, at least approximately 300 μL/min, at least approximately 500 μL/min, or at least approximately 1000 μL/min), thus increasing the efficiency with which the device can be used for detection and separation of target analytes.

In some implementations, the high flux gradients enable the use of shorter microfluidic channels/isolation regions (e.g., less than approximately 150 mm, less than approximately 100 mm, less than approximately 50 mm, less than approximately 10 mm, or about approximately 1 mm) since magnetically labeled analytes can be separated over much shorter distances.

In some implementations, the high flux gradients enable the low magnetic permeability region to be arranged at shallower angles with respect to a central longitudinal axis of the microfluidic channel. By arranging the low magnetic permeability region at shallower angles, the fluid can flow faster through the microfluidic channel, while still achieving separation of desired particles from undesired particles in the sample fluid. An advantage of faster flow is that clogging in the microfluidic channel can, in certain implementations, be reduced. However, with shallower angles (and increased speed), the length of the microfluidic channel must increase to achieve a specified lateral displacement of desired particles from undesired particles in the sample fluid. This is because the lateral speed of the particles being separated remains essentially constant regardless of the angle of the low magnetic permeability region. Accordingly, the time required to achieve a given lateral separation also remains constant.

The sample fluid flow rate v is approximately inversely proportion to $\sin(\theta)$, where $\theta$ is the angle of the low magnetic permeability region with respect to a central longitudinal axis of the microfluidic channel.

One way to characterize a microfluidic device that isolates target analytes through the use of magnetic force is to specify a ratio, $R_{a/p}$, of a size, A, of the target analyte to a minimum number of magnetic particles, P, bound to the target analyte that would be required to isolate the target analyte. For the purposes of calculating the ratio, size is understood to correspond to an average diameter or average length of the target analyte. Implementations of the microfluidic devices described herein can obtain, for example, analyte size to particle number ratios greater than or equal to approximately 1 µm, greater than or equal to approximately 5 µm, greater than or equal to approximately 10 µm, greater than or equal to approximately 50 µm, or greater than or equal to 100 µm.

FIG. 9A is a schematic of an example of a system 900 that includes a microfluidic device for isolating and/or sorting target analytes based on high magnetic flux gradients. The system includes a microfluidic channel that extends from an inlet 902 through an inertial focusing stage 904 and a deflection channel 906 to an outlet 908. The inertial focusing stage 904 focuses cells in the center of microfluidic channel. Examples and further discussion of inertial focusing can be found, for example, U.S. Pat. No. 8,186,913, incorporated herein by reference in its entirety. A magnetizable layer is located beneath the deflection channel 906 and includes multiple elongated low magnetic permeability portions 108 arranged in parallel and embedded in a high magnetic permeability material. The angle of the low magnetic permeability regions 108 relative to the flow path of the microfluidic channel is about 0° to about 30°, e.g., about 0.25, about 0.5, about 1, about 1.5, about 10, about 15 or about 25°. The outlet 908 splits into a waste channel 910 and a target channel 912. One or more magnets (not shown) are placed adjacent to the system 100 and provide a magnetic field.

The three insets shown in FIGS. 9B, 9C, and 9D are close-up views of the regions 108 at the beginning, middle and end, respectively, of the deflection channel 906. When a fluid sample containing target analytes bound to one or more magnetic particles is introduced into the deflection channel 906, the magnetic force created by the magnetizable layer pulls the magnetic particles (and the attached analytes) in a direction of the low magnetic permeability regions 108. The magnetic particles will accumulate near and follow the regions 108 over the length of channel 906 such that when the fluid sample reaches the outlet 908, the magnetic particles (and the attached analytes) are isolated from other non-labeled analytes in the sample. The portion of the fluid sample containing the non-labeled analytes flows out into the waste channel 910 whereas the magnetic particles flow into the target channel 912. In the example shown in FIG. 9, the regions 108 are presumed to be approximately 40 µm wide with a spacing of approximately 40 µm.

FIG. 10A is a schematic of an example of another system 1000 that includes a microfluidic device for isolating and/or sorting target analytes based on high magnetic flux gradients. The system 1000 is similar to system 900 except that instead of multiple elongated low magnetic permeability regions in a magnetizable layer, the magnetizable layer includes a single low magnetic permeability region 108. In the example of FIG. 10A, the deflection channel 1006 angles up at approximately 0.5° relative to the low magnetic permeability region 108 such that the distance between the region 108 and the wall of the deflection channel 1006 increases (or decreases) along the length of the deflection channel 1006. The three insets shown in FIGS. 10B, 10C, and 10D are close-up views of the regions 108 at the beginning, middle and end, respectively, of the deflection channel 1006.

The position of the gap (which provides two interfaces) or interface (a single interface) between the low magnetic permeability material and the high magnetic permeability material does not have to be in the center of the microfluidic channel width. Instead, in some implementations, the gap (i.e., the low magnetic permeability region between the high magnetic permeability materials) or the interface (i.e., the interface between a high magnetic permeability material and a low magnetic permeability material) may have different arrangements. For example, FIGS. 27A to 27C are schematics depicting top views of examples of different fluidic channels and the structure used to induce the high gradient. Each figure shows an outline of a fluidic channel 2700 and a low magnetic permeability region 2702 such as is formed in the "gap" structure of FIG. 1A. Alternatively, the region 2702 could correspond to the interface between a high magnetic permeability material and the low magnetic permeability material in the "edge" configurations of the microfluidic device. As shown in FIG. 27A, the location of the gap or edge interface may be laterally offset from the walls of the channel 2700, such that the gap or edge appears to be outside of the channel from a top view. Alternatively, the location of the gap or edge may be located directly underneath the channel 2700 (e.g., see FIG. 27B). Alternatively, the gap or edge can be positioned at an oblique angle with respect to a central longitudinal axis of the channel 2700 (e.g., see FIG. 27C).

In some implementations, the channel 2700 itself can include some curvature. The gap or edge of the magnetizable layer that induces the high gradient in the magnetic field can also be curved to substantially follow the curvature of the channel 2700. For example, FIG. 27D is a schematic of a top view of a curved channel 2700, in which the gap/edge region 2702 of the magnetizable layer is also curved, but laterally offset from the channel 2700. FIG. 27E is a schematic of a top view of a curved channel 2700 in which the gap/edge region 2702 follows the curvature of the channel 2700 and is also located directly beneath the channel 2700. FIG. 27F is a schematic of a top view of a curved channel 2700, in which the gap/edge region 2702 is curved and located beneath the channel 2700, but does not follow a central axis of the fluidic channel. Instead, as shown in FIG. 27F, the curved gap/edge region 2702 is oriented obliquely with respect to the central axis of the fluidic channel 2700.

Potential risks of using magnetizable structures that generate large flux gradients within microchannels is clogging with the magnetic particles or with heavily magnetic particle-laden analytes, which are very strongly attracted to the magnetizable layer. Negative effects of this clogging include a reduction in the quality of a focused stream of analytes and/or loss of the target analytes (e.g., through lysis of target cells). The risks of clogging can be mitigated through the use of a multistage microfluidic device that uses multiple regions to isolate target analytes that express different levels of magnetic moment. In some implementations, the clogging can be minimized by using a different configuration of the high magnetic permeability material and low magnetic permeability material in the magnetizable layer.

For example, the magnetizable layer can be constructed to include an "edge" configuration as shown in FIG. 19C, where there is a single interface between the high magnetic permeability material and the low magnetic permeability material, in place of the "gap" configuration. In contrast to the gap configuration, in which magnetic particles (or target analytes bound to magnetic particles) are pulled toward regions of the channel directly above the two interfaces between the low magnetic permeability material and the high magnetic permeability material, the magnetic particles (or target analytes bound to magnetic particles) are pulled toward a single region above the single interface between the low magnetic permeability region and the high magnetic permeability material in the edge configuration. The edge configuration thus has an advantage that target analytes are deflected toward a single line, e.g., in or towards the middle of a microfluidic channel, instead of being pulled to separate regions of the microfluidic channel, e.g., towards the walls of the microfluidic channel), thereby improving the collection and isolation of the target analytes.

Figure 11:
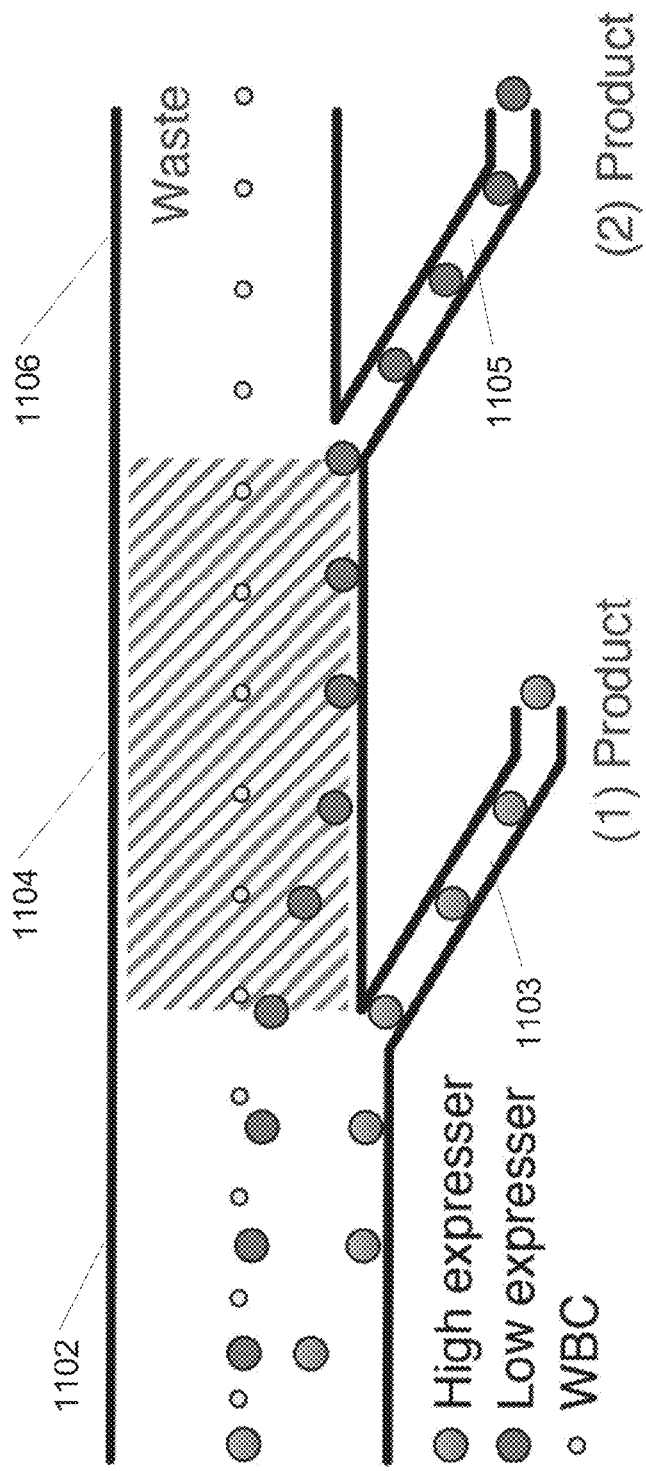
FIG. 11 is a schematic of an example arrangement for a multistage device that utilizes high magnetic flux gradients to isolate target analytes.

FIG. 11 is a schematic of an example of an arrangement for a multistage device that utilizes high magnetic flux gradients to isolate target analytes. The multistage device includes a first stage 1102 for isolating analytes that exhibit high magnetic moments or are bound to particles that exhibit high magnetic moments, a second stage 1104 for isolating analytes that exhibit relatively lower magnetic moments or are bound to particles that exhibit relatively lower magnetic moments, and a third stage 1106 for removing waste or other desired analytes. As shown in the schematic of FIG. 11, the first stage 1102 isolates the particles exhibiting high magnetic moments by deflecting those particles toward a first outlet 1103. The second stage 1104 isolates the particles exhibiting relatively lower magnetic moments by deflecting those particles toward a second outlet 1105.

Multi-stage devices, such as the two-stage device 1100, enable a high-dynamic range for isolating different analytes. For example, the first stage 1102 captures analytes that may have a large magnetic moment and that would otherwise be trapped in the second stage 1104. The large magnetic moment may be due to a large number of magnetic particles bound to the analytes in a fluid sample or because the magnetic particles in the fluid sample each have a high magnetic moment. The second stage 1104 is more sensitive and thus can capture analytes that have a smaller magnetic moment. For example, the analytes captured in the second stage may be bound to a second type of magnetic particles, each of which has a lower magnetic moment relative to a first type of magnetic particle, or the analytes captured in the second stage 1104 may be bound to fewer magnetic particles than the analytes captured in the first stage 1102. For example, if the analytes are cells, the first stage can capture cells that express a specific surface marker molecule at a high level (so that many magnetic particles are bound to the many surface markers), while the second stage can capture cells that express the same surface marker, but at a lower level (so that fewer magnetic particles are bound to the surface of these cells). The remaining analytes, such as white blood cells (WBC) in the example of FIG. 11, are delivered to the third stage 1106.

The multistage device shown in FIG. 11 addresses clogging by removing in the first stage 1102 unbound magnetic particles and magnetic particle aggregates. With the reduction in clogging, the multi-stage device enables, in some implementations, the use of larger magnetic particles and higher magnetic particle concentrations. In addition, the so-called "edge" configuration can also be used to avoid clogging by directing the desired analytes to the center of the microfluidic channels, as opposed to the channel walls.

Figure 12A:
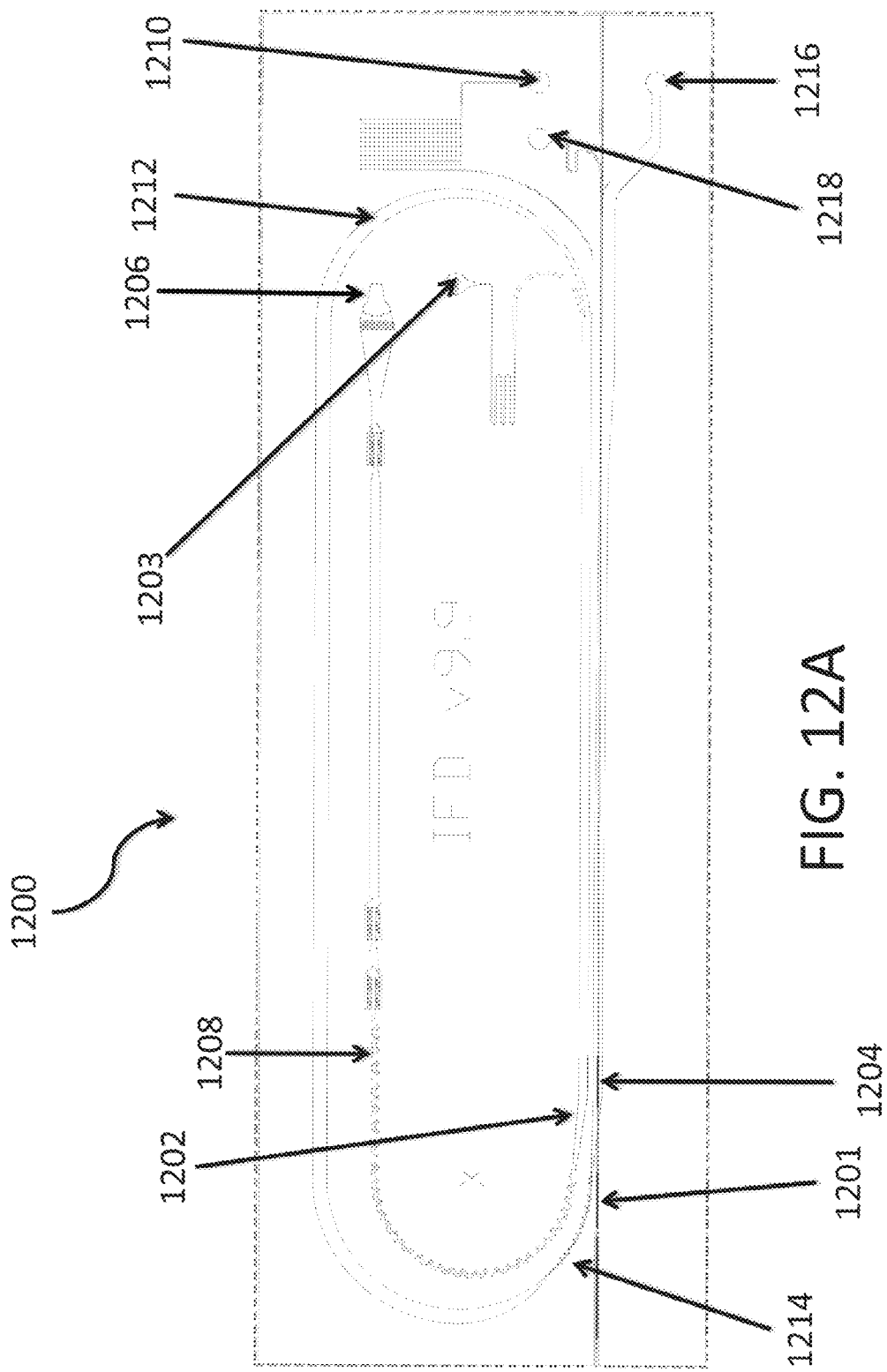
FIG. 12A is a schematic of an example of a system that includes two separate stages for analyte isolation based on the use of magnetic flux gradients.

FIG. 12A is a schematic top view of an example of a system 1200 that includes two separate stages for analyte isolation based on deflection by magnetic flux gradients. The first and second stages form a single continuous channel having two approximately concentric loops. The system 1200 includes an inlet 1206, a first focusing stage 1208, a first deflection channel/isolation stage 1202, and an outlet 1210 for one or more first target analytes isolated in the first deflection channel 1202. The deflection channel 1202 relies on a magnetizable layer that includes one or more low magnetic permeability regions arranged in a high magnetic permeability material to deflect the one or more first target analytes. The deflection of the one or more first target analytes causes those analytes and some of the sample fluid to flow to outlet 1210, where they are collected.

The system 1200 also includes a second inlet 1212 that receives a portion of the remaining fluid sample from the first deflection channel 1202. The portion flowing into inlet 1212 may include all the remaining fluid sample that did not flow into outlet 1210. Alternatively, some of the remaining fluid sample from the first channel 1202 may be "waste" fluid and flow into outlet 1203, whereas a different portion of the remaining fluid sample containing second target analytes may flow into inlet 1212. Once having passed second inlet 1212, the remaining fluid portion enters a second focusing stage 1214 and then a second deflection channel/isolation stage 1204, where the second target analytes are deflected by the magnetic flux gradients into an outlet 1216 to be collected. Any waste fluid (i.e., the portion of the fluid sample less the first and second target analytes) in the second deflection channel 1204 flows into outlet 1218.

Figure 12B:
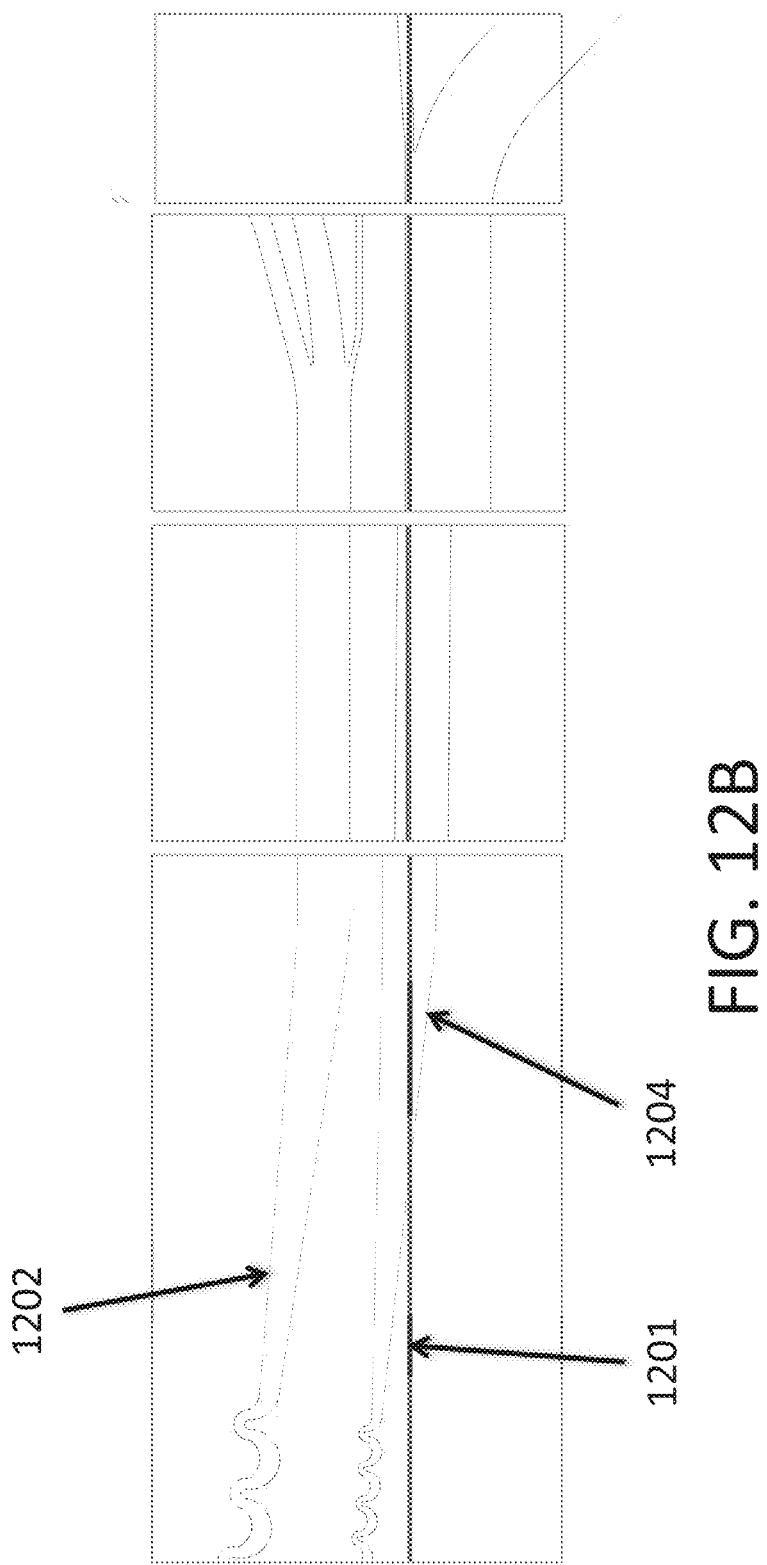
FIG. 12B is a close-up view of the two separate stages for analyte isolation shown in FIG. 12A.

The elongated gap region 1201 containing the low magnetic permeability material extends across the length of the device substantially underneath the second stage 1204. FIG. 12B is a schematic that shows a close-up view of different sections of the first isolation stage 1202 and the second isolation stage 1204. As shown in FIG. 12B, the elongated gap region 1201 is arranged at an oblique angle with respect to a central longitudinal axis of second isolation stage 1204. In contrast, no portion of the low magnetic permeability material 1201 extends underneath the adjacent first isolation stage 1202. As a result of this configuration, the magnetic field gradient is much higher in second stage 1204 than the field gradient in the first state 1202, and a much greater force may be exerted on magnetic particles in the second isolation stage 1204 than in the first isolation stage 1202.

Thus, the second isolation stage 1204 may be better suited for deflecting target analytes having a low overall magnetic moment (e.g., analytes attached to small magnetic particles and/or particles having low magnetic moments), whereas the first isolation stage 1202 may be more appropriate for deflecting target analytes expressing high magnetic moments (e.g., analytes attached to large magnetic particles and/or particles having high magnetic moments) in which the magnetic force does not have to be very high to induce deflection.

In some implementations, clogging in a device, e.g., as those shown in FIG. 12, can be minimized by cycling the magnetic field on and off. By removing or turning off the magnetic flux source, the magnetic flux near the low magnetic permeability region is eliminated, allowing unbound magnetic particles and magnetically labeled particles stuck to the channel wall near the magnetizable layer to free themselves. For systems with permanent magnets, cycling the magnetic field may include physically separating the permanent magnet(s) from the device so that the field does not extend into the microfluidic channel. For systems with electromagnets, cycling the magnetic field may entail cycling a current supplied to the electromagnet. By minimizing magnetic particle accumulation, the device may be re-used, thus reducing waste.

Fabrication of Microfluidic Device

Figure 13:
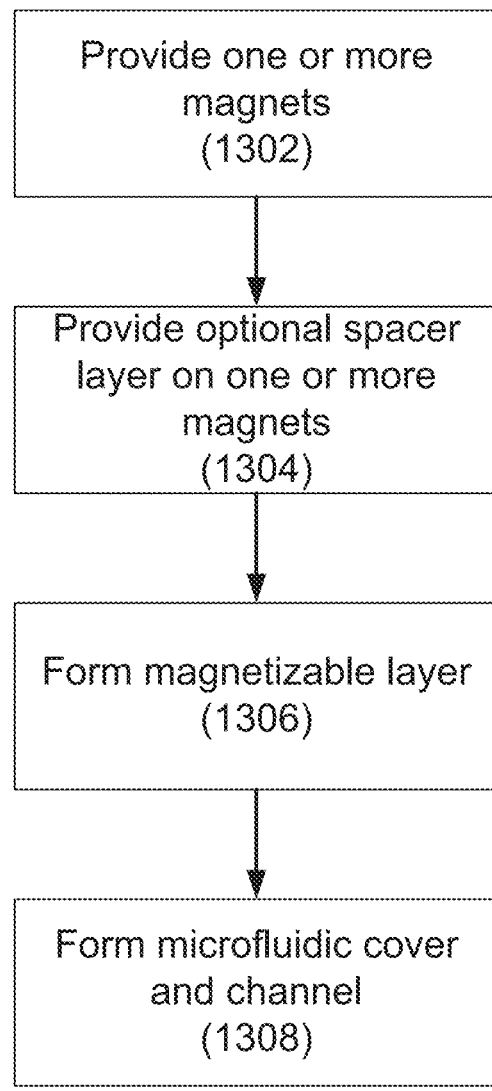
FIG. 13 is a flowchart describing a method for fabricating microfluidic devices described herein.

In general, a microfluidic device for isolating and/or separating target analytes using high magnetic flux gradients can be fabricated as follows. Referring to FIG. 13, one or more magnets are initially provided (1302). The magnet can be made of any suitable magnetic material capable of emitting a high magnetic field (e.g., alloys of NdFeB, SmCo, AlNiCo, or ferrite). An optional spacer layer may then be provided (1304) on a surface of the one or more magnets. The optional spacer layer can include any suitable low magnetic permeability material, e.g., a non-magnetic material, including, for example, glass, plastic or silicon.

A magnetizable layer then is formed (1306) adjacent to the one or more magnets. For example, the magnetizable layer may be formed on a surface of the one or more magnets or on a surface of the optional spacer layer. The magnetizable layer may include, for example, a piece of adhesive magnetic tape. Alternatively, the magnetizable layer may be deposited as a thin or thick film of magnetic material using any suitable deposition technique such as thermal deposition, plasma deposition, electro-plating, or electron-beam deposition. Preferably, the magnetizable layer includes a high magnetic permeability material having high saturation flux density. As explained above, the greater the saturation flux density, the greater the amount of flux that can pass through the high magnetic permeability material leading to gains in flux gradient. Materials that can be used for the high magnetic permeability material include, but are not limited to, iron, nickel, cobalt, or nickel-iron alloys such as $Ni_{80}Fe_{20}$ or $Ni_{45}Fe_{55}$, steel, CoFeNi, FeAlN alloys, SiFe alloys, or CoFe alloys. In some implementations, the high magnetic permeability material can be a composite material, such as a polymer, glass, or ceramic that contains high magnetic permeability particles (e.g., iron, nickel, cobalt, or nickel-iron alloys such as $Ni_{80}Fe_{20}$ or $Ni_{45}Fe_{55}$, steel, CoFeNi, CoFe alloy, FeAlN alloy, or SiFe alloy, particles)

Forming the magnetizable layer can include forming a low magnetic permeability region in the magnetic material of the magnetizable layer. For example, when using adhesive magnetic tape as the magnetic material, one or more elongated portions of the magnetic tape can be cut out prior to placing the magnetic tape on the surface of the magnet or spacer layer. Optionally, the elongated region may be formed by machining the adhesive magnetic tape to remove the magnetic material. Machining may include any standard machining techniques such as turning, boring, drilling, milling, broaching, sawing, shaping, planing, reaming, tapping, grinding, electrical discharge machining, electrochemical machining, electron beam machining, photochemical machining, laser milling, or ultrasonic machining. The cut out portion may be left empty or can be filled with a low magnetic permeability material, e.g., a non-magnetic material, to form the low magnetic permeability region in the magnetizable layer. In case the magnetic material is deposited as opposed to being an adhesive, the elongated region can be formed using applicable etching techniques such as wet etching or dry etching (e.g., plasma etching). The thickness of the portion removed from the magnetic material in any case (machining, cutting or etching) may be equal to or less than a thickness of the magnetic material.

The cut out portion may be filled with a low magnetic permeability material, e.g., a non-magnetic material, using techniques such as thermal deposition, plasma deposition, electro-plating, or electron-beam deposition. An optional thin film layer (e.g., $SiO_2$) can be formed on a surface of the magnetizable layer using, for example, thermal or electron beam deposition, such that the thin-film is conserved a part of the magnetizable layer.

In some implementations, the high magnetic permeability material can be formed using a molding process or a thermoforming process. For example, composite materials such as plastics, glass, or ceramics containing magnetic particles, are amenable to molding or thermoforming processes.

After forming the magnetizable layer, the microfluidic channel and cover are formed above the magnetizable layer (1308). In some implementations, the microfluidic channel and cover are formed by depositing a polymer (e.g., PDMS, PMMA or polycarbonate (PC)) in a mold that defines the fluidic channel regions. The polymer, once cured, then is transferred and bonded to a surface of the magnetizable layer. For example, PDMS can be first poured into a mold (e.g., an SU-8 mold fabricated with two step photolithography (MicroChem)) that defines the microfluidic network of channels. The PDMS then is cured (e.g., heating at 65° C. for about 3 hours). Prior to transferring the solid PDMS structure 710 to the device, the surface of the oxide layers is treated with $O_2$ plasma to enhance bonding.

In some implementations, the microfluidic device can be fabricated such that it includes a removable and/or replaceable portion. The replaceable portion could include, for example, the microfluidic channel, such that after using the device one or more times (e.g., flowing a sample fluid through the microfluidic channel), the fouled channel can be disposed. The channel can then be replaced with a new fresh channel, thus eliminating a washing step and, in some implementations, leading to a reduction in processing time. In some cases, designing the device to include the removable portion may also reduce fabrication costs.

FIG. 14A is a schematic of a first configuration 1500 of a microfluidic device that includes a removable and/or replaceable portion. The configuration 1500 includes a cartridge portion 1502 and an instrument portion 1504. The instrument portion includes the magnets 1506 for generating the magnetic field. The cartridge portion 1502 can be removably fixed to the instrument portion 1504 and includes the microfluidic channel cover 1508, the microfluidic channel 1510 (e.g., which is defined by the microfluidic channel cover 1508), a passivation layer 1512, which acts as the floor of the microfluidic channel 1510, the low permeability region 1514 (e.g., a gap containing vacuum or air or other low magnetic permeability material), and the high permeability region 1516 (e.g., a magnetizable alloy).

FIG. 14B is a schematic of a second configuration 1550 of a microfluidic device that includes a removable and/or replaceable portion. The configuration 1550 includes cartridge portion 1552 and an instrument portion 1554. The instrument portion 1554 includes the magnets 1506 for generating the magnetic field, the low permeability region 1514 (e.g., a gap containing vacuum or air or other low magnetic permeability material), and the high permeability region 1516 (e.g., a magnetizable alloy). The cartridge portion 1552 can be removably fixed to the instrument portion 1504 and includes the microfluidic channel cover 1508, the microfluidic channel 1510 (e.g., which is defined by the microfluidic channel cover 1508), and a passivation layer 1512, which acts as the floor of the microfluidic channel 1510.

In either design, the passivation layer 1512 is preferably non-magnetizable and is thin enough to minimize the distance between a top surface of the magnetizable alloy 1516 and the floor of the microfluidic channel 1510. For example, the thickness of the passivation layer could be less than approximately 5 µm. The passivation layer 1512 can be bonded to the microfluidic cover 1508 using plasma or using an adhesive, such as epoxy. To ensure proper alignment, it is preferable that the base layer does not stretch significantly. Examples of materials for the passivation layer include coextruded metal and polymer (e.g., an aluminum layer sandwiched between polymer layers.).

To aid in coupling the cartridge portion 1502 (1552) to the instrument portion 1504 (1554), the instrument portion 1504 (1554) and the cartridge portion 1502 (1552) can include alignment markers, such as cross-hairs or other shapes, which can be used to align the two portions to one another. For example, for configuration 1500, the alignment markers can be formed on the magnets 1506 and on one of the layers of the cartridge portion 1502 (e.g., the microfluidic channel cover 1508) using known etching or deposition techniques. In some implementations, the low permeability region 1514 itself can be used as an alignment marker. Alignment can be performed manually or using an automated alignment system. The alignment marks can be used, in some cases, to enable alignment within 5 µm precision.

Once aligned, the cartridge portion 1502 (1552) can be fixed to the instrument portion 1504 (1554). To enable the cartridge portion 1502 (1552) to be removably fixed to the instrument portion 1504 (1554), the cartridge portion 1502 (1552) and instrument portion 1504 (1554) can include grooves or ridges that mate with one another and snap-lock into place. Alternatively, in some implementations, the cartridge portion 1502 (1552) may include a ridge portion on its bottom surface that slides into a groove formed on the instrument portion 1504 (1554) and locks into place or vice versa. For example, the ridges may be formed to have a T-shape (e.g., a wide top and narrow base) that slides into a slot formed on the instrument portion, where the slot has a wide opening at its base and narrow opening at the top to secure the cartridge in place.

In some implementations, the layer containing the high magnetic permeability material and the low magnetic permeability material can be included as part of the cartridge portion 1552, but also be reusable. However, the microfluidic channel cover 1508 and passivation layer 1512 would be disposable. In this example, the passivation layer would be reversibly bound or mechanically held to the layer containing the high magnetic permeability material and the low magnetic permeability material. After use of the device, the fluidic layer could be removed/released from layer containing the high magnetic permeability material and the low magnetic permeability material. In some cases, the alloy/gap part could then be returned, for example, to a source factory to be reused with a new fluidic layer. An advantage of this approach would be that the alignment of the fluidic layer with the layer containing the high and low magnetic permeability materials could be done in a central facility, rather than with the end user.

In some implementations, the orientation of the microfluidic channel(s) can be modified manually with respect to the magnetizable layer. For example, in some cases, the microfluidic channel is formed as part of a cartridge that removably couples to an instrument portion containing the magnetizable layer and the one or more magnets. The cartridge may be rotatably fixed or translated with respect to the magnetizable layer of the instrument portion such that the direction of the force induced by the magnetic gradient changes relative to the flow direction of the microfluidic channel. That is, the cartridge may be rotated or translated to one of several different positions with respect to the magnetizable layer and then fixed in place in any one of the different positions using a locking mechanism, such as, e.g., a combination of ridges and slots configured to mate with one another.

FIGS. 28A-28F are schematics depicting top views of examples of different arrangements of a microfluidic channel with respect to a high magnetic flux gradient inducing structure. Each figure shows an outline of a fluidic channel 2800 and a low magnetic permeability region 2802 such as is formed in the "gap" structure of FIG. 1A. Alternatively, the region 2802 could correspond to the interface between a high magnetic permeability material and the low magnetic permeability material in the "edge" configurations of the microfluidic device. Each fluidic channel includes three possible outlets ("Output 1," "Output 2," and "Output 3"). When the cartridge containing the fluidic channels is rotated (see FIGS. 28A-28C) relative to the low magnetic permeability region 2803, the force experienced by a magnetic particle 2804 may cause the particle 2804 to follow a trajectory toward one of the three outlets, depending on the amount of rotation of the cartridge. For example, in FIG. 28A, the particle 2804 follows the low magnetic permeability region 2802 toward output 1.

In FIGS. 28B and 28C, the particle 2804 follows the low magnetic permeability region 2802 toward outputs 2 and 3, respectively, as the fluidic channel is rotated. Alternatively, or in addition, the cartridge may be translated relative to the low magnetic permeability region 2802 (see FIGS. 28D-28F), a particle 2804 flowing through the fluidic channel 2800 again may experience a force that causes it to flow toward one of the different output, depending on the amount of shift. For example, in FIG. 28D, the fluidic channel is shifted downward with respect to the region 2802, such that the particle 2804 follows the low magnetic permeability region 2802 toward output 1, whereas in FIGS. 28E and 28F, the particle 2804 follows the low magnetic permeability region 2802 toward outputs 2 and 3, respectively.

Microfluidics

In some implementations, the microfluidic channel 112 of the microfluidic devices described herein can be a part of a larger optional microfluidic channel network. Such microfluidic networks can be used to facilitate control and manipulation (e.g., separation, segregation) of small volumes of liquid and help isolate target analytes from a complex parent specimen. During the isolation process, microfluidic elements provide vital functions, for example, handling of biological fluids, reproducible mixing of magnetic particles with samples, distribution of aliquots to different coils for parallel sensing, and confining of samples to the most sensitive region of a given microcoil. Additional information about microfluidic channel networks and their fabrication can be found in U.S. Patent App. Publication No. 2011/0091987, e.g., in paragraphs eighty-one to eighty-eight.

Use of Magnetic Particles

As noted above, a fluid sample that may contain a target analyte that is mixed with a liquid containing a number of particles that are designed to specifically bind to the target analyte. The particles can include magnetic particles (e.g., nanoparticles) that form a target-particle complex in solution.

Particles

Magnetic particles can include one or more inner magnetic cores and an outer coating, e.g., a capping polymer. The magnetic cores can be monometallic (e.g., Fe, Ni, Co), bimetallic (e.g., FePt, SmCo, FePd, FeAu) or can be made of ferrites (e.g., $Fe_2O_3$, $Fe_3O_4$, $MnFe_2O_4$, $NiFe_2O_4$, $CoFe_2O_4$). The magnetic particles can be nanometers or micrometers in size, and can be diamagnetic, ferromagnetic, paramagnetic, or superparamagnetic, in which size corresponds to an average diameter or average length. For example, the magnetic particles can have a size of approximately 1 μm, approximately 600 nm, approximately 500 nm, approximately 300 nm, approximately 280 nm, approximately 160 nm, or approximately 100 nm. Other particle sizes are possible as well. The outer coating of a particle can increase its water-solubility and stability and also can provide sites for further surface treatment with binding moieties.

Binding Moieties

In general, a binding moiety is a molecule, synthetic or natural, that specifically binds or otherwise links to, e.g., covalently or non-covalently binds to or hybridizes with, a target molecule, or with another binding moiety (or, in certain embodiments, with an aggregation inducing molecule). For example, the binding moiety can be a synthetic oligonucleotide that hybridizes to a specific complementary nucleic acid target. The binding moiety can also be an antibody directed toward an antigen or any protein-protein interaction. Also, the binding moiety can be a polysaccharide that binds to a corresponding target. In certain embodiments, the binding moieties can be designed or selected to serve, when bound to another binding moiety, as substrates for a target molecule such as enzyme in solution. Binding moieties include, for example, oligonucleotides, polypeptides, antibodies, and polysaccharides. As an example, streptavidin has four sites (binding moieties) per molecule that will be recognized by biotin. For any given analyte, e.g., a specific type of cell having a specific surface marker, there are typically many known binding moieties that are known to those of skill in the relevant fields.

For example, certain labeling methods and binding moiety techniques are discussed in detail in U.S. Pat. No. 6,540,896 entitled, "Microfabricated Cell Sorter for Chemical and Biological Materials" filed on May 21, 1999; U.S. Pat. No. 5,968,82050 entitled, "Method for Magnetically Separating Cells into Fractionated Flow Streams" filed on Feb. 26, 1997; and U.S. Pat. No. 6,767,706 entitled, "Integrated Active Flux Microfluidic Devices and Methods" filed Jun. 5, 2001.

Conjugate Preparation

The surface of the magnetic particles are treated to present functional groups (e.g., $-NH_2$, $-COOH$, $-HS$, $-C_nH_{2n-2}$) that can be used as linkers to subsequently attach the magnetic particles to cells other target molecules (e.g., antibodies, drugs). In some cases, the surface treatment makes the magnetic particles essentially hydrophilic or hydrophobic. The surface treatment can be formed of polymers including, but not limited to, synthetic polymers such as polyethylene glycol or silane, natural polymers, derivatives of either synthetic or natural polymers, and combinations thereof.

In some implementations, the surface treatment is not a continuous film around the magnetic particle, but is a "mesh" or "cloud" of extended polymer chains attached to and surrounding the magnetic particle. Exemplary polymers include, but are not limited to polysaccharides and derivatives, such as dextran, pullanan, carboxydextran, carboxmethyl dextran, and/or reduced carboxymethyl dextran, PMMA polymers and polyvinyl alcohol polymers. In some implementations, these polymer coatings provide a surface to which targeting moieties and/or binding groups can bind much easier than to the shell material. For example, in some embodiments magnetic particles (e.g., iron oxide nanoparticles) are covered with a layer of 10 kDa dextran and then cross-linked with epichlorohydrin to stabilize the coating and form cross-linked magnetic particles.

Additional information on the fabrication, modification and use of magnetic particles can be found, for example, in PCT Pub. No. WO/2000/061191, U.S. Patent App. Pub. No. 20030124194, U.S. Patent App. Pub. No. 20030092029, and U.S. Patent App. Pub. No. 20060269965.

Applications

The new microfluidic device described herein can be used in various applications including, for example, as part of a research platform to study analytes of interest (e.g., proteins, cells (such as circulating tumor cells (CTCs) or fetal cells, e.g., in maternal blood), bacteria, pathogens, and DNA) or as part of a diagnostic assay for diagnosing potential disease states or infectious agents in a patient. Examples of detection targets are discussed in more detail below and in the Examples section.

Detecting Infectious Agents

By modifying the functional ligands (e.g., binding moieties) on the magnetic particles, the microfluidic devices described herein can be used to detect, isolate, and/or measure many different biological analytes, including small molecules, proteins, nucleic acids, pathogens, and cells, e.g., rare cells such as cancer cells.

Rare Cell Detection

The microfluidic devices and methods described herein can be used to detect rare cells, such as circulating tumor cells (CTC) in a blood sample, or fetal cells in blood samples of pregnant females. For example, primary tumor cells or CTCs can be targeted and linked to magnetic particles and can be detected using the new microfluidic device for a rapid and comprehensive profiling of cancers. By changing binding molecules on the magnetic particle surface, different types of cells can be detected (e.g., circulating endothelial cells for heart disease). Thus, the microfluidic device may be used as a powerful diagnostic and prognostic tool. The targeted and detected cells can be cancer cells, stem cells, immune cells, white blood cells, or other cells including, for example, circulating endothelial cells (using an antibody to an epithelial cell surface marker, e.g., the Epithelial Cell Adhesion Molecule (EpCAM)), or circulating tumor cells (using an antibody to a cancer cell surface marker, e.g., the Melanoma Cell Adhesion molecule (CD146)). In some implementations, the system sensitivity can detect as low as a few cells or less per milliliter of detection volume, i.e., the device itself has the capacity for single-cell detection. The systems and methods also can be used to detect small molecules, proteins, nucleic acids, or pathogens.

Multiplexed Detection

Detecting multiple biomarkers in one parent sample is an important and highly desirable task for diagnosis and prognosis of complex diseases. For example, there is no ubiquitous biomarker for cancer; multi-channeled screening is required to correctly identify tumor types. The new microfluidic devices described herein offer methods to detect different relevant biomarkers from the aliquots of a single, parent sample, e.g., in patients with cancer or metabolic disorders. A multistage microfluidic device is well suited for this application. In a multistage device, different target analytes (e.g., white blood cell versus red blood cell) may be bound to different magnetic particles or different amounts of magnetic particles such that the different target analytes exhibit a different response to the flux gradient in the microfluidic channel. The target analytes bound to magnetic particles having a high responsivity may be deflected easier than target analytes bound to magnetic particles having a lower responsivity.

Thus, in a first stage of the microfluidic device, the analytes expressing higher responsivity may be filtered out of the sample to isolate the analytes expressing the lower responsivity (or vice versa). In a second stage of the microfluidic device, the analytes expressing the lower responsivity to the flux gradient then can be filtered out from the sample. Examples of tumor cell biomarkers that can be detected include MUC-1, EGFR, B7-H3, Her2, Ki-67, EpCam, Vim, and CK18.

EXAMPLES

The invention is further described in the following example, which does not limit
the scope of the invention described in the claims.

Example 1—Isolating Cancer Cells in Blood

The purpose of this example was to simulate a cancer patient's blood by spiking cell line cancer cells (CTCs) into a healthy donor's blood sample, efficiently tagging these cancer cells with magnetic beads, and isolating the cancer cells for detection and/or further measurements. White blood cells also were analyzed.

Device Fabrication

Several different types of microfluidic devices were fabricated and evaluated to determine performance. To fabricate the devices, the fabrication steps outline above with respect to FIG. 13 were followed. In particular, a 1 mm thick glass substrate was provided for each device. Approximately 1 μm of FeAlN was deposited on the surface of the glass substrates using sputtering. The saturation flux density of FeAlN is about 1.8 T. The FeAlN layer was then patterned into multiple parallel arrangements of stripes. Patterning was accomplished by sputtering FeAlN onto the glass substrate and then etching FeAlN away from areas outside the stripes. Each sample had a different stripe width and/or separation distance (gap) between stripes.

Table 1 below provides the dimensions for the different sample devices M5.1 to M5.5. The width of the low magnetic permeability region for the "gap" device was 20 μm.

TABLE 1

| Design | Stripe width (μm) | Gap width (μm) |
|---|---|---|
| M5.1 | 20 | 10 |
| M5.2 | 40 | 40 |
| M5.3 | 40 | 5 |
| M5.4 | 40 | 20 |
| M5.5 | 60 | 20 |

The surfaces of the stripes were then passivated with a thin layer of $SiO_2$ (approximately 0.2 μm thick). The microfluidic channels were fabricated using standard soft lithography. A SU-8 (MicroChem) mold was fabricated using photolithography. The shape of the mold defined a microfluidic channel region. Polydimethylsiloxane (PDMS) was poured onto the mold and cured at 65° C. for about 8 hours. For each device, the PDMS microfluidic cover and was treated with $O_2$ plasma, aligned with the device substrates using a mask aligner, and permanently bonded to the substrates. The PDMS cover was aligned with the stripes such that the stripes were at an approximately 1° angle from a central longitudinal axis of the microfluidic channel. The "gap" device was constructed with an angle of about 0.5° from a central longitudinal axis of the microfluidic channel.

Magnetic Bead Preparation

Magnetic beads having a diameter of about 1.0 μm were prepared for use in whole blood for labeling CTCs.

In particular, streptavidin coated magnetic beads (Dynabeads MyOne Streptavidin T1 magnetic beads from Invitrogen) were incubated with biotinylated anti-hEpCAM antibodies (R&D Biosystems). Anti-hEpCAM coated beads bind specifically to CTCs that express EpCAM molecules on their surface. The 1 μm magnetic beads used in this procedure were washed with 0.01% TWEEN® 20 (Fisher Scientific) diluted in 1×PBS. EpCAM antibody was then added to the beads, which were washed again by using 0.01% TWEEN 20 diluted in 1×PBS. During antibody incubation, antibody concentration was about 100 μg/ml and bead concentration was about 2 mg/ml. The concentration was then increased to about 5 mg/ml by reducing the volume right before being spiked into the blood sample. 160 nm magnetic beads (Veridex Ferrofluid) were received from Veridex ready to use (i.e., the beads are pre-functionalized with EpCAM ourselves).

Sample Preparation

EpCAM were spiked into a healthy whole blood fluid sample, and then 1.0 μm magnetic beads coated with EpCAM antibody or the 160 nm magnetic beads coated with EpCAM antibody were added to the fluid sample. The sample was added to a sample tube and actively mixed using a tri-pole magnet (Vendex) so as to bind the magnetic beads to the CTCs. Active mixing included placing the sample tube adjacent to the magnet and modifying the tube orientation over a period of several minutes. Active magnetic mixing increases the number of collisions between the beads and target cells and enhances the chance of interaction.

Device Operation

1% Pluronic F68 (BASF) was first prepared and introduced into the microfluidic channel of the microfluidic device for about 15 minutes using a syringe pump (New Era Pump System) to prime the microfluidic device. After the buffer solution was collected at an outlet of the microfluidic device, the blood sample fluid (approximately 7 mL) containing the mixture of CTCs bound to magnetic beads was introduced into the microfluidic device. Prior to introducing the blood sample into the microfluidic device, the blood was debulked (i.e., RBCs, free beads, platelets were removed). The microfluidic device isolated magnetically labeled cells within the sample, from non-labeled cells. The portion of the fluid sample containing the magnetically labeled cells were collected in a product tube and the remaining blood sample was collected in a waste tube. After the blood sample passed through the microfluidic device, the channel was once again flushed with buffer solution.

The blood sample collected in the product tube and the waste sample were analyzed to get an accurate count of spiked cell and WBC contents in them. Spiked cells were pre-stained with CELLTRACKER® Red to allow the manual count from the IFD product and waste samples. The blood sample also was stained with Calcein-AM, thus staining both the WBCs and specific cells, and allowing a count of WBC concentration as well.

Spike cell and WBC concentrations in the blood sample and waste were measured or found by manual counting; then, the total number of cells in each of them was interpolated to estimate percent recovery yields and product purity.

Results

The metrics of device performance are (1) relative yield, (2) absolute yield, and (3) white blood cell carryover (or purity). The relative yield is defined as the percentage of counted output (product+waste) cells found in the product. The absolute yield is defined as the percentage of (assumed) input (spiked) cells found in the product.

Tables 2, 3, and 4 summarize the results of magnetic design comparison experiments. Table 2 shows relative yield, Table 3 shows absolute yield, and Table 4 shows white blood cell carryover. In the Bead Type column, "DB" indicates Dynal Dynabeads (1 μm diameter) and "FF" indicates Veridex Ferrofluid (160 nm diameter).

TABLE 2

Relative Yield in Comparison Experiments

Experimental Conditions

| | | | Bead Conc. | Relative Yield (%) | | | | | |
| | | | | Stripe | | | | | Gap |
| Exp. # | Cell Line | Bead Type | (μg/mL) | M5.1 | M5.2 | M5.3 | M5.4 | M5.5 | M6 |
|---|---|---|---|---|---|---|---|---|---|
| 1 | MB231 | DB | 100 | | 83 | | | | |
| 2 | SKBR3 | FF | 100 | 97 | | | | | |

TABLE 2-continued

Relative Yield in Comparison Experiments

Experimental Conditions

| | | | Bead Conc. | Relative Yield (%) | | | | | |
| | | | | Stripe | | | | | Gap |
| Exp. # | Cell Line | Bead Type | (μg/mL) | M5.1 | M5.2 | M5.3 | M5.4 | M5.5 | M6 |
|---|---|---|---|---|---|---|---|---|---|
| 3 | PC3-9 | FF | 4.4 | | 62 | | | | |
| 4 | PC3-9 | FF | 4.4 | 81 | | | | | |
| 5 | PC3-9 | FF | 22 | | 68 | | 67 | 64 | |
| 6 | PC3-9 | FF | 4.4 | | 13 | | 11 | 15 | |
| 7 | PC3-9 | DB | 30 | | 96 | | 98 | 97 | |
| 8 | PC3-9 | DB | 6 | | 31 | | 31 | 20 | |
| 9 | PC3-9 | DB | 15 | 67 | 85 | 54 | | | |
| 10 | PC3-9 | FF | 22 | | 30 | | | | |
| 11 | SKBR3 | DB | 30 | | 100 | | 100 | 95 | |
| 12 | PC3-9 | FF | 4.4 | | 26 | | | | 57 |
| 13 | PC3-9 | FF | 4.4 | | | | | 10 | 89 |
| 14 | PC3-9 | FF | 4.4 | | 79 | | | | 88 |
| 15 | MB231 | FF | 4.4 | | 42 | | | | 76 |

TABLE 3

Absolute Yield in Comparison Experiments

Experimental Conditions

| | | | Bead Conc. | Absolute Yield (%) | | | | | |
| | | | | Stripe | | | | | Gap |
| Exp. # | Cell Line | Bead Type | (μg/mL) | M5.1 | M5.2 | M5.3 | M5.4 | M5.5 | M6 |
|---|---|---|---|---|---|---|---|---|---|
| 1 | MB231 | DB | 100 | | 70 | | | | |
| 2 | SKBR3 | FF | 100 | 77 | | | | | |
| 3 | PC3-9 | FF | 4.4 | | 60 | | | | |
| 4 | PC3-9 | FF | 4.4 | 47 | | | | | |
| 5 | PC3-9 | FF | 22 | | 66 | | 71 | 62 | |
| 6 | PC3-9 | FF | 4.4 | | 9 | | 7 | 13 | |
| 7 | PC3-9 | DB | 30 | | 86 | | 68 | 60 | |
| 8 | PC3-9 | DB | 6 | | 33 | | 30 | 24 | |
| 9 | PC3-9 | DB | 15 | 72 | 82 | 53 | | | |
| 10 | PC3-9 | FF | 22 | | 25 | | | | |
| 11 | SKBR3 | DB | 30 | | 36 | | 32 | 47 | |
| 12 | PC3-9 | FF | 4.4 | | 30 | | | | 54 |
| 13 | PC3-9 | FF | 4.4 | | | | | 11 | 60 |
| 14 | PC3-9 | FF | 4.4 | | 64 | | | | 66 |
| 15 | MB231 | FF | 4.4 | | 37 | | | | 71 |

TABLE 4

WBC Carryover in Comparison Experiments

Experimental Conditions

| | | Bead | Bead Conc. | WBC Carryover (WBCs/mL Blood) | | | | | |
| | | | | Stripe | | | | | Gap |
| Exp. # | Cell Line | Type | (μg/mL) | M5.1 | M5.2 | M5.3 | M5.4 | M5.5 | M6 |
|---|---|---|---|---|---|---|---|---|---|
| 1 | MB231 | DB | 100 | | 5404 | | | | |
| 2 | SKBR3 | FF | 100 | 1602 | | | | | |
| 3 | PC3-9 | FF | 4.4 | | 1213 | | | | |
| 4 | PC3-9 | FF | 4.4 | 1665 | | | | | |
| 5 | PC3-9 | FF | 22 | | 2621 | | 4501 | 5600 | |
| 6 | PC3-9 | FF | 4.4 | | 364 | | 397 | 484* | |
| 7 | PC3-9 | DB | 30 | | 838 | | 1876 | 1109 | |
| 8 | PC3-9 | DB | 6 | | 96* | | 27 | 16 | |

TABLE 4-continued

WBC Carryover in Comparison Experiments

| Experimental Conditions | | | WBC Carryover (WBCs/mL Blood) | | | | | |
|---|---|---|---|---|---|---|---|---|
| | | Bead | Stripe | | | | | Gap |
| Exp. # | Cell Line | Bead Type | Conc. (μg/mL) | M5.1 | M5.2 | M5.3 | M5.4 | M5.5 | M6 |
| 9 | PC3-9 | DB | 15 | 2188 | 3358 | 509 | | | |
| 10 | PC3-9 | FF | 22 | | 669 | | | | |
| 11 | SKBR3 | DB | 30 | | 6661 | | 3340 | 448 | |
| 12 | PC3-9 | FF | 4.4 | | 379 | | | | 537 |
| 13 | PC3-9 | FF | 4.4 | | | | | 83 | 176 |
| 14 | PC3-9 | FF | 4.4 | | 281* | | | | 306 |

As can be seen from Table 2, each of the different devices had very high relative yield for most of the different concentrations of beads and bead types. In general, the "gap" device was equivalent to or substantially outperformed the "stripe" devices with respect to relative yield and absolute yield. As shown in Table 4, the "gap" device also was able to achieve a higher white blood cell carryover than the "stripe" devices, thus indicating that a gap design may provide the highest sensitivity for isolating magnetically labeled analytes in a fluid sample.

Figures 15A, 15B:
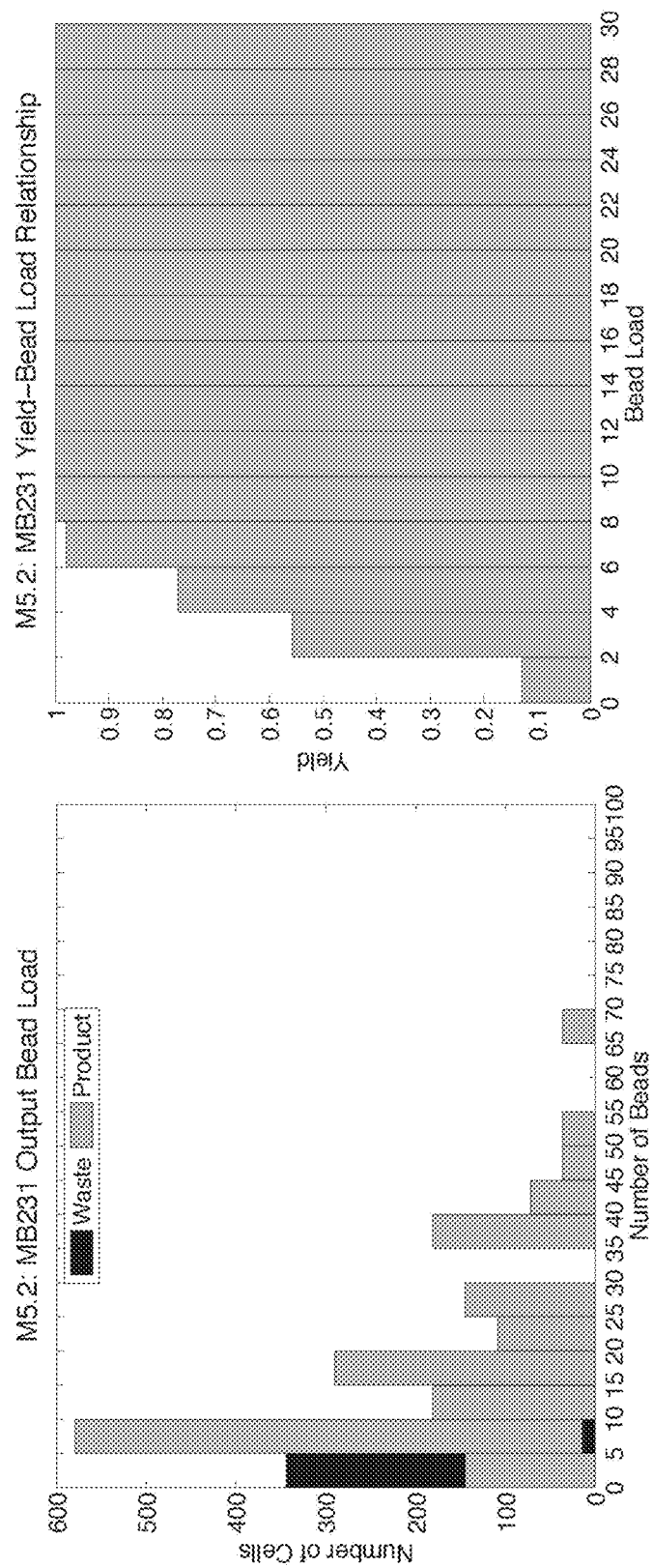
FIGS. 15A and 15B are bar graphs that show the bead load and bead load-yield, respectively, for a stripe device fabricated according to Table 1.

FIGS. 15A and 15B are bar graphs that show the bead load required for capture in a Stripe device fabricated according to M5.2 in Table 1. Here, the bead load is quantified in terms of the number of Dynal MyOne Dynabeads (1 μm diameter) counted on MB321 cells in the blood sample and waste collected in the experiment. If a threshold bead load for capture is defined as the bead load at which 50% of the target cells are captured, then the threshold bead load for the stripe device is a low 3 beads. Accordingly, the stripe design is extremely sensitive to small levels of magnetic moment and provides an effective approach to isolating analytes in a fluid sample.

Example 2—Simulations of Field Gradient in Two-Stage Devices

Figure 16:
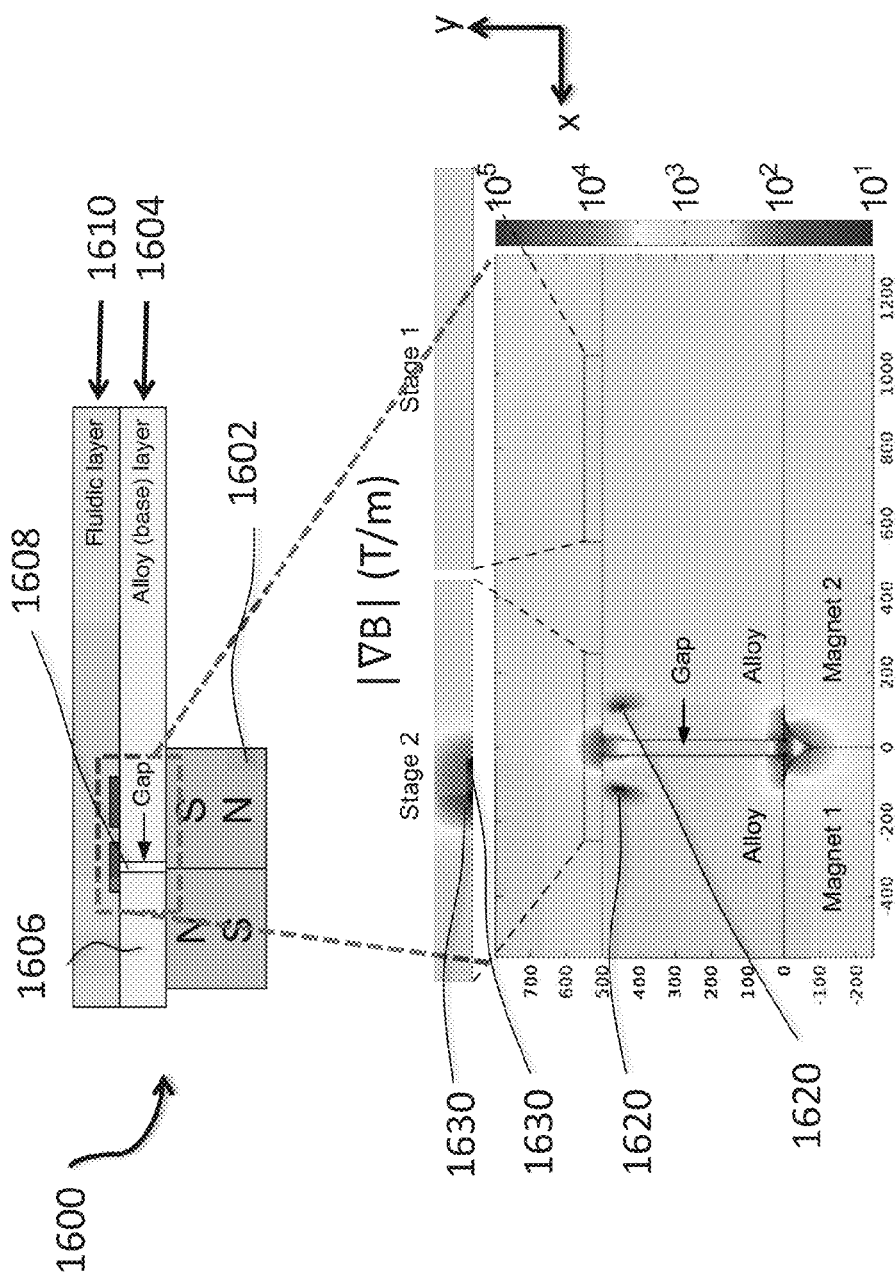
FIG. 16 is a schematic cross-section of an integrated microfluidic device.

Various simulations were also performed to analyze the operation of an integrated microfluidic device constructed according to the present disclosure. For example, FIG. 16 includes a schematic cross-section of an integrated microfluidic device 1600 used in simulations of magnetic field gradients. The device 1600 is based on the configuration shown in FIG. 12, in which a fluidic layer 1610 having two target isolation stages is arranged above a magnetizable layer 1604 ("Alloy (base) layer" in the figure) containing a high magnetic permeability portion 1606 and a low magnetic permeability portion 1608. Two magnets 1602 are arranged beneath the magnetizable layer 1604 to provide the magnetic field. The second isolation stage is a fluidic channel positioned directly above the elongated gap region comprising the low magnetic permeability region. The first isolation stage also is a fluidic channel but is laterally offset from the second isolation stage and the low magnetic permeability region. FIG. 16 also includes a heat map illustrating a simulated magnetic field gradient corresponding to a section of the integrated microfluidic device 1600 that includes a portion of the magnets 1602, the magnetizable layer 1604 and the two isolation stages. The region of the heat map containing the two isolation stages is enlarged for ease of viewing the field gradients.

The simulations were performed using COMSOL finite element analysis software. The permanent magnets 1602 were assumed to be 5 mm×5 mm with 1.3 T remnant magnetization and having the polarity as shown in FIG. 16. The high magnetic permeability material was 500 μm thick and had 1.8 T saturation flux density. The high magnetic permeability material extended 6 mm to the left of the low magnetic permeability material in the gap and 20 mm to the right of the gap. The gap width was 40 μm. The system boundaries were far from the device, with approximately 100 mm×100 mm overall dimensions. The relative permeability (the ratio of the permeability of the medium to that of free space permeability) of the high magnetic permeability material was assumed to be 10,000 and the relative permeability of the low magnetic permeability material was assumed to be 1.

As shown in the heat map, there are both local minima 1620 and local maxima 1630 in the field gradient. For this "gap" structure, in which the low magnetic permeability material is positioned between the high magnetic permeability material, two local maxima 1630 occur within the second isolation stage ("Stage 2") itself. In contrast, given the lateral displacement of the first isolation stage ("Stage 1") from the gap region, the field gradient is fairly uniform across the first isolation stage at a magnitude lower than the maxima in the second isolation stage. As a result, a magnetic particle in the second isolation stage will experience a greater deflection force than the same particle in the first isolation stage. The additional force may be useful for isolating target analytes that express a low overall magnetic permeability (e.g., low magnetic bead load and/or small magnetic bead size). In contrast, the first isolation stage may be used for isolating target analytes that express a higher relative overall magnetic permeability (e.g., high magnetic bead load and/or large magnetic bead size).

Figure 17:
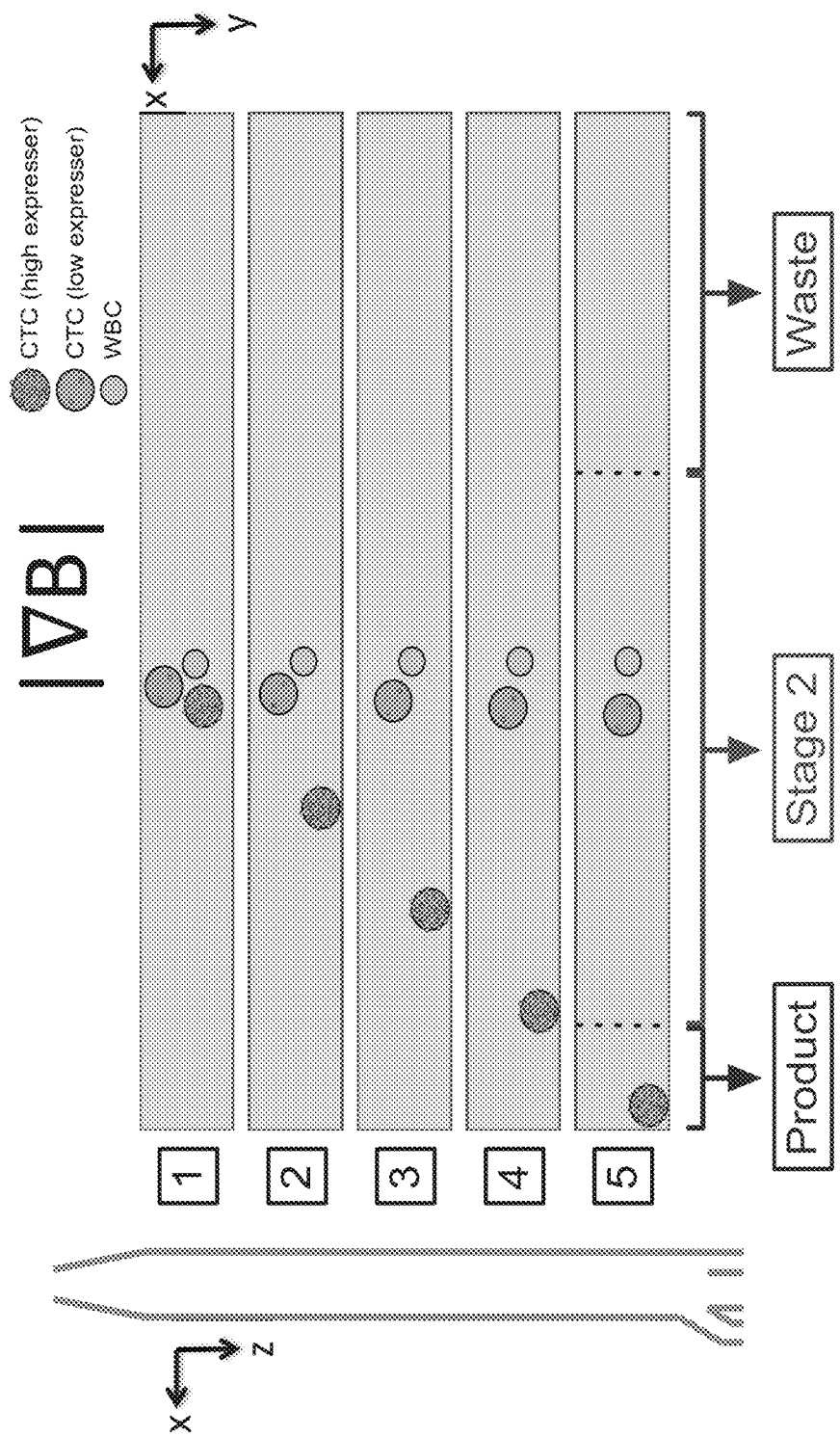
FIG. 17 is a heat map showing a top view of a simulated magnetic field gradient in a first isolation stage of an integrated microfluidic device.

For example, FIG. 17 is a heat map showing a view of the magnetic field gradient in the first isolation stage. The different sections (1-5) of the heat map are cross-sectional views of the gradient in the x-y plane and correspond to different positions along the fluid flow direction, as shown in the top view of the first isolation stage on the left of the heat map. Top view images of the analytes in a fluid sample at the different sections are superimposed on the heat map. At the end of the fluid channel, the first isolation stage separates into three separate pathways: one for the desired product, one for waste material, and one for the remaining fluid sample that contains other target analytes ("Stage 2"). Though not shown, the low magnetic permeability region of the magnetizable layer is located to the left of the first isolation stage (i.e., along the x-direction).

Thus, the strength of the magnetic force generated by the field gradient is slightly greater to the left of the channel shown in FIG. 17 than to the right. Due to the slightly higher magnetic force, target analytes expressing a high overall magnetic permeability will be deflected to the left of the channel and toward the product pathway. For example, three different analytes are shown superimposed over the heat map of FIG. 17: a first circulating tumor cell (CTC) that is bound to a large number of magnetic beads (a high expresser target analyte), a second CTC that is bound to a much smaller number of magnetic beads (a low expresser target analyte), and a white blood cell (WBC). Under fluid flow, the high expresser target is more sensitive to the slightly greater magnetic force and is deflected to the left of the channel, whereas both the low expresser target analyte and the WBC remain analyte are less sensitive and remain traveling along the channel with the fluid flow towards Stage 2.

Figure 18:
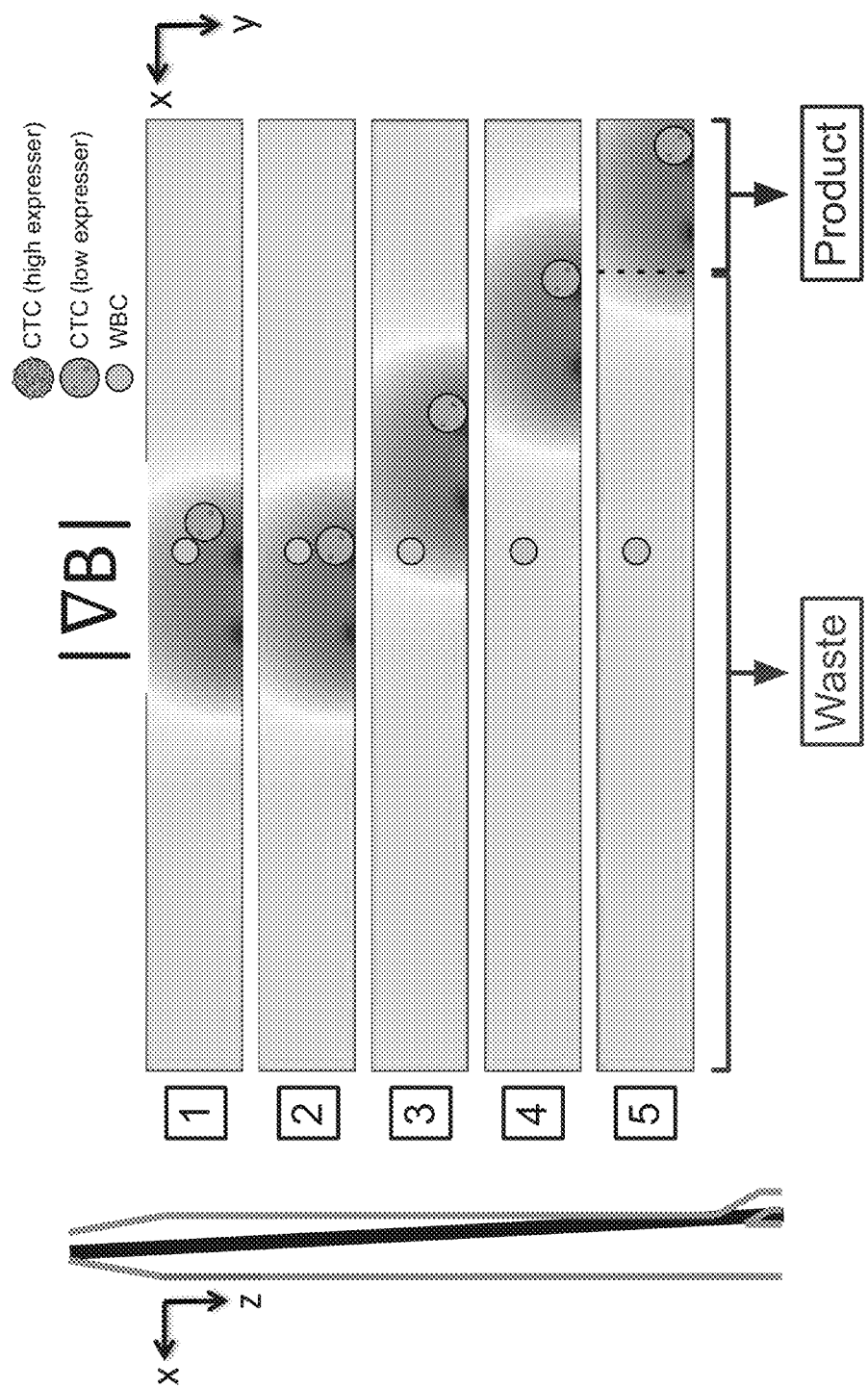
FIG. 18 is a heat map showing a top view of a simulated magnetic field gradient in a second isolation stage of an integrated microfluidic device.

FIG. 18 is a heat map showing a view of the magnetic field gradient in the second isolation stage. Again, the different sections (1-5) of the heat map are cross-sectional views of the gradient in the x-y plane and correspond to different positions along the fluid flow direction, as shown in the top view of the second isolation stage on the left of the heat map. For the second isolation stage, however, the gap region containing low magnetic permeability material is positioned underneath the channel at an oblique angle with respect to the channel's central longitudinal axis. As shown in the heat map, maxima in the magnetic gradient shift to the right of the channel as one moves along from section (1) to section (5). Given the high magnetic force, target analytes expressing a magnetic permeability will be deflected to the right of the channel. For example, the low expresser CTC will be deflected toward the product pathway, whereas the WBC will follow the fluid flow toward the waste pathway.

Experimental tests using the two stage integrated microfluidic device were also conducted to observe how well the first stage and second stage isolate cells. In those experiments, both DYNABEADS® (approximately 1 μm in diameter) and Ferrofluid beads (approximately 160 nm in diameter) were bound to different cell lines (e.g., MB231, PC3-9, and SKBR3) and introduced in a fluid sample into the two stage device. When the bead load was large (i.e., large bead and/or the cell line expressed a high magnetic moment), most cells were captured by the less sensitive Stage 1 (e.g., at least about 80% cell capture). However, when the bead load was small (i.e., small beads and/or the cell line expressed a low magnetic moment) most cells were captured by the more sensitive Stage 2.

Example 3—Simulations of Field Gradients for Different Device Parameters

Figures 20A, 20B:
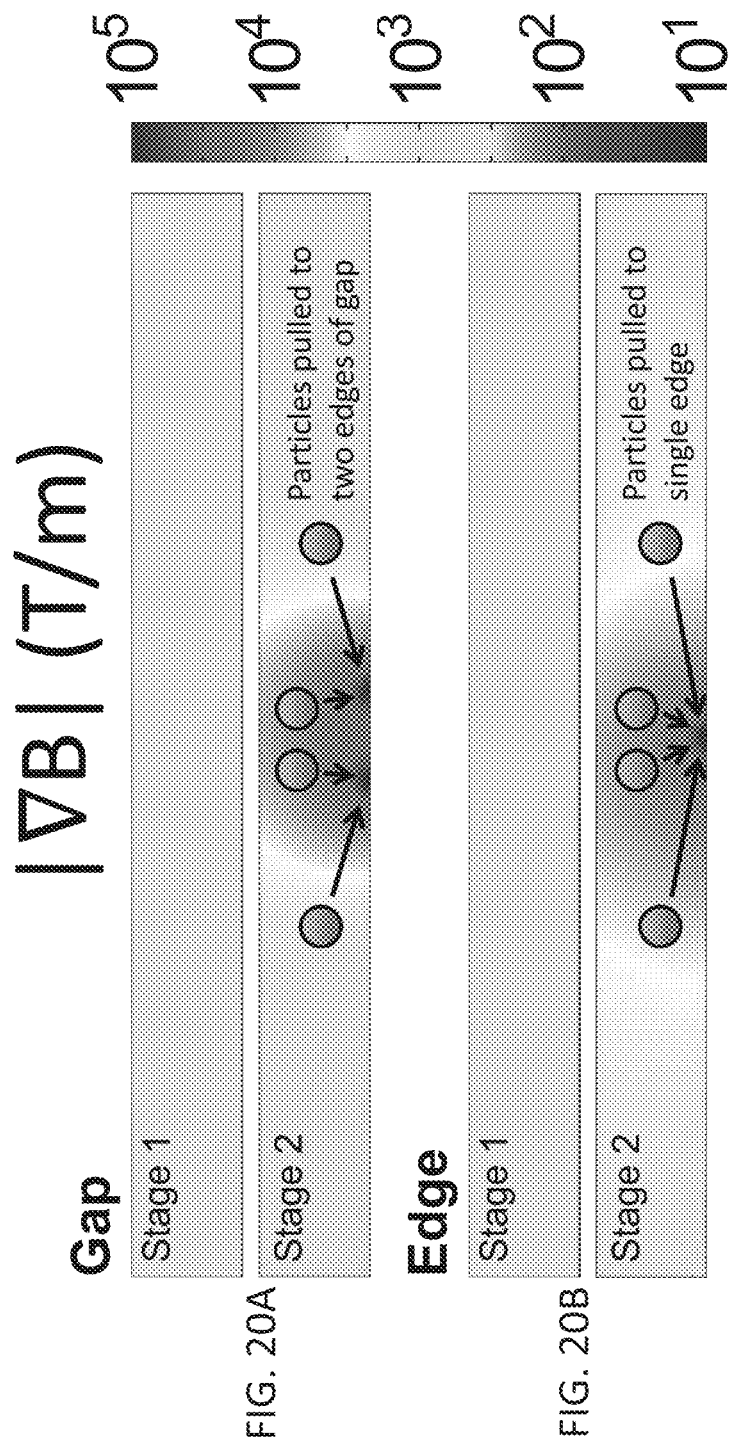
FIGS. 20A-20B are heat map plots of a simulated magnetic field gradient in a first and second isolation stage of an integrated microfluidic device.

FIGS. 20A and 20B include heat map plots of the simulated magnetic field gradient in the first and second isolation stages for both the gap configuration and the "edge" configuration shown in FIGS. 19B and 19C, respectively. In the edge configuration of FIG. 19C, a single local maximum in the magnetic field gradient is produced in the channel corresponding to the second isolation stage (see FIG. 20B), as opposed to two local maxima in the second isolation stage of the gap design (see FIG. 20A). Thus, for the gap configuration of FIG. 19A, magnetic particles (or target analytes bound to magnetic particles) will tend to be pulled toward regions of the channel directly above the two edges corresponding to the two interfaces between the low magnetic permeability material and the high magnetic permeability material. In contrast, in the edge configuration, the magnetic particles (or target anayltes bound to magnetic particles) will be pulled toward a single region corresponding to the area above the single interface between the low magnetic permeability region and the high magnetic permeability material. The edge configuration thus has an advantage that target analytes are deflected toward a single line, instead of being pulled to separate regions of the fluidic channel, improving the collection and isolation of the target analytes.

Figure 22:
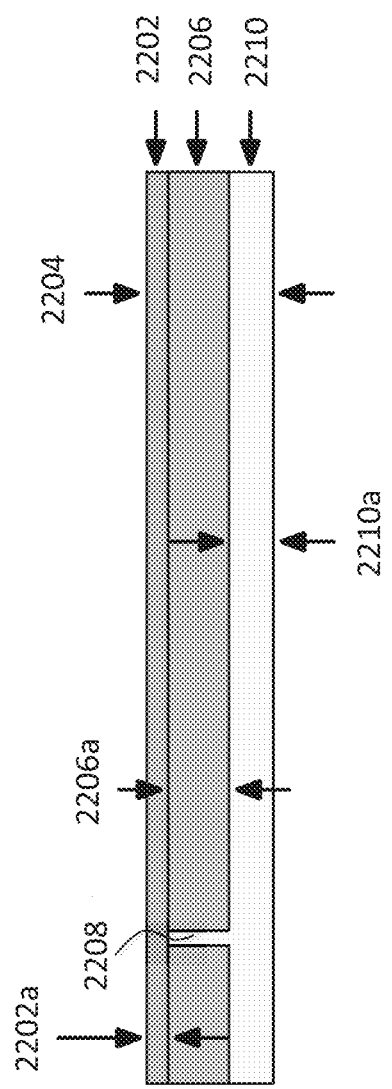
FIG. 22 is a schematic of a cross-section of a portion of an integrated microfluidic device excluding the fluidic channels and magnets.

Various parameters of the integrated microfluidic device can be altered to modify the gradient in magnetic flux and improve the device performance. FIG. 22 is a schematic of a cross-section of the portion of the microfluidic device excluding the microfluidic channels and magnets. As can be seen from FIG. 22, some of the parameters that can be altered to include the thickness 2202a of the passivation/floor layer 2202 beneath the microfluidic channels, the total thickness 2204 of the passivation layer and the magnetizable layer (which includes the high magnetic permeability layer 2206 and the low magnetic permeability gap 2208 shown in FIG. 22), the thickness 2210a of the low magnetic permeability material 2210 (i.e., the "plastic layer") beneath the high magnetic permeability material 2206, and the saturation flux density of the high magnetic permeability material.

To evaluate some of these parameters, several simulations were conducted for the gap configuration shown in FIG. 21A and for the gap configuration shown in FIG. 21B. As indicated above, the simulations were performed using COMSOL finite element analysis software. The permanent magnets were 5 mm×5 mm with 1.3 T remnant magnetization and had a polarity as shown in FIG. 21A. The high magnetic permeability material extended 6 mm to the left of the low magnetic permeability gap and 20 mm to the right of the gap. The gap width was 40 μm. The system boundaries were far from the device, with approximately 100 mm×100 mm overall dimensions. The relative permeability (the ratio of the permeability of the medium to that of free space permeability) of the high magnetic permeability material was assumed to be 10,000 and the relative permeability of the low magnetic permeability material was assumed to be 1. Only one parameter was varied at a time for each simulation.

FIG. 23A corresponds to the configuration in which the two fluidic channels are spaced far apart (i.e., the configuration shown in FIG. 21B). FIG. 23B corresponds to the configuration in which the fluidic channels are spaced close together (i.e., the configuration shown in FIG. 21A). Each channel in both configurations was assumed to be 500 μm wide. Additionally, the low magnetic permeability gap region 2308 was assumed to extend parallel to the central longitudinal axis of the second isolation stage "S2," as opposed to an oblique angle to the axis. For the configuration shown in FIG. 23A, a first edge of the first isolation stage "S1" was assumed to be laterally offset from the low magnetic permeability gap 2308 region by 1000 μm. However, for the configuration shown in FIG. 23B, the lateral offset of the edge of the first isolation stage from the low magnetic permeability gap 2308 was 550 μm. For the purposes of the plots shown in FIGS. 24-26, the configuration shown in FIG. 23A is referred to as "IFD v.9.6/v.9.8," whereas the configuration shown in FIG. 23B is referred to as "IFD v.9.7/v.9.9."

Figure 24B:
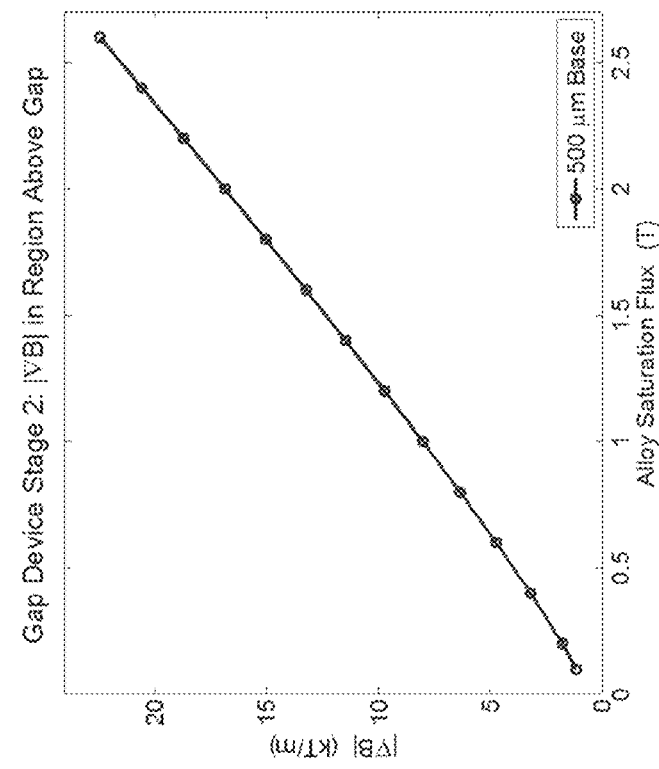
FIGS. 24A-24B are plots of the magnitude of a simulated magnetic flux gradient in a first isolation stage and a second isolation stage, respectively, as a function of saturation flux density.
Figure 24A:
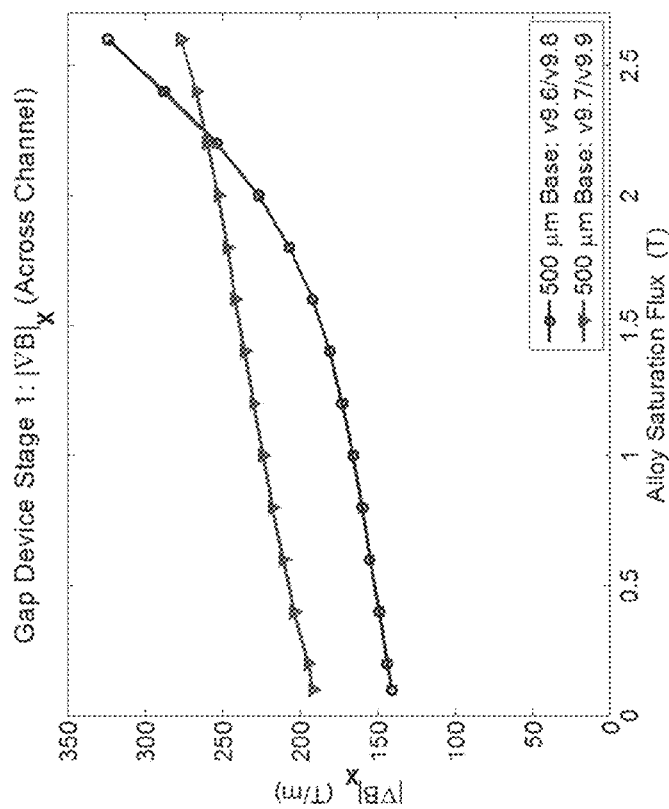

FIG. 24A is a plot of the magnitude of the gradient in the simulated magnetic flux across the width fluidic channel in the first isolation stage (S1) as a function of saturation flux density of the high magnetic permeability material surrounding the gap region. As shown in the plot, the greater the saturation flux density of the high magnetic permeability material, the greater the magnetic force that can be applied in both device configurations. Similarly, as shown in FIG. 24B, the average magnetic force in the second isolation stage (S2) also increases proportionally to saturation flux density of the high magnetic permeability material. Accordingly, a microfluidic device manufactured according to the present disclosure should preferably use the maximum saturation flux density possible for the high magnetic permeability material. For the simulations shown in FIGS. 24A and 24B, the total base thickness (including the floor thickness and the magnetizable layer thickness) was assumed to be 500 µm (i.e., the high magnetic permeability material thickness was fixed at 500 µm, the floor thickness was fixed at 0 µm, and the low magnetic permeability material thickness (i.e., the plastic layer) was fixed at 0 µm.

Figures 25A, 25B:
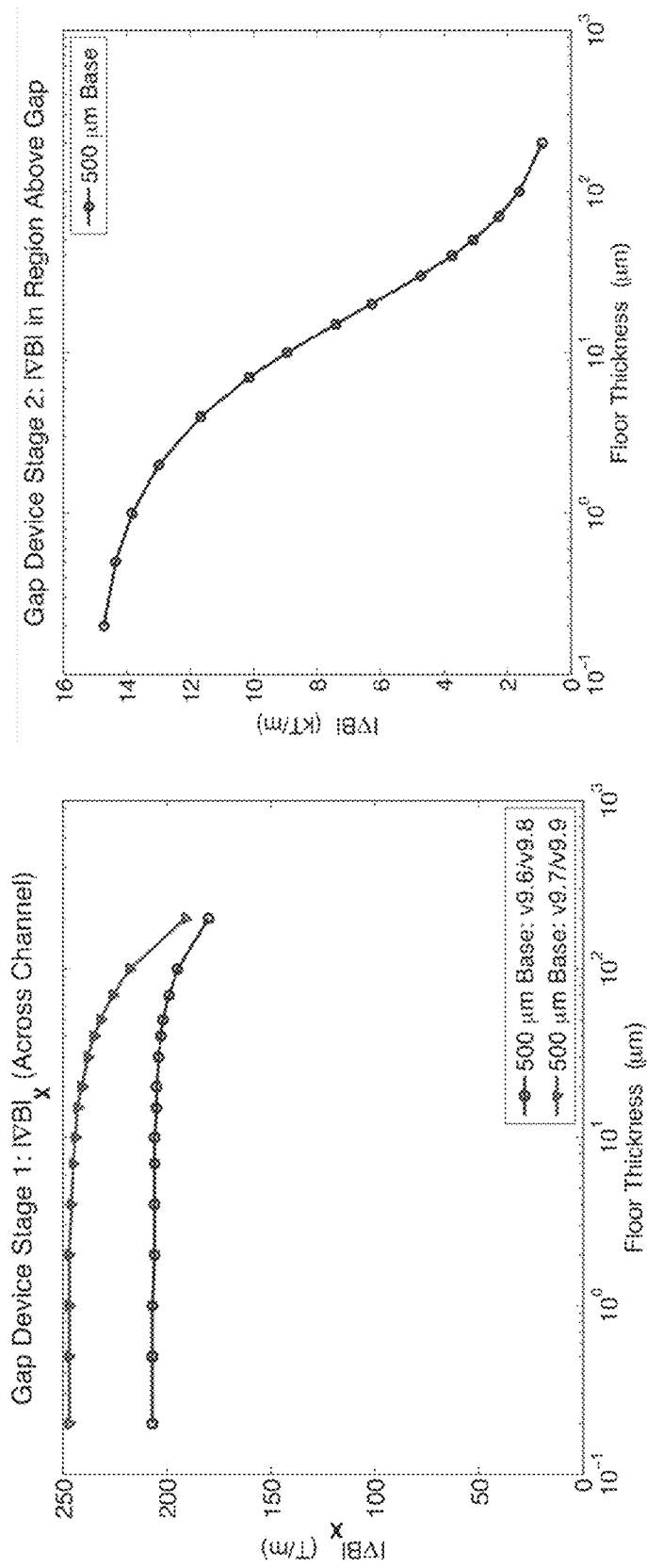
FIGS. 25A-25B are plots of the magnitude of a simulated magnetic flux gradient in a first isolation stage and a second isolation stage, respectively, as a function of passivation layer thickness.

FIG. 25A is a plot of the magnitude of the gradient in the simulated magnetic flux across the width fluidic channel in the first isolation stage (S1) as a function of the passivation layer floor thickness. As can be seen in the plot, for both devices the magnetic force across the channel is essentially constant until a floor thickness of about 100 µm is reached. At that point, the distance of the channel from the high magnetic permeability material begins to reduce the size of the field gradient. The effect of increasing floor thickness is even more prominent in the second isolation stage, as shown in FIG. 25B where the field gradient decreases from about 14 kT/m at 0.1 micron to about less than 1 kT/m at 200 microns. Accordingly, a preferable passivation layer thickness should be less than about 10 µm, or as thin as fabrication processes will allow. The total base thickness (including the floor thickness and the magnetizable layer thickness) for each plot in FIG. 25 was assumed to be 500 µm. The saturation flux was fixed at 1.8 T for the high magnetic permeability material. The high magnetic permeability material thickness was fixed at 500 µm. The low magnetic permeability material located beneath the high magnetic permeability material (i.e., the plastic layer) had a thickness fixed at 0 µm.

Figures 26A, 26B:
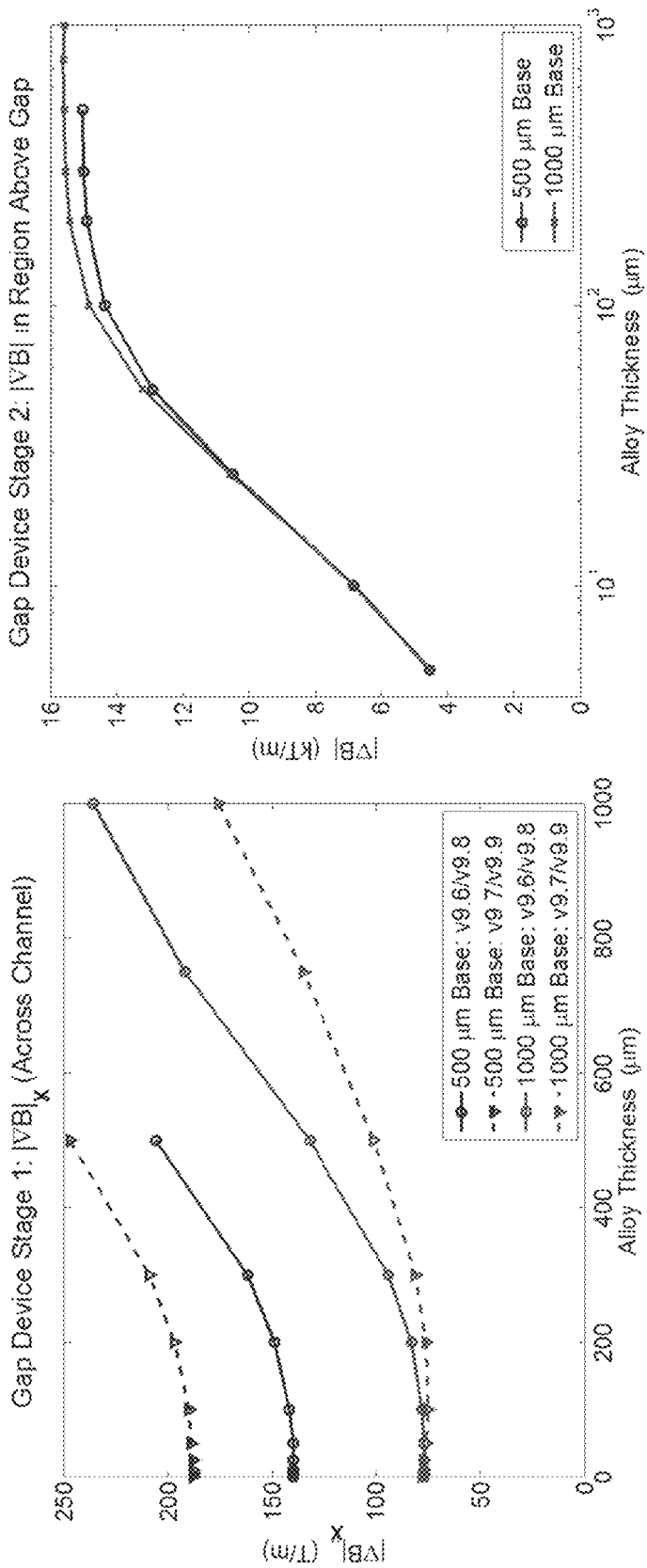
FIGS. 26A-26B are plots of the magnitude of a simulated magnetic flux gradient in a first isolation stage and a second isolation stage, respectively, as a function of a thickness of a high magnetic permeability material (e.g., an alloy material).

FIG. 26A is a plot of the magnitude of the gradient in the simulated magnetic flux across the width fluidic channel in the first isolation stage (S1) as a function of the high magnetic permeability material thickness for different total base thicknesses (i.e., the combined thickness of the passivation layer, the high magnetic permeability material, and the low magnetic permeability material, if any, beneath the high magnetic permeability material). As shown in FIG. 26A, the magnetic force induced by the field gradients generally increases with increasing thickness of the high magnetic permeability material (i.e., the magnetic alloy). FIG. 26A also confirms that the gap configuration in which the two isolation stages are spaced closer together generally performs better for a particular base thickness than the gap configuration in which the isolation stages are separate further apart for the same thickness.

FIG. 26B is a plot of the average magnitude (average over the 100 µm×50 µm region centered over the gap) of the gradient in the simulated magnetic flux in the second isolation stage versus the alloy thickness. As shown in FIG. 26B, even though the magnetic force increases with alloy thickness similar to the first isolation stage, the magnetic force plateaus at around 100-200 µm. Thus, a typical device should have a thickness of at least about 200 µm to maximize the magnetic force in at least the second isolation stage of the microfluidic device. For both of the plots produced in FIGS. 26A and 26B, the high magnetic permeability material saturation flux was fixed at 1.8 T, the passivation floor thickness was fixed at 0 µm, and the base thickness fixed at either 500 µm or 1000 µm, as indicated by legend. The low magnetic permeability thickness (i.e., the plastic layer thickness) was equal to the difference between base thickness 500 µm (or 1000 µm) minus the high magnetic permeability material thickness.

In general, an increase in total base thickness will reduce the magnetic force experienced in the first isolation stage for a fixed high magnetic permeability material thickness on the order of 0.1 to 0.25 T/m per 1 µm increase in base thickness. For the second isolation stage, the magnetic force may experience a minimal increase with increasing base thickness. Accordingly, base thickness does not appear to be a critical parameter for maximizing the magnetic force within the channels.

Other Embodiments

It is to be understood that while the invention has been described in conjunction with the detailed description thereof, the foregoing description is intended to illustrate and not limit the scope of the invention, which is defined by the scope of the appended claims.

What is claimed is:

1. A microfluidic device comprising:
   a plurality of magnets, wherein each magnet of the plurality of magnets emits a magnetic field;
   a magnetizable layer arranged adjacent to the plurality of magnets; and
   a microfluidic channel arranged adjacent to a surface of the magnetizable layer, wherein the magnetizable layer is configured to induce a gradient in the magnetic field of at least one of the magnets, wherein the gradient extends into the microfluidic channel, wherein the magnetizable layer comprises
      a high magnetic permeability region comprising a composite material including a plurality of magnetic particles or comprising a high magnetic permeability material, and
      a low magnetic permeability region directly adjacent to the high magnetically permeable region,
   wherein a central longitudinal axis of the microfluidic channel extends substantially in parallel with an interface between the high magnetic permeability region and the low magnetic permeability region, and
   wherein the magnetizable layer is configured to be removably secured to the plurality of magnets or to the microfluidic channel.

2. The microfluidic device of claim 1, comprising a plurality of high magnetic permeability regions and a plurality of low magnetic permeability regions arranged in an array that alternates between high and low magnetic permeability regions, wherein each high magnetic permeability region comprises the composite material.

3. The microfluidic device of claim 1, wherein the high magnetic permeability region comprises the composite material, and wherein the composite material comprises one or more of a polymeric material, a glass material, or a ceramic material.

4. The microfluidic device of claim 1, wherein a first magnet of the plurality of magnets is arranged above the magnetizable layer and a second magnet of the plurality of magnets is arranged below the magnetizable layer and facing the first magnet.

5. The microfluidic device of claim 4, wherein a side of the first magnet that faces the second magnet has a first magnetic pole, and a side of the second magnet that faces the first magnet has a second magnetic pole that is opposite in polarity to the first magnetic pole.

6. The microfluidic device of claim 1, wherein the low magnetic permeability region has a relative magnetic permeability that is lower than a relative magnetic permeability of the high magnetic permeability region by a factor of at least about 4.

7. The microfluidic device of claim 1, wherein the microfluidic channel is rotatably fixed with respect to the magnetizable layer.

* * * * *